United States Patent
Moriwaki et al.

(10) Patent No.: US 9,688,612 B2
(45) Date of Patent: *Jun. 27, 2017

(54) AXIALLY CHIRAL N-(2-ACYLARYL)-2-[5,7-DIHYDRO-6H-DIBENZO[C,E]AZEPIN-6-YL] ACETAMIDE COMPOUND AND CHIRALITY INTERCONVERSION METHOD OF A-AMINO ACID USING THE SAME

(71) Applicant: HAMARI CHEMICALS, LTD., Osaka (JP)

(72) Inventors: Hiroki Moriwaki, Osaka (JP); Ryosuke Takeda, Osaka (JP); Akie Kawamura, Osaka (JP); Aki Kawashima, Osaka (JP); Vadim A. Soloshonok, Norman, OK (US)

(73) Assignee: HAMARI CHEMICALS, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/651,857

(22) PCT Filed: Dec. 17, 2013

(86) PCT No.: PCT/JP2013/083711
§ 371 (c)(1),
(2) Date: Jun. 12, 2015

(87) PCT Pub. No.: WO2014/098063
PCT Pub. Date: Jun. 26, 2014

(65) Prior Publication Data
US 2015/0321994 A1    Nov. 12, 2015

(30) Foreign Application Priority Data
Dec. 17, 2012   (JP) .................. 2012-275160

(51) Int. Cl.
*C07D 223/14*     (2006.01)
*C07D 223/18*     (2006.01)
(Continued)

(52) U.S. Cl.
CPC ............ *C07C 227/30* (2013.01); *C07B 53/00* (2013.01); *C07C 227/32* (2013.01);
(Continued)

(58) Field of Classification Search
CPC .. C07D 223/14; C07D 223/18; C07C 227/30; C07F 15/045
(Continued)

(56) References Cited

U.S. PATENT DOCUMENTS

2006/0173211 A1   8/2006   Kim et al.
2008/0108830 A1   5/2008   Hamada
(Continued)

FOREIGN PATENT DOCUMENTS

EP    1 277 755    1/2003
EP    3 006 449    4/2016
(Continued)

OTHER PUBLICATIONS

Moriwaki et al., Practical Asymmetric Synthesis of Alpha-Amino Acids Using the New Generation of Axially Chiral Ni(II) Chelated Glycine Schiff Base, Peptide Science, 50th, pp. 115-118, 2013.*
(Continued)

*Primary Examiner* — Brenda Coleman
(74) *Attorney, Agent, or Firm* — Wenderoth, Lind & Ponack, L.L.P.

(57) ABSTRACT

An object of the present invention is to provide a method for producing an optically active amino acid in high yield and in a highly enantioselective manner, which method has fewer restrictions on the material that can be used as the substrate, and to provide, among others, a compound useful as a chiral auxiliary for the method. The present invention provides an N-(2-acylaryl)-2-[5,7-dihydro-6H-dibenzo[c,e]azepin-6-yl]acetamide compound represented by Formula (1):

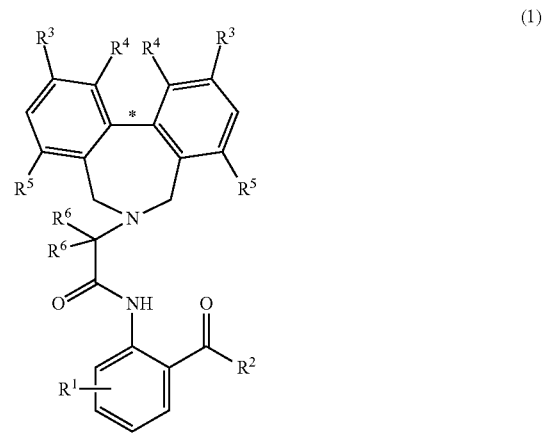

or a salt thereof, or a metal complex represented, by Formula (3):

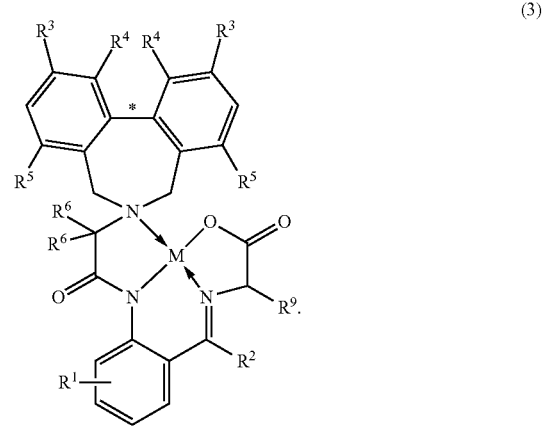

9 Claims, 10 Drawing Sheets

(51) Int. Cl.

| | | |
|---|---|---|
| C07C 227/30 | (2006.01) | |
| C07C 319/12 | (2006.01) | |
| C07D 209/20 | (2006.01) | |
| C07B 53/00 | (2006.01) | |
| C07C 227/32 | (2006.01) | |
| C07C 229/08 | (2006.01) | |
| C07C 229/36 | (2006.01) | |
| C07F 15/04 | (2006.01) | |

(52) U.S. Cl.
CPC .......... *C07C 229/08* (2013.01); *C07C 229/36* (2013.01); *C07C 319/12* (2013.01); *C07D 209/20* (2013.01); *C07D 223/14* (2013.01); *C07F 15/045* (2013.01)

(58) Field of Classification Search
USPC .................. 540/541, 586; 556/116, 137, 148
See application file for complete search history.

(56) References Cited

U.S. PATENT DOCUMENTS

| 2009/0023931 A1 | 1/2009 | Mook et al. |
| 2011/0040101 A1 | 2/2011 | Mook et al. |
| 2016/0102045 A1 | 4/2016 | Moriwaki et al. |

FOREIGN PATENT DOCUMENTS

| JP | 2006-213712 | 8/2006 |
| JP | 2008-115179 | 5/2008 |
| JP | 2009-23989 | 2/2009 |
| WO | 01/81349 | 11/2001 |

OTHER PUBLICATIONS

Extended European Search Report issued Jul. 4, 2016 in corresponding European Application No. 13864879.5.
International Preliminary Report on Patentability issued Jun. 23, 2015 in International Application No. PCT/JP2013/083711.
International Search Report issued Apr. 1, 2014 in International (PCT) Application No. PCT/JP2013/083711.
V. A. Soloshonok et al., "Application of Modular Nucleophilic Glycine Equivalents for Truly Practical Asymmetric Synthesis of β-Substituted Pyroglutamic Acids", Tetrahedron Letters, vol. 46, pp. 1107-1110, 2005.
T. K. Ellis et al., "New Generation of Nucleophilic Glycine Equivalents", Tetrahedron Letters, vol. 46, pp. 941-944, 2005.
V. A. Soloshonok et al., "Resolution/Deracemization of Chiral α-Amino Acids Using Resolving Reagents with Flexible Stereogenic Centers", J. Am. Chem. Soc., vol. 131, pp. 7208-7209, 2009.
H. Park et al., "Bioinspired Chemical Inversion of L-Amino Acids to D-Amino Acids", J. Am. Chem. Soc., vol. 129, pp. 1518-1519, 2007.
N. Maigrot et al., "Asymmetric Nucleophilic Acylation via Metalated α-Amino Nitriles Possessing an Axially Disymmetric Tertiary Amino Group", J. Org. Chem., vol. 50, pp. 3916-3918, 1985.
Registry 1317399-32-8, Entered STN: Aug. 14, 2011.
Registry 1114360-57-4, Entered STN: Mar. 2, 2009.
Registry 1114360-59-6, Entered STN: Mar. 2, 2009.
Registry 1114360-61-0, Entered STN: Mar. 2, 2009.
Registry 292636-37-4, Entered STN: Oct. 4, 2000.

* cited by examiner

Detector A – 1 (254nm)

| Peak No. | Retention Time | Area | Area% |
|---|---|---|---|
| 1 | 26.656 | 2627524 | 99.0363 |
| 2 | 28.525 | 25568 | 0.9637 |

| Total | | | |
|---|---|---|---|
| | | 2653092 | 100.0000 |

Detector A – 1 (254nm)

| Peak No. | Retention Time | Area | Area% |
|---|---|---|---|
| 1 | 26.704 | 11726232 | 98.5390 |
| 2 | 28.452 | 173861 | 1.4610 |

| Total | | | |
|---|---|---|---|
| | | 11900093 | 100.0000 |

Detector A - 1 (254nm)

| Peak No. | Retention Time | Area | Area% |
|---|---|---|---|
| 1 | 29.285 | 26406303 | 95.85 |
| 2 | 31.442 | 1144042 | 4.15 |

| Total | | 27550345 | 100.00 |
|---|---|---|---|

Detector A - 1 (254nm)

| Peak No. | Retention Time | Area | Area% |
|---|---|---|---|
| 1 | 26.497 | 21752335 | 96.6166 |
| 2 | 27.538 | 761752 | 3.3834 |

| Total | | 22514087 | 100.0000 |
|---|---|---|---|

Detector A - 1 (254nm)

| Peak No. | Retention Time | Area | Area% |
|---|---|---|---|
| 1 | 24.333 | 33280336 | 99.73 |
| 2 | 25.685 | 88746 | 0.27 |

| Total | | | |
|---|---|---|---|
| | | 33369083 | 100.00 |

Detector A - 1 (254nm)

| Peak No. | Retention Time | Area | Area% |
|---|---|---|---|
| 1 | 35.581 | 1315271 | 2.9426 |
| 2 | 36.561 | 43382941 | 97.0574 |

| Total | | | |
|---|---|---|---|
| | | 44698213 | 100.0000 |

Detector A (254nm)

| Peak No. | Retention Time | Area | Area% |
|---|---|---|---|
| 1 | 20.294 | 5101 | 0.53 |
| 2 | 23.132 | 958213 | 99.47 |

| Total | | | |
|---|---|---|---|
| | | 963314 | 100.00 |

Detector A - 2 (200nm)

| Peak No. | Retention Time | Area | Area% |
|---|---|---|---|
| 1 | 16.353 | 44371208 | 99.4580 |
| 2 | 19.089 | 241823 | 0.5420 |

| Total | | | |
|---|---|---|---|
| | | 44613031 | 100.0000 |

Detector A - 1 (200nm)

| Peak No. | Retention Time | Area | Area% |
|---|---|---|---|
| 1 | 7.744 | 625245 | 3.39 |
| 2 | 8.429 | 17838428 | 96.61 |

| Total | | | |
|---|---|---|---|
| | | 18463673 | 100.00 |

Detector A - 1 (254nm)

| Peak No. | Retention Time | Area | Area% |
|---|---|---|---|
| 1 | 26.714 | 12505469 | 99.4564 |
| 2 | 28.460 | 68355 | 0.5436 |

| Total | | | |
|---|---|---|---|
| | | 12573824 | 100.0000 |

Detector A - 1 (254nm)

| Peak No. | Retention Time | Area | Area% |
|---|---|---|---|
| 1 | 26.632 | 2654799 | 98.6018 |
| 2 | 28.499 | 37645 | 1.3982 |

| Total | | | |
|---|---|---|---|
| | | 2692444 | 100.0000 |

Detector A - 1 (254nm)

| Peak No. | Retention Time | Area | Area% |
|---|---|---|---|
| 1 | 26.802 | 26389574 | 99.5637 |
| 2 | 28.432 | 115652 | 0.4363 |

| Total | | | |
|---|---|---|---|
| | | 26505226 | 100.0000 |

Detector A - 1 (254nm)

| Peak No. | Retention Time | Area | Area% |
|---|---|---|---|
| 1 | 26.887 | 24274305 | 98.5792 |
| 2 | 28.525 | 349853 | 1.4208 |

| Total | | | |
|---|---|---|---|
| | | 24624158 | 100.0000 |

Detector A - 1 (254nm)

| Peak No. | Retention Time | Area | Area% |
|---|---|---|---|
| 1 | 25.345 | 4475417 | 96.2168 |
| 2 | 27.034 | 175971 | 3.7832 |

| Total | | | |
|---|---|---|---|
| | | 4651387 | 100.0000 |

Detector A - 1 (254nm)

| Peak No. | Retention Time | Area | Area% |
|---|---|---|---|
| 1 | 25.405 | 32049447 | 97.6605 |
| 2 | 26.845 | 767748 | 2.3395 |

| Total | | | |
|---|---|---|---|
| | | 32817195 | 100.0000 |

Detector A - 1 (254nm)

| Peak No. | Retention Time | Area | Area% |
|---|---|---|---|
| 1 | 21.349 | 10324525 | 97.8505 |
| 2 | 22.202 | 226798 | 2.1495 |

| Total | | | |
|---|---|---|---|
| | | 10551322 | 100.0000 |

Detector A - 1 (254nm)

| Peak No. | Retention Time | Area | Area% |
|---|---|---|---|
| 1 | 21.358 | 9365480 | 98.0319 |
| 2 | 22.211 | 188022 | 1.9681 |

| Total | | | |
|---|---|---|---|
| | | 9553502 | 100.0000 |

Detector A - 1 (254nm)

| Peak No. | Retention Time | Area | Area% | Component Name |
|---|---|---|---|---|
| 1 | 19.809 | 21727150 | 96.31 | |
| 2 | 20.617 | 833201 | 3.69 | |

| Total | | | | |
|---|---|---|---|---|
| | | 22560351 | 100.00 | |

AXIALLY CHIRAL N-(2-ACYLARYL)-2-[5,7-DIHYDRO-6H-DIBENZO[C,E]AZEPIN-6-YL] ACETAMIDE COMPOUND AND CHIRALITY INTERCONVERSION METHOD OF A-AMINO ACID USING THE SAME

TECHNICAL FIELD

The present invention relates to an axially chiral N-(2-acylaryl)-2-[5,7-dihydro-6H-dibenzo[c,e]azepin-6-yl]acetamide compound and a chirality inversion method of an α-amino acid using the compound as a template. The present invention also relates to a metal complex used as an intermediate for the chirality inversion method, the metal complex having, as a ligand, a condensate of an α-amino acid and an N-(2-acylaryl)-2-[5,7-dihydro-6H-dibenzo[c,e]azepin-6-yl]ac etamide compound.

BACKGROUND ART

Optically pure α-amino acids are useful as a building block for designing various physiologically active substances and drugs. Recently, it was found that substances containing, in particular, a D-α-amino acid, which hardly occurs in nature, have unique physiological effects. Therefore, a process for conveniently obtaining an optically pure D-α-amino acid as a raw material is desired. Also, peptides and proteins composed of optically active unnatural synthetic α-amino acids have a more stable higher-order structure and an improved stability against hydrolytic enzymes than naturally occurring ones. Therefore, the importance of such optically active unnatural synthetic α-amino acids in drug development has been increasing, sad the development of a process for conveniently obtaining the optically active α-amino acids is an urgent issue.

As a production method of an optically active α-amino acid, optical resolution of a racemic mixture of an α-amino acid is classically known, and recently a fermentation method or an enzymatic method are known to easily produce L-α-amino acids. Regarding D-α-amino acids, deracemization of a racemic mixture and chirality inversion from an easily obtainable L-α-amino acid have been studied. Reported as examples of the methods are a method using a chiral ligand having an asymmetric carbon atom (see Non Patent Literature 1 etc.), a method using a chiral ligand having axial chirality (see Non Patent Literature 2, Patent Literature 1 and 2, etc.), etc.

However, in each method, there is a problem of generally slow inversion rate. In particular, in cases of amino acids having a sterically-bulky side chain, such as valine and isoleucine, there are problems of extremely slow reaction rate and low optical purity of the obtained product.

Consequently, none of the known methods are industrially satisfactory, and for the reason, the development of an industrially applicable production method of an optically active α-amino acid has been demanded.

CITATION LIST

Patent Literature

Patent Literature 1: U.S. Pat. No. 7,268,252
Patent Literature 2: U.S. Pat. No. 7,847,124

Non Patent Literature

Non Patent Literature 1: V. Soloshonok et al., J. Am. Chem. Soc., 2009, 131, 7208
Non Patent Literature 2: H. Park et al., J. Am. Chem. Soc., 2007, 129, 1518

SUMMARY OF INVENTION

Technical Problem

The present inventors made efforts to solve the above problems, and as a result, successfully created an N-(2-acylaryl)-2-[5,7-dihydro-6H-dibenzo[c,e]azepin-6-yl]ac etamide compound, which can be used as a template in the chirality inversion of an α-amino acid. By a method the inventors found, an α-amino acid having a desired chirality is obtained in high yield and in a highly enantioselective manner. The method is as follows. An S- or R-form of the acetamide compound is selected as appropriate and condensed with an α-amino acid of which chirality is to be interconverted, and the condensate is made into a metal complex. The metal complex is subsequently heated under basic conditions for chirality interconversion of the α-amino acid moiety, and then subjected to acid treatment to release the chirality-converted α-amino acid as intended. This method is a generally applicable method for interconverting the chirality of an α-amino acid as desired in a simple, inexpensive, and industrially advantageous manner. The present inventors conducted further examination and completed the present invention.

Solution to Problem

That is, the present invention includes the following [1] to [9].

[1] A compound represented by Formula (1):

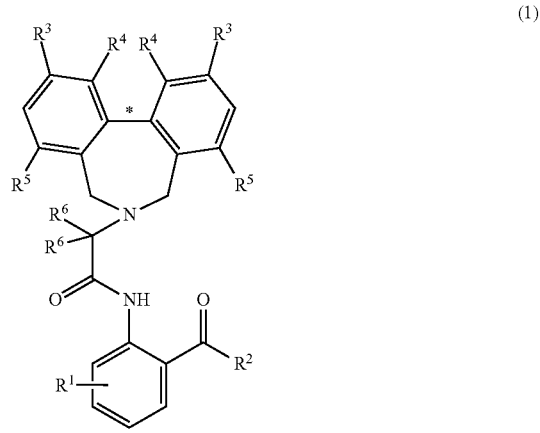

(1)

(wherein $R^1$ denotes hydrogen, an optionally substituted alkyl group (for example, an alkyl group in which a part or all of the hydrogen atoms are replaced with fluorine atoms), an optionally substituted alkynyl group, an optionally substituted alkenyl group, an optionally substituted alkoxy group, an optionally substituted cycloalkyl group, an optionally substituted aryl group, an optionally substituted heteroaryl group, a halogen atom, or a nitro group;

$R^2$ denotes hydrogen, an optionally substituted alkyl group (for example, an alkyl group in which a part or all of the hydrogen atoms are replaced with fluorine atoms), an optionally substituted alkynyl group, an optionally substituted alkenyl group, an optionally substituted cycloalkyl group, an optionally substituted aryl group, or an optionally substituted heteroaryl group;

$R^3$ and $R^4$ each independently denote hydrogen, an optionally substituted alkyl group (for example, an alkyl group in which a part or all of the hydrogen atoms are replaced with fluorine atoms), an optionally substituted alkynyl group, an optionally substituted alkenyl group, an optionally substituted alkoxy group, an optionally substituted cycloalkyl group, an optionally substituted aryl group, an optionally substituted heteroaryl group, or a halogen atom;

the two $R^3$s may be the same or different;

the two $R^4$s may be the same or different;

$R^3$ and $R^4$ may form a ring together with the carbon atoms to which they are bonded;

$R^5$ denotes hydrogen, an optionally substituted alkyl group (for example, an alkyl group in which a part or all of the hydrogen atoms are replaced with fluorine atoms), an optionally substituted alkynyl group, an optionally substituted alkenyl group, an optionally substituted alkoxy group, an optionally substituted cycloalkyl group, an optionally substituted aryl group, an optionally substituted heteroaryl group, a carboxyl group, a halogen atom, —COOR$^7$, or —C(OH)(R$^7$)$_2$;

the two $R^5$s may be the same or different;

$R^6$ denotes hydrogen, an optionally substituted alkyl group, an optionally substituted cycloalkyl group, or a halogen atom;

the two $R^6$s may be the same or different;

the two $R^6$s may form a ring together with the carbon atom to which they are bonded;

$R^7$ denotes hydrogen, an optionally substituted alkyl group, an optionally substituted aryl group, or an optionally substituted heteroaryl group; and

* denotes a chiral axis), or a salt thereof.

[2] The compound according to the above [1] or a salt thereof, wherein, in each of the two pairs of $R^3$ and $R^4$ in Formula (1), $R^3$ and $R^4$ form an aromatic ring or an alicyclic structure together with the aromatic-ring carbon atoms to which they are bonded and $R^2$ denotes a group represented by the following formula:

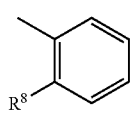

(wherein $R^8$ denotes a hydrogen atom or a halogen atom), the compound being represented by Formula (2):

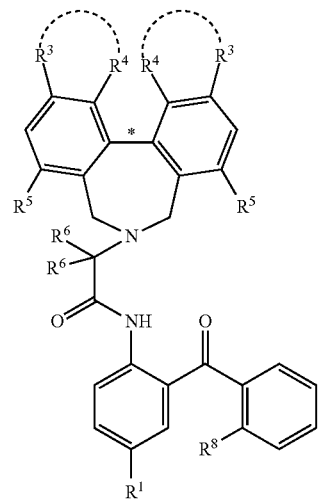

(wherein $R^1$, $R^5$ and $R^6$ have the same meanings as defined in the above [1]).

[3] The compound according to the above [2] or a salt thereof, wherein $R^1$ is hydrogen, chlorine, a methyl group, or a nitro group; and $R^5$ and $R^6$ are each hydrogen.

[4] A metal complex represented by Formula (3):

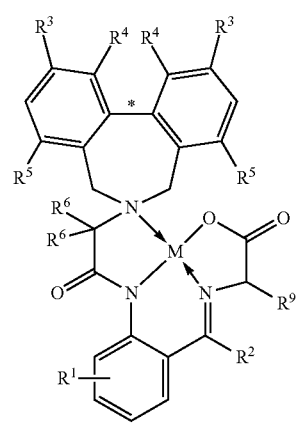

(wherein $R^1$ denotes hydrogen, an optionally substituted alkyl group (for example, an alkyl group in which a part or all of the hydrogen atoms are replaced with fluorine atoms), an optionally substituted alkynyl group, an optionally substituted alkenyl group, an optionally substituted alkoxy group, an optionally substituted cycloalkyl group, an optionally substituted aryl group, an optionally substituted heteroaryl group, a halogen atom, or a nitro group;

$R^2$ denotes hydrogen, an optionally substituted alkyl group, an optionally substituted alkynyl group, an optionally substituted alkenyl group, an optionally substituted cycloalkyl group, an optionally substituted aryl group, or an optionally substituted heteroaryl group, $R^3$ and $R^4$ each independently denote hydrogen, an optionally substituted alkyl group (for example, an alkyl group in which a part or all of the hydrogen atoms are replaced with fluorine atoms), an optionally substituted alkynyl group, an optionally substituted alkenyl group, an optionally substituted alkoxy group, an optionally substituted cycloalkyl group, an optionally substituted aryl group, an optionally substituted heteroaryl group, or a halogen atom;

the two $R^3$s may be the same or different;

the two $R^4$s may be the same or different;

$R^3$ and $R^4$s may form a ring together with the carbon atoms to which they are bonded;

$R^5$ denotes hydrogen, an optionally substituted alkyl group (for example, an alkyl group in which a part or all of the hydrogen atoms are replaced with fluorine atoms), an optionally substituted alkynyl group, an optionally substituted alkenyl group, an optionally substituted alkoxy group, an optionally substituted cycloalkyl group, an optionally substituted aryl group, an optionally substituted heteroaryl group, a carboxyl group, a halogen atom, —COOR$^7$, or —C(OH) (R$^7$)$_2$;

the two $R^5$s may be the same or different;

$R^6$ denotes hydrogen, an optionally substituted alkyl group, an optionally substituted cycloalkyl group, or a halogen atom;

the two $R^6$s may be the same or different;

the two $R^6$s may form a ring together with the carbon atom to which they are bonded;

$R^7$ denotes hydrogen, an optionally substituted alkyl group, an optionally substituted aryl group, or an optionally substituted heteroaryl group;

$R^9$ denotes an optionally substituted alkyl group (for example, an alkyl group in which a part or all of the hydrogen atoms are replaced with fluorine atoms), an optionally substituted alkynyl group, an optionally substituted alkenyl group, an optionally substituted cycloalkyl group, an optionally substituted aryl group, an optionally substituted heteroaryl group, an optionally substituted aralkyl group, or an optionally substituted heteroarylalkyl group;

\* denotes a chiral axis; and

M denotes a divalent metallic cation).

[5] The metal complex according to the above [4] wherein, in each of the two pairs of $R^3$ and $R^4$ in Formula (3), $R^3$ and $R^4$ form an aromatic ring or an alicyclic structure together with the aromatic-ring carbon atoms to which they are bonded; and $R^2$ denotes a group represented by the following formula:

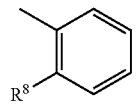

(wherein $R^8$ denotes a hydrogen atom or a halogen atom), the metal complex being represented by Formula (4):

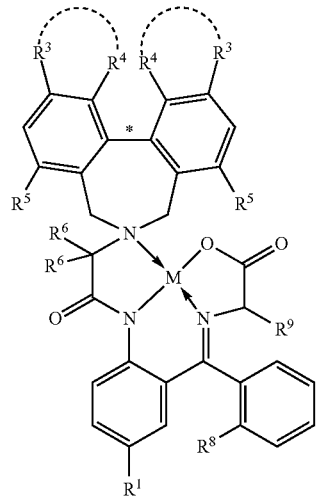

(wherein $R^1$, $R^5$ and $R^6$ have the same meanings as defined in the above [4].

[6] The metal complex according to the above [4] or [5], wherein $R^1$ is hydrogen, chlorine, a methyl group, or a nitro group; in each of the two pairs of $R^3$ and $R^4$, $R^3$ and $R^4$ form an aromatic ring or an alicyclic structure together with the aromatic-ring carbon atoms to which they are bonded; $R^5$ and $R^6$ are each hydrogen; and M denotes a nickel cation, a copper cation, a palladium cation, or a platinum cation.

[7] A method for interconverting the configuration of an α-amino acid, the method comprising heating, under basic conditions, the divalent metal cation complex represented by Formula (3) in claim 4 derived from an imine compound produced from a selected optically active R- or S-form of the N-(2-acylaryl)-2-[5, 7-dihydro-6H-dibenzo [c,e]azepin-6-yl]ac etamide compound represented by Formula (1) in claim 1 or a salt thereof and an α-amino acid in order to convert the configuration of the α carbon in the α-amino acid moiety, and subjecting the metal complex to acid decomposition to give an optically pure α-amino acid enantiomer having a converted configuration.

[8] The method according to the above [7], wherein the α-amino acid or a salt thereof is represented by Formula (5);

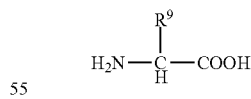

wherein $R^9$ is as defined in the above [4]) and is a mixture of optical isomers, or a pure optical isomer.

As an alternative, a method for converting the chirality (configuration) of an α-amino acid, the method comprising heating, under basic conditions, the divalent metal cation complex represented by formula (3) in the above [4] derived from an imine compound produced from an optically active N-(2-acylaryl)-2-[5, 7-dihydro-6H-dibenzo[c,e]azepin-6-yl] ac etamide compound having a selected R- or S-configuration represented by Formula (1) in the above [1] or a salt thereof and an α-amino acid represented by Formula (5) in order to convert the configuration of the α carbon in the α-amino acid moiety via an enolate intermediate, and decomposing the metal complex using an acid to give an α-amino acid enantiomer having a desired configuration.

As an alternative, a method for converting the chirality (configuration) of an α-amino acid, the method comprising heating, under basic conditions, the divalent metal cation complex represented by Formula (3) in the above [4] derived from an imine compound produced from an optically active N-(2-acylaryl)-2-[5, 7-dihydro-6H-dibenzo[c,e]azepin-6-yl] acetamide compound having a selected R- or S-configuration represented by Formula (1) in the above [1] or a salt thereof and an α-amino acid, represented by Formula (5) for inverting the configuration of the αcarbon in the α-amino acid moiety to L-form in cases where the compound represented by Formula (1) is of R-form and to D-form in cases where the compound represented by Formula (1) is of S-form, and subsequently acid decomposing the metal complex to release the chirality-inverted α-amino acid, and thereby give an optically pure α-amino acid enantiomer.

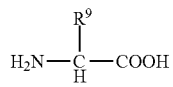

(5)

In Formula (5), $R^9$ denotes an optionally substituted alkyl group (for example, an alkyl group in which a part or all of the hydrogen atoms are replaced with fluorine atoms; the same applies to other substituents, such as an alkynyl group, an alkenyl group, a cycloalkyl group, and an aryl group), an optionally substituted alkynyl group, an optionally substituted alkenyl group, an optionally substituted cycloalkyl group, an optionally substituted aryl group, an optionally substituted heteroaryl group, an optionally substituted aralkyl group, or an optionally substituted heteroarylalkyl group.

[8] The method according to the above [7], wherein the α-amino acid represented by Formula (5) before chirality conversion is a mixture of optical isomers or a pure optical isomer.

[9] The method according to the above [7] or [8], wherein the N-(2-acylaryl)-2-[5,7-dihydro-6H-dibenzo[c,e]azepin-6-yl] acetamide compound is the compound represented by Formula (1) in the above [1].

The reaction chart of the present invention is as follows.

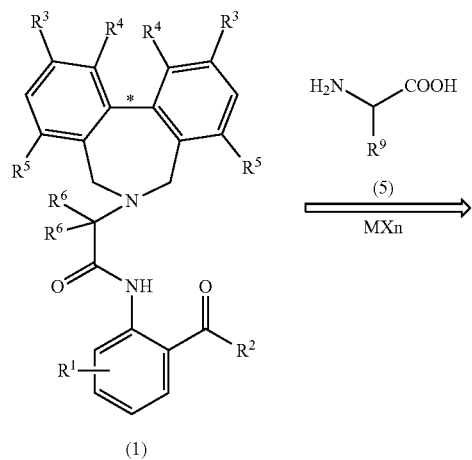

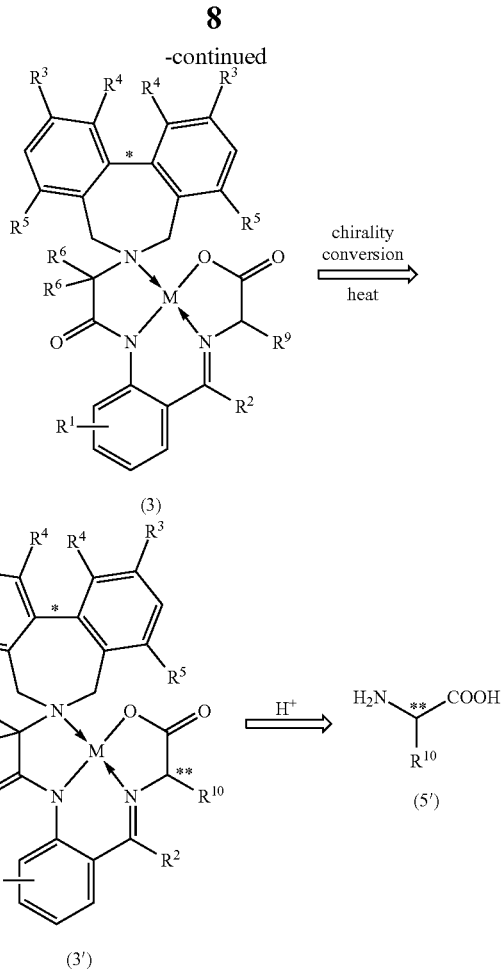

Advantageous Effects of Invention

An object of the present invention is to produce an optically active α-amino acid having a desired chirality in high yield and in a highly enantioselective manner by chirality conversion of an α-amino acid, and the present invention provides, among others, a novel N-(2-acylaryl)-2-[5,7- dihydro-6H-dibenzo[c,e]azepin-6-yl]ac etamide compound as an indispensable chiral template used for the production. The present invention relates to a metal complex of a condensate of an α-amino acid and an optically active N-(2-acylaryl)-2-[5,7-dihydro-6H-dibenzo[c,e]azepin-6-yl] ac etamide compound having axial chirality. Through the intermediary of the above metal complex, the chirality interconversion of an α-amino acid is easily performed, and thereby an α-amino acid having a desired chirality can be produced in a convenient and inexpensive manner.

DESCRIPTION OF EMBODIMENTS

Figure 1:
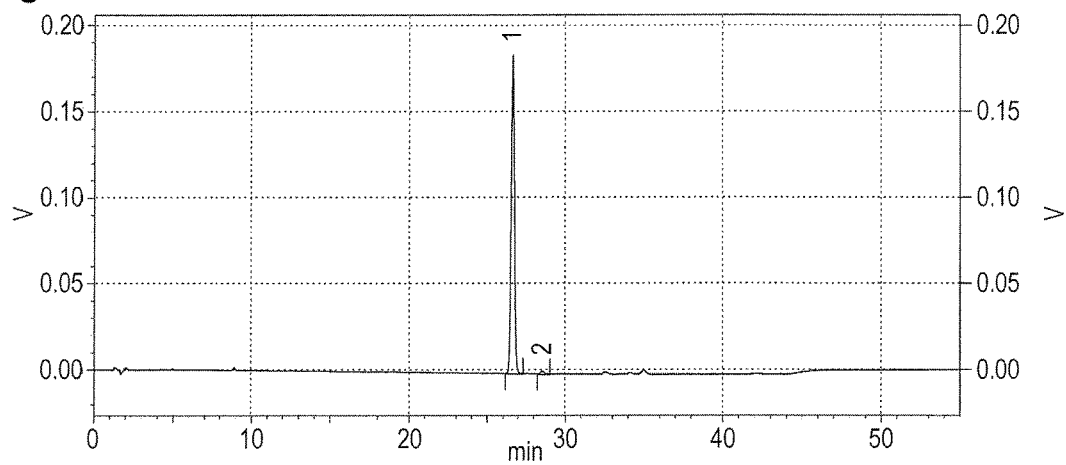
FIG. 1 shows a HPLC analysis result of a Ni (II) complex obtained in Example 2-1, which has D-phenylalanine as a partial structure.

The chemical reactions involved in the present invention are as follows. (Indication of salts is omitted.)

(i) An imine compound produced by condensation of an optically active N-(2-acylaryl)-2-[5,7-dihydro-6H-dibenzo[c,e]azepin-6-yl]ac etamide compound represented by Formula (1) and an α-amino acid represented by Formula (5) is reacted with a metal salt MXn to give a metal complex represented by Formula (3);

(ii.) the metal complex represented by Formula (3) is heated under basic conditions to be led into a metal complex having stereochemically converted configuration of the α-amino acid moiety, which metal complex is represented by Formula (3'); and (iii) the metal complex represented by Formula (3') having stereochemically converted configuration is subjected to acid decomposition to give the α-amino acid having a desired configuration through chirality conversion represented by Formula (5').

The above steps of (i) and (ii) can be performed continuously.

The compound represented by Formula (1) has two optical isomers represented by Formula (1A, S-isomer) and Formula (1B, R-isomer). In the method of the present invention, the optical isomer represented by Formula (1A, S-isomer) converts an L-form α-amino acid into a D-form counterpart but does not change the configuration of the α carbon atom in a D-form α-amino acid. Meanwhile, in the method, of the present invention, the optical isomer represented by Formula (1B, R-isomer) converts a D-form α-amino acid into an L-form counterpart but does not change the configuration of the α carbon atom in an L-form α-amino acid.

That is, the present invention includes a method for converting an L-form α-amino acid into a D-form counterpart, a method for converting a D-form α-amino acid into an L-form counterpart, and a method for completely converting a racemic α-amino acid into an optically pure α-amino acid having single chirality at the α carbon, by using an appropriately selected optical isomer represented by Formula (1A, S-isomer) or Formula (1B, R-isomer).

In the present invention, "pure" means an industrially acceptable level of optical purity. The optical purity is not particularly limited, but usually about 90% or more, preferably about 95% or more.

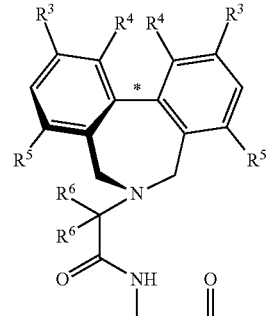

(1A, S-isomer)

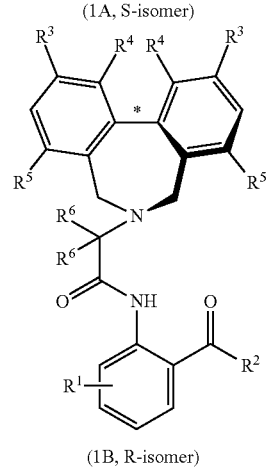

(1B, R-isomer)

The α-amino acid used in the present invention may be L-form, D-form, or a mixture thereof at any ratio, and is preferably an α-amino acid represented by Formula (5):

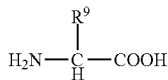

(5)

or a salt thereof. $R^9$ may be an optionally substituted alkyl group (for example, an alkyl group in which a part or all of the hydrogen atoms are replaced with fluorine atoms; the same applies to other substituents, such as an alkynyl group, an alkenyl group, a cycloalkyl group, and an aryl group), an optionally substituted alkynyl group, an optionally substituted alkenyl group, an optionally substituted cycloalkyl group, an optionally substituted aryl group, an optionally substituted heteroaryl group, an optionally substituted aralkyl group, or an optionally substituted heteroarylalkyl group.

According to the method of the present invention, a desired optically active amino acid can be produced in high yield and in a highly enantioselective manner.

The optically active N—(2-acylaryl)-2-[5, 7-dihydro-6H-dibenzo [c,e] azepin-6—yl]ac etamide compound used in the present invention is represented by the following Formula (1):

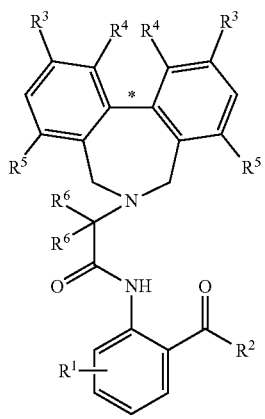

(1)

(wherein $R^1$ denotes hydrogen, an optionally substituted alkyl group (for example, an alkyl group in which a part or all of the hydrogen atoms are replaced with fluorine atoms), an optionally substituted alkynyl group, an optionally substituted alkenyl group, an optionally substituted alkoxy group, an optionally substituted cycloalkyl group, an optionally substituted aryl group, an optionally substituted heteroaryl group, a halogen atom, or a nitro group;

$R^2$ denotes hydrogen, an optionally substituted alkyl group, an optionally substituted alkynyl group, an optionally substituted alkenyl group, an optionally substituted cycloalkyl group, an optionally substituted aryl group, or an optionally substituted heteroaryl group, $R^3$ and $R^4$ each independently denote hydrogen, an optionally substituted alkyl group (for example, an alkyl group in which a part or all of the hydrogen atoms are replaced with fluorine atoms), an optionally substituted alkynyl group, an optionally substituted alkenyl group, an optionally substituted alkoxy group, an optionally substituted cycloalkyl group, an optionally substituted aryl group, an optionally substituted heteroaryl group, or a halogen atom;

the two $R^3$s may be the same or different;
the two $R^4$s may be the same or different;
$R^3$ and $R^4$ may form a ring together with the carbon atoms to which they are bonded;

$R^5$ denotes hydrogen, an optionally substituted alkyl group (for example, an alkyl group in which a part or all of the hydrogen atoms are replaced with fluorine atoms), an optionally substituted alkynyl group, an optionally substituted alkenyl group, an optionally substituted alkoxy group, an optionally substituted cycloalkyl group, an optionally substituted aryl group, an optionally substituted heteroaryl group, a carboxyl group, a halogen atom, —$COOR^7$, or —$C(OH)(R^7)_2$;

the two $R^5$s may be the same or different;
$R^6$ denotes hydrogen, an optionally substituted alkyl group, an optionally substituted cycloalkyl group, or a halogen atom;

the two $R^6$may be the same or different;
the two $R^6$s may form, a ring together with the carbon atom to which they are bonded;

$R^7$ denotes hydrogen, an optionally substituted alkyl group, an optionally substituted aryl group, or an optionally substituted heteroaryl group; and

* denotes a chiral axis).

The "alkyl group" in the optionally substituted alkyl group denoted by $R^1$ is not particularly limited and may be linear or branched. Examples of the "alkyl group" include alkyl groups having 1 to 20 carbon atoms, specifically, a methyl group, an ethyl group, a propyl group, an isopropyl group, a butyl group, an isobutyl group, a sec-butyl group, a tert-butyl group, a pentyl group, an hexyl group, a heptyl group, an octyl group, a nonyl group, a decyl group, a dodecyl group, a pentadecyl group, a hexadecyl group, an octadecyl group, and the like.

The "alkynyl group" in the optionally substituted alkynyl group denoted by R is not particularly limited. Examples of the "alkynyl group" include alkynyl groups having 2 to 20 carbon atoms, specifically, an ethynyl group, a propynyl group, and the like.

The "alkenyl group" in the optionally substituted alkenyl group denoted by $R^1$ is not particularly limited. Examples of the "alkenyl group" include alkenyl groups having 2 to 20 carbon atoms, specifically, a vinyl group, an allyl group, a butenyl group, a hexenyl group, and the like.

The "alkoxy group" in the optionally substituted alkoxy group denoted by $R^1$ is not particularly limited. Examples of the "alkoxy group" include alkoxy groups having 1 to 20 carbon atoms, specifically, a methoxy group, an ethoxy group, a propoxy group, an isopropoxy group, a butoxy group, an isobutoxy group, a sec-butoxy group, a tert-butoxy group, a pentyloxy group, and the like.

The "cycloalkyl group" in the optionally substituted cycloalkyl group denoted by $R^1$ is not particularly limited. Examples of the "cycloalkyl group" include cycloalkyl groups having 3 to 12 carbon atoms, specifically, a cyclopropyl group, a cyclobutyl group, a cyclopentyl group, a cyclohexyl group, a cycloheptyl group, and the like.

The "aryl group" in the optionally substituted aryl group denoted by $R^1$ is not particularly limited. Examples of the "aryl group" include aryl groups having 6 to 20 carbon atoms, specifically, a phenyl group, a 1-naphthyl group, a 2-naphthyl group, an anthryl group, a phenanthryl group, a 2-biphenyl group, a 3-biphenyl group, a 4-biphenyl group, a terphenyl group, and the like.

The "heteroaryl group" in the optionally substituted heteroaryl group denoted by $R^1$ is not particularly limited. Examples of the "heteroaryl group" include heteroaryl groups having 1 to 3 heteroatoms selected from a nitrogen atom, a sulfur atom, an oxygen atom, etc., specifically, a furanyl group, a thienyl group, an oxazolyl group, an isoxazolyl group, a thiazolyl group, an isothiazolyl group, a pyrrolyl group, an imidazolyl group, a pyrazolyl group, a pyridyl group, a pyrimidinyl group, a pyrazinyl group, a phthalazinyl group, a triazinyl group, an indolyl group, an isoindolyl group, a quinolinyl group, an isoguinolinyl group, a dibenzofuraoyl group, and the like.

The halogen atom denoted by $R^1$ is not particularly limited. Examples of the halogen atom include a fluorine atom, a chlorine atom, a bromine atom, an iodine atom, and the like.

The "substituent" in $R^1$ is not particularly limited. Examples of the above "substituent" include an alkyl group (for example, a methyl group, an ethyl group, a propyl group, an isopropyl group, a butyl group, an isobutyl group, a sec-butyl group, a tert-butyl group, a pentyl group, an hexyl group, and the like); an alkynyl group (for example, an ethynyl group, a propynyl group and the like); an alkenyl group (for example, a vinyl group, an allyl group, a butenyl group, a hexenyl group, and the like); an alkoxy group (for example, a methoxy group, an ethoxy group, a propoxy group, an isopropoxy group, a butoxy group, an isobutoxy group, a sec-butoxy group, a tert-butoxy group, a pentyloxy group, and the like); a cycloalkyl group (for example, a cyclopropyl group, a cyclobutyl group, a cyclopentyl group, a cyolohexyl group, a cycloheptyl group, and the like); an aryl group (for example, a phenyl group, a 1-naphthyl group, a 2-naphthyl group, an anthryl group, a phenanthryl group, a 2-biphenyl group, a 3-biphenyl group, a 4-biphenyl group, a terphenyl group, and the like); a heteroaryl group (for example, a furanyl group, a thienyl group, an oxazolyl group, an isoxazolyl group, a thiazolyl group, an isothiazolyl group, a pyrrolyl group, an imidazolyl group, a pyrazolyl group, a pyridyl group, a pyrimidinyl group, a pyrazinyl group, a phthalazinyl group, a triazinyl group, an indolyl group, an isoindolyl group, a quinolinyl group, an isoquinolinyl group, a dibenzofuranyl group, and the like); an aralkyl group (for example, a phenylethyl group, a phenylpropyl group, a naphthyl methyl group, and the like); a haloalkyl group (for example, a trifluoromethyl group, a trichloromethyl group, and the like); a halogenated alkoxy group (for example, a fluoromethoxy group, a difluoromethoxy group, a trifluoromethoxy group, a trifluoroethoxy group, a tetrafluoroethoxy group, and the like); a halogen atom (for example, a fluorine atom, a chlorine atom, a bromine atom, an iodine atom, and the like); a hydroxyl group; a protected hydroxyl group (examples of the protecting group for the hydroxyl group include an acetyl group, a benzoyl group, a methoxymethyl group, a tetrahydropyranyl group, a trimethylsilyl group, a tert-butyldimetbylsilyl group, a carbonate ester group, and the like); an amino group; a protected amino group (examples of the protecting group for the amino group, include a formyl group, an acetyl group, a benzoyl group, a benzyloxycarbonyl group, a phthaloyl group, a carbamoyl group, a ureido group, a tert-butoxycarbonyl group, a 9-fluorenylmethyloxycarbonyl group, and the like); an arylamino group; a heteroarylamino group; a mercapto group; a nitro group; a nitrile group; a carboxyl group; an alkoxycarbonyl group; and the like. The number of carbon atoms in these substituents is not particularly limited, but preferably 1 to 10.

The number of "substituents" in $R^1$ is not particularly limited. The number of "substituents" in $R^1$ has only to be, for example, 1 to 4, is preferably 1 to 2, and more preferably 1.

The position at which $R^1$ is bonded is not particularly limited. The position at which $R^1$ is bonded may be any of positions 3, 4, 5, and 6, but is preferably position 4.

Examples of the optionally substituted alkyl group, the optionally substituted alkynyl group, the optionally substituted alkenyl group, the optionally substituted cycloalkyl group, the optionally substituted aryl group, or the optionally substituted heteroaryl group, denoted by $R^2$ include those listed for $R^1$, for example. Examples of the substituent in this case include those mentioned above for $R^1$, for example.

Examples of the optionally substituted alkyl group, the optionally substituted alkynyl group, the optionally substituted alkenyl group, the optionally substituted alkoxy group, the optionally substituted cycloalkyl group, the optionally substituted aryl group, or the optionally substituted heteroaryl group, or the halogen, atom, denoted by $R^3$ or $R^4$ include those listed for $R^1$, for example. Examples of the substituent in this case include those mentioned above for $R^1$, for example.

The ring formed of $R^3$ and $R^4$ together with the carbon atoms to which they are bonded is not particularly limited, and may be an alicyclic ring or an aromatic ring. Examples of the above ring include a cycloalkane ring, cycloalkene ring, an aryl ring, a heteroaryl ring, and the like, specifically, cyclopentane, cyclohexane, cyclopentene, cyclohexene, a benzene ring, a naphthalene ring, a pyridine ring, and the like. The number of carbon atoms in the above ring is not particularly limited, but preferably 3 to 15.

Examples of the optionally substituted alkyl group, the optionally substituted alkynyl group, the optionally substituted alkenyl group, the optionally substituted alkoxy group, the optionally substituted cycloalkyl group, the optionally substituted aryl group, or the optionally substituted heteroaryl group, or the halogen atom, denoted by $R^6$ include those listed for $R^1$, for example. Examples of the substituent in this case include those mentioned above for $R^1$, for example.

Examples of the optionally substituted alkyl group, the optionally substituted cycloalkyl group, or a halogen atom, denoted by $R^6$ include those listed for $R^1$, for example. Examples of the substituent in this case include those mentioned above for $R^1$, for example.

Examples of the optionally substituted alkyl group, the optionally substituted aryl group, or the optionally substituted heteroaryl group, denoted by $R^7$ include those listed for $R^1$, for example. Examples of the substituent in this case include those mentioned above for $R^1$, for example.

$R^1$ is preferably hydrogen, chlorine, a methyl group, or a nitro group.

$R^2$ is preferably an optionally substituted aryl group, and more preferably a phenyl group, or a phenyl group substituted with a halogen atom.

The two $R^3$s are preferably the same. Also, the two $R^4$s are preferably the same. Also, $R^3$ and $R^4$ more preferably form a ring together with the carbon atoms to which they are bonded.

The two $R^8$s are preferably the same, and more preferably each hydrogen.

The two $R^6$s are preferably the same, and more preferably each hydrogen.

The "chiral axis" herein denoted by * means such a bond axis that restriction of the rotation about the axis produces chirality. The "chiral axis" includes, for example, an axis about which a set of ligands is held in a spatial arrangement that is not superposable on its mirror image and an axis as the line of intersection of two mutually perpendicular planes of a molecule not having a plane of symmetry.

The compound represented by Formula (1) is preferably a compound represented by Formula (2):

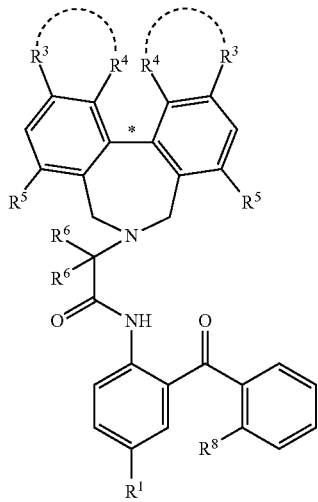

(2)

(wherein $R^1$, $R^5$, $R^6$, and * have the same meanings as defined above, and $R^8$ denotes a hydrogen or halogen atom), wherein $R^3$ and $R^4$ form an aromatic ring or an alicyclic structure together with the carbon atoms to which they are bonded.

Examples of the halogen atom denoted by $R^8$ include halogen atoms listed for $R^1$, for example. $R^8$ is preferably hydrogen, fluorine, or chlorine.

Examples of the compound represented by Formula (2) or a salt thereof include the following compounds represented by Structural Formulae (2-1) to (2-7) or salts thereof, for example.

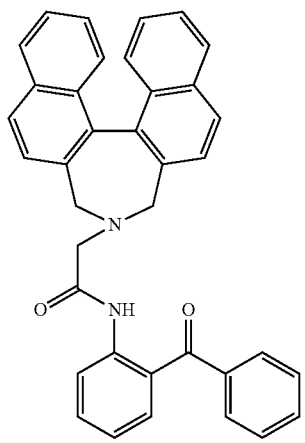

(2-1)

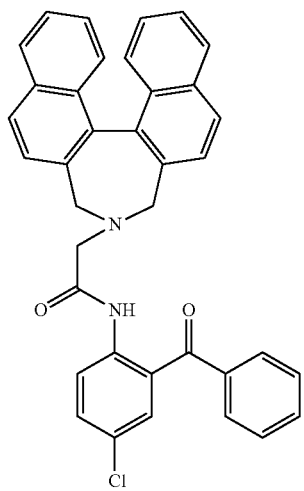

(2-2)

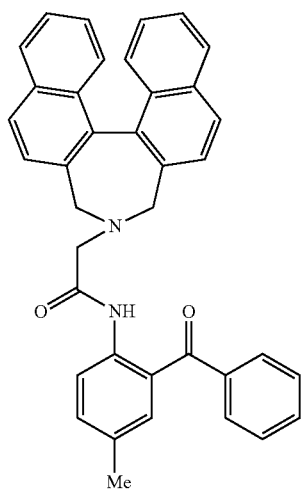

(2-3)

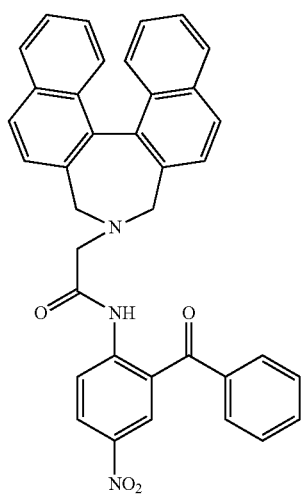

(2-4)

-continued (2-5)
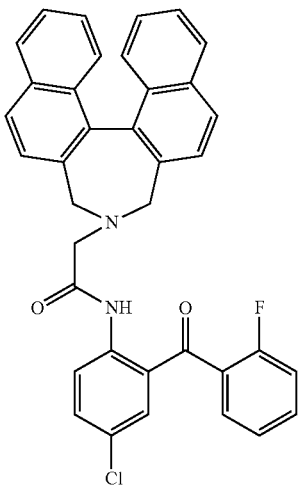

(2-6)
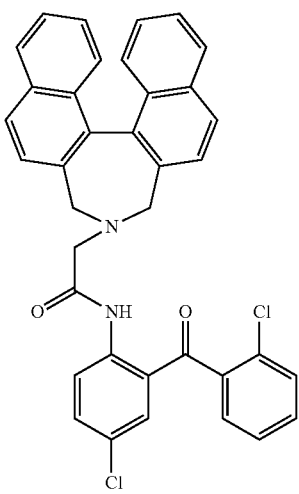

(2-7)
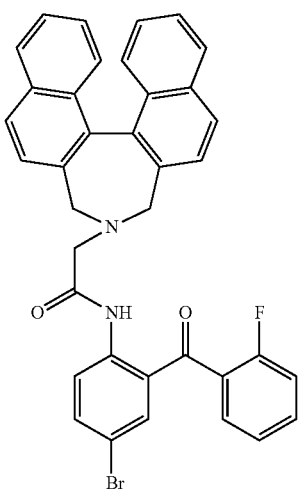

Examples of the salt of the optically active N-(2-acylaryl)-2-[5, 7-dihydro-6H-dibenzo [c,e] azepin-6-yl] acetamide compound in the present invention include a salt with an inorganic acid, such as hydrochloric acid, sulfuric acid, and phosphoric acid; a salt with an organic acid, such as acetic acid and benzenesulfonic acid; etc.

The compound represented by Formula (1) or a salt thereof, of which the production method is not particularly limited, can be produced by the reaction shown below, for example. That is, by the reaction of the compound represented by Formula (7):

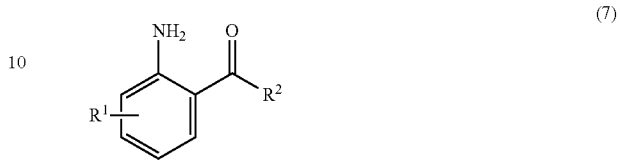
(7)

(wherein $R^1$ and $R^2$ have the same meanings as defined above) or a salt thereof,
the compound represented by Formula (8):

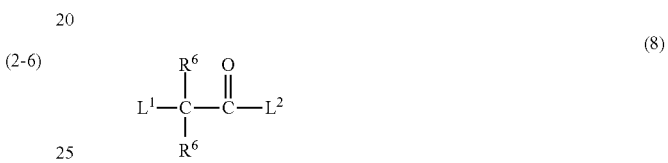
(8)

(wherein $R^6$ has the same meaning as defined above, and $L^1$ and $L^2$ independently denote a leaving group) or a salt thereof, and the compound represented by Formula (9):

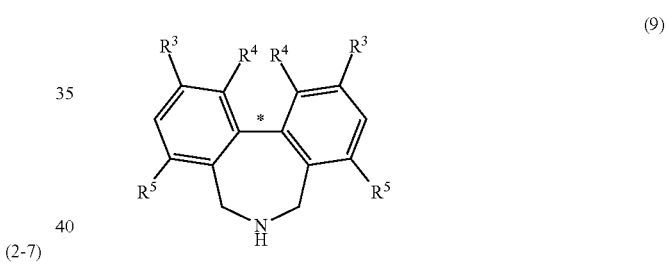
(9)

(wherein $R^3$, $R^4$, $R^5$, and * have the same meanings as defined above) or a salt thereof,
the compound represented by Formula (1) or a salt thereof can be produced.

The compound represented by Formula (7) or a salt thereof may be produced by a known method or be a commercial product.

As the compound represented by Formula (7) or a salt thereof, substances described in a document (T. K. Ellis et al., J. Org. Chem., 2006, 71, 8572-8578), for example, can be used.

The compound represented by Formula (7) is preferably a compound represented by Formula (7-1);

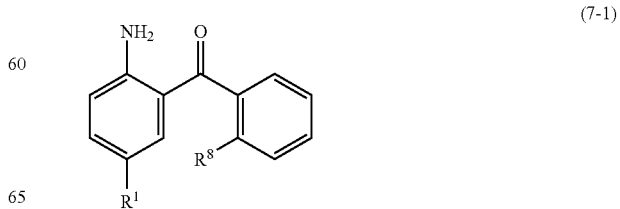
(7-1)

(wherein $R^1$ and $R^8$ have the same meanings as defined above).

In the compound represented by Formula (7-1) or a salt thereof, examples of $R^1$ include those listed for Formula (1), for example. In the compound represented by Formula (7-1) or a salt thereof, examples of $R^8$ include those listed for Formula (2), for example.

In the compound represented by Formula (8):

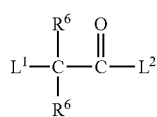

(8)

(wherein $R^6$, $L^1$, and $L^2$ have the same meanings as defined above) or a salt thereof, $L^1$ and $L^2$ independently denote a leaving group. The leaving group is not particularly limited as long as it is a generally known leaving group, and examples thereof include a halogen atom, a tosylate (OTs), and a mesylate (OMs).

$L^1$ and $L^2$ are preferably a halogen atom, and more preferably a chlorine atom or a bromine atom. $L^1$ and $L^2$ are preferably the same group as each other, and more preferably each a halogen atom.

Examples of the compound represented by Formula (8) include $ClCH_2COCl$, $BrCH_2COBr$, etc.

The compound represented by Formula (8) or a salt thereof can be produced by a known method. As an acetanilide compound derived from the compound represented by Formula (8), substances described in a document (T. K. Ellis et al., J. Org. Chem., 2006, 71, 6572-8578), for example, can be used.

The compound represented by Formula (9) or a salt thereof can be produced by a known method. The compound represented by Formula (9) can be produced by a method described in a document (N. Maigrot et al., J. Org. Chem., 1985, 50, 3916-3918), for example.

The compound represented by Formula (9) is preferably a compound represented by Formula (10):

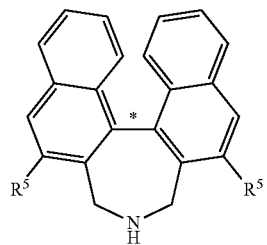

(10)

(wherein $R^5$ and * have the same meanings as defined above).

In the compound represented by Formula (10), examples of $R^5$ and $R^7$ include those listed for Formula (1), for example.

In the above-mentioned production method of the compound represented by Formula (1) or a salt thereof, the conditions for the reaction of the compound represented by Formula (7) or a salt thereof, the compound represented by Formula (8) or a salt thereof, and the compound represented by Formula (9) or a salt thereof is not particularly limited, but preferred are the conditions shown below.

The amount of the compound represented by Formula (8) or a salt thereof used is not particularly limited as long as the reaction proceeds. Specifically, the amount of the compound represented by Formula (8) or a salt thereof used may usually be about 0.5 to 10 mol, more preferably about 1.0 to 3.0 mol, relative to 1 mol of the compound represented by Formula (7) or a salt thereof, for example.

The amount of the compound represented by Formula (9) or a salt thereof used is not particularly limited as long as the reaction proceeds. Specifically, the amount of the compound represented by Formula (9) or a salt thereof used may usually be about 0.5 to 5.0 mol, more preferably about 0.5 to 2.0 mol, relative to 1 mol of the compound represented by Formula (7) or a salt thereof, for example.

(Solvent)

In the above-mentioned production method of the compound represented by Formula (1) or its salt, the solvent used for the reaction is not particularly limited, and examples thereof include organic solvents, such as alcohols (methanol, ethanol, isopropyl alcohol, tert-butanol, etc.); ethers (diethyl ether, tetrahydrofuran, 1,4-dioxane, 1,2-dimethoxyethane, etc.); halohydrocarbons (dichloromethane, chloroform, 1,2-dichloroethane, carbon tetrachloride, etc.); aromatic hydrocarbons (benzene, toluene, xylene, pyridine, etc.); aliphatic hydrocarbons (hexane, pentane, cyclohexane, etc.); nitriles (acetonitrile, propionitrile, etc.); and amides (N,N-dimethylformamide, N,N-dimethylacetamide, and N-methylpyrrolidone). Among these, from the viewpoint of reaction efficiency, preferred are acetonitrile, propionitrile, N,N-dimethylformamide, N,N-dimethylacetamide, N-methylpyrrolidone, etc.

(Base)

In the above-mentioned production method of the compound represented by Formula (1) or its salt, the base used for the reaction is not particularly limited, and examples thereof include potassium hydroxide, sodium hydroxide, lithium hydroxide, sodium hydrogen carbonate, potassium carbonate, sodium carbonate, cesium carbonate, sodium acetate, potassium acetate, lithium acetate, sodium benzoate, lithium benzoate, etc. Among these, from the viewpoint of reaction efficiency, preferred are potassium, hydroxide, sodium hydroxide, lithium hydroxide, potassium carbonate, sodium carbonate, cesium, carbonate, etc.

(Separation and Purification)

In the above-mentioned production method of the compound represented by Formula (1) or its salt, an optically pure objective substance can be obtained by a known separation and/or purification method, which is not particularly limited. Examples of the known separation and/or purification method include, for example, concentration; extraction; filtration; washing; crystallization; recrystallization; formation of a salt with an achiral acid, such as hydrochloric acid, sulfuric acid, methanesulfonic acid, formic acid, trifluoroacetic acid, etc. and recrystallization thereof; and chemical optical resolution using a chiral acid such as mandelic acid, tartaric acid, dibenzoyltartaric acid, ditoluoyltartaric acid, camphor-10-sulfonic acid, and malic acid, a column for optical isomer separation, etc.; and the like.

More specifically, in the above-mentioned production method of the compound represented by Formula (1) or its salt, an additional step of separation and/or purification may be performed to obtain an optically pure objective substance. The separation and/or purification method is not particularly limited, and various methods usually used in this field may be used. Specific examples of the separation method include concentration, extraction, filtration, washing, etc., and specific examples of the purification method include crystallization (recrystallization, suspension, etc.), selective dissolution, physical optical resolution using a column for optical isomer separation, etc., and the like. Examples of the recrystallization include formation of a salt with an achiral acid (hydrochloric acid, sulfuric acid, methanesulfonic acid, formic acid, trifluoroacetic acid, etc.), the diasteteomeric salt formation method using a chiral acid (mandelic acid, tartaric acid, dibensoyltartaric acid, ditoluoyltartaric acid, camphor-10-sulfonic acid, malic acid), and the like.

The metal complex represented by Formula (3) is also a constituent of the present invention.

In the metal complex represented by Formula (3):

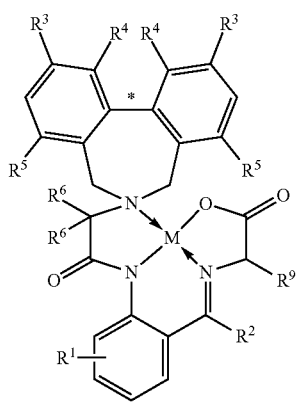

(3)

(wherein $R^1$, $R^2$, $R^3$, $R^4$, $R^5$, $R^6$, and * have the same meanings as defined above;

$R^9$ denotes an optionally substituted alkyl group, an optionally substituted alkynyl group, an optionally substituted alkenyl group, an optionally substituted cycloalkyl group, an optionally substituted aryl group, an optionally substituted heteroaryl group, an optionally substituted aralkyl group, or an optionally substituted heteroarylalkyl group; and M denotes a divalent metallic cation), examples of $R^1$ to $R^6$ include those listed for Formula (1), for example.

In the metal complex represented by Formula (3), M denotes a divalent metallic cation. The divalent metallic cation is not particularly limited, and examples thereof include cations of alkaline earth metals, such as magnesium, calcium, strontium, and barium; cations of transition metals, such as cadmium, titanium, zirconium, nickel (II), palladium, platinum, zinc, copper (II), mercury (II), iron (II), cobalt (II), tin (II), lead (II), and manganese (II); etc. Among them, preferred is a cation of nickel, copper, palladium, or platinum.

In the metal complex represented by Formula (3), examples of the optionally substituted alkyl group, the optionally substituted alkynyl group, the optionally substituted alkenyl group, the optionally substituted cycloalkyl group, the optionally substituted aryl group, or the optionally substituted heteroaryl group, denoted by $R^9$ include those listed for $R^1$, for example.

Examples of the optionally substituted aralkyl group denoted by $R^9$ include the above-mentioned alkyl groups of which a hydrogen atom is replaced by an aryl group, and specific examples thereof include a benzyl group, a phenylethyl group, a phenylpropyl group, a naphthylmethyl group, etc.

Examples of the "heteroaryl group" in the optionally substituted heteroarylalkyl group denoted by $R^9$ include heteroaryl groups having 1 to 3 heteroatoms selected from a nitrogen atom, a sulfur atom, an oxygen atom, etc., and specific examples thereof include a furanyl group, a thienyl group, an oxazolyl group, an isoxazolyl group, a thiazolyl group, an isothiazolyl group, a pyrrolyl group, an imidazolyl group, a pyrasolyl group, a pyridyl group, a pyrimidinyl group, a pyrazinyl group, a phthalazinyl group, a triazinyl group, an indolyl group, an isoindolyl group, a quinolinyl group, an isoquinolinyl group, a dibenzofuranyl group, and the like.

In the metal complex represented by Formula (3), the α-amino acid moiety including $R^3$ has a chiral center. Also, in the metal complex represented by Formula (3), the biphenyl moiety has axial chirality as shown by *.

The metal complex represented by Formula (3) is preferably a metal complex represented by Formula (4);

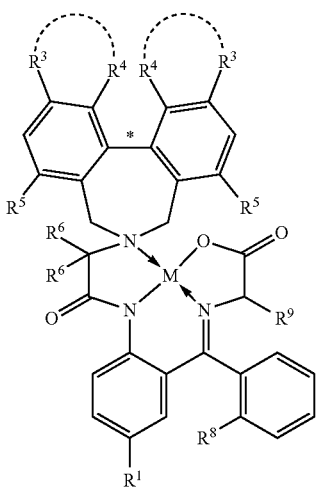

(4)

(wherein $R^1$, $R^5$, $R^6$, $R^8$, $R^9$, M, and * have the same meanings as defined above), wherein $R^3$ and $R^4$ form an aromatic ring or an alicyclic structure together with the carbon atoms to which they are bonded.

In the metal complex represented by Formula (4), examples of $R^1$, $R^5$, and $R^6$ include those listed for Formula (1), for example. Also, in the metal complex represented by Formula (4), examples of $R^9$ and M include those listed for Formula (3), for example. Examples of $R^8$ include those listed for Formula (2), for example.

A preferable production method of the metal complex represented by Formula (3) or Formula (4) will be shown below. That is, by the reaction of an optically active α-amino acid represented by Formula (5):

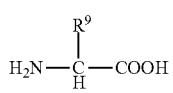

(5)

(wherein $R^9$ has the same meaning as defined above) or a mixture thereof as a raw material, a compound represented by Formula (1):

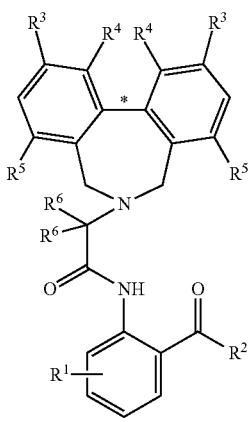

(1)

(wherein each sign has the same meaning as defined for the above Formula (1)) or a salt thereof, and a metal compound represented by Formula (6):

$$MX_n \quad (6)$$

(wherein M denotes a divalent metallic cation; and X denotes a univalent or divalent anion, when X is a univalent anion, n is 2, and when X is a divalent anion, n is 1) in the presence of a base, a metal complex represented by Formula (3);

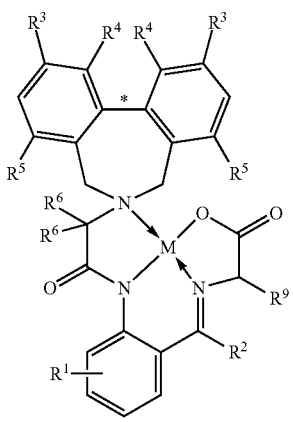

(3)

(wherein each sign has the same meaning as defined for the above Formula (3)) can be obtained.

Examples of the α-amino acid represented by Formula (5) or a salt thereof include α-amino acids, such as alanine (Ala), arginine (Arg), aspsragine (Asn), aspartic acid (Asp), cysteine (Cys), glutamine (Gln), glutamic acid (Glu), histidine (His), isoleucine (Ile), leucine (Leu), lysine (Lys), methionine (Met), phenylalanine (Phe), serine (Ser), threonine (Thr), tryptophan (Trp), tyrosine (Tyr), valine (Val), etc. and unnatural synthetic α-amino acids, and salts thereof. These α-amino acids or salts thereof may be L-form, D-form, or mixtures thereof at any ratio.

In the above production method, after the α-amino acid represented by Formula (5) or a salt thereof as a raw material, the compound represented by Formula (1) or a salt thereof, and the metal compound represented by Formula (6) or a salt thereof, were mixed, the mixture is preferably heated. As a result, the metal, complex represented by Formula (3) as the objective substance can be obtained in higher yield.

The solvent used in the production of the metal complex is an alcohol, and is preferably methanol, ethanol, isopropyl alcohol, tert-butanol, or fert-amyl alcohol. The amount of the solvent used is not particularly limited, and is usually about 1.0 to 150 parts by volume, preferably about 5 to 50 parts by volume, relative to 1 part by weight of the compound represented by Formula (1).

The amount of the α-amino acid represented by Formula (5) or a salt thereof used is not particularly limited. The amount of the α-amino acid represented by Formula (5) or a salt thereof used may usually be about 0.1 to 10 mol, more preferably about 0.3 to 5 mol, relative to 1 mol of the compound represented by Formula (1) or a salt thereof.

The amount of the metal compound represented by Formula (6) used is not particularly limited. The amount of the metal compound represented by Formula (6) used may usually be about 0.1 to 10 mol, more preferably about 0.5 to 8.0 mol, relative to 1 mol of the compound represented, by Formula (1) or a salt thereof.

Examples of the base used, in the above production method include those described for the reaction of the compound represented by Formula (7) or a salt thereof, the compound represented by Formula (8) or a salt thereof, and the compound represented by Formula (9) or a salt thereof. Among these, preferred are potassium carbonate, sodium carbonate, cesium carbonate, potassium hydroxide, sodium hydroxide, and lithium hydroxide.

The amount of the base used is not particularly limited. The amount of the base used may usually be about 0.1 to 20 mol, preferably 0.5 to 10 mol, relative to 1 mol of the compound represented by Formula (1).

In the above-described production method, the reaction time of the present invention is not particularly limited. The reaction time is usually about 0.1 to 72 hours, preferably 0.1 to 48 hours, and particularly preferably 0.1 to 20 hours.

In the above production method, the pressure for the reaction is not particularly limited, and the reaction may be performed under any condition of atmospheric pressure, increased pressure, and reduced pressure. The pressure for the above reaction may usually be about 0.1 to 10 atmospheres. In this metal complex formation reaction, the configuration of the α carbon in the amino-acid moiety of the metal complex (3) is easily interconverted by heating. Therefore, the metal complex (3) may be once isolated and then heated for interconversion of the configuration of the α carbon. Alternatively, the interconversion of the configuration of the α carbon may be performed, by heating at the time of the metal complex formation.

By heating the above-produced metal complex (3) in a solvent under basic conditions, the configuration of the α-amino acid moiety including $R^9$ is chirality-converted to give a metal complex represented by Formula (3'):

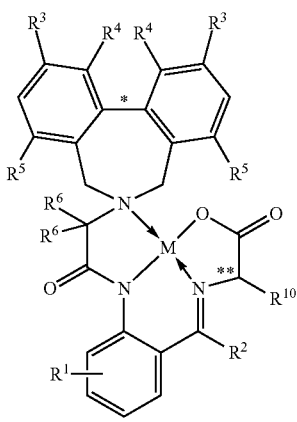

(3')

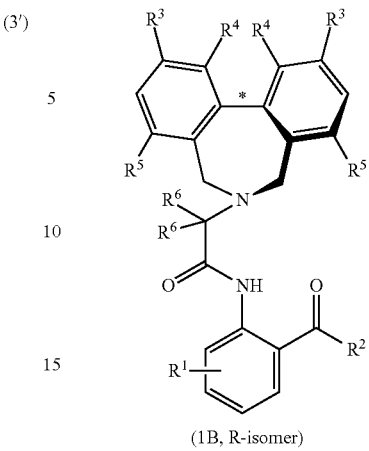

(1B, R-isomer)

(wherein each sign has the same meaning as defined for the above Formula (3); $R^{10}$ has the same meaning as the above $R^9$; and ** denotes an asymmetric carbon atom).

That is, when the compound represented by Formula (1) or a salt thereof is an optical isomer represented by Formula (1A, S-isomer):

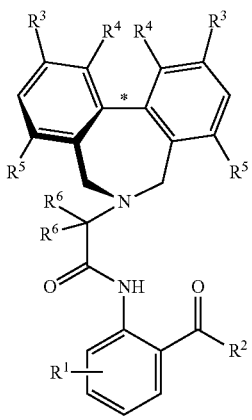

(1A, S-isomer)

(wherein $R^1$, $R^2$, $R^3$, $R^4$, $R^5$, $R^6$, and * have the same meanings as defined above) or a salt thereof and the α-amino acid represented by Formula (5) or a salt thereof as a raw material is an optical isomer of L-form, the chirality of the α-amino acid moiety of the produced metal complex represented by Formula (3) is converted to D-form by heating under basic conditions, but when the α-amino acid represented by Formula (5) or a salt thereof as a raw material has a D-form configuration, the configuration of the α-amino acid moiety of the produced metal complex represented by Formula (3) is not changed and remains in D-form.

Also, when the compound represented by Formula (1) or a salt thereof is an optical isomer represented by Formula (1B, R-isomer):

(wherein $R^1$, $R^2$, $R^3$, $R^4$, $R^5$, $R^6$, and * have the same meanings as defined above) or a salt thereof and the α-amino acid represented by Formula (5) or a salt thereof as a raw material is an optical isomer of D-form, the chirality of the α-amino acid moiety of the produced metal complex represented by Formula (3) is converted to L-form by heating under basic conditions, but when the α-amino acid represented by Formula (5) or a salt thereof as a raw material has an L-form configuration, the configuration of the α-amino acid moiety of the produced metal complex represented by Formula (3) is not changed and remains in L-form.

Thus, the production method is characterized in that, by using an appropriately selected optical isomer of an N—(2-acylaryl)-2-[5, 7-dihydro-6H-dibenzo [c,e] azepin-6-yl]ac etamide compound, the configuration of the α-amino, acid moiety is converted. That is, the production method include a method for producing, by using an α-amino acid represented by Formula (5) having a configuration of L-form as a raw material, a metal complex represented by Formula (3') in which the configuration of the α-carbon in the α-amino acid moiety including $R^{10}$ is converted to D-form; and a method for producing, by using an α-amino acid represented by Formula (5) having a configuration of D-form as a raw material, a metal complex represented by Formula (3') in which the configuration of the α-carbon in the α-amino acid moiety including $R^{10}$ is converted to L-form.

Further, in the production method, by using an appropriately selected optical isomer of an N-(2-acylaryl)-2-[5, 7-dihydro-6H-dibenzo [c,e] azepin-6-yl] acetamide compound and by using a racemic mixture of an α-amino acid represented by Formula (5) as a raw material, a metal complex represented by Formula (3') in which the configuration of the α-amino acid moiety including $R^{10}$ is converted to either L-form or D-form can be produced.

The solvent used in the chirality conversion is an alcohol or the like, and is preferably methanol, ethanol, isopropyl alcohol, tert-butanol, tert-amyl alcohol or methyl isobutyl ketone. The amount of the solvent used is not particularly limited, and is usually about 1.0 to 150 parts by volume, preferably about 5 to 50 parts by volume, relative to 1 part by weight of the compound represented by Formula (1).

In the chirality interconversion, the configuration of the a carbon in the α-amino-acid moiety of the metal complex represented by Formula (3) is converted by heating an alcohol solution of the metal complex usually at about 40 to 80° C. for about 0.5 to 24 hours.

The pressure for the reaction is not particularly limited, and the reaction may be performed under any condition of atmospheric pressure, increased pressure, and reduced pressure. The pressure for the above reaction may usually be about 0.1 to 10 atmospheres.

(Separation and Purification)

In the above-described production method, an optically pure objective substance can be obtained, by performing a known separation and/or purification method after the reaction. Examples of the means therefor include solvent exchange, concentration, chromatography, crystallization, distillation, etc., for example.

Next, a method of acid decomposition for releasing a chiral α-amino acid represented by Formula (5' ) from the metal complex represented by Formula (3') in which the chirality of the α-amino acid moiety has been converted will be described below. The metal complex represented by Formula (3'):

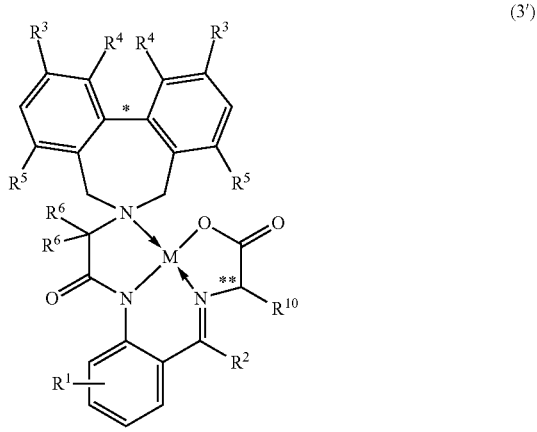

(3')

(wherein each sign has the same meaning as defined for the above Formula (3); $R^{10}$ has the same meaning as the above $R^9$; and ** denotes an asymmetric carbon atom) in which the chirality of the α-amino acid moiety has been converted is reacted with an acid for acid decomposition, of the compound represented by Formula (3' ) or a salt thereof, an α-amino acid represented by Formula (5'):

(5')

(wherein $R^{10}$ has the same meaning as the above $R^9$; ** denotes an asymmetric carbon atom; and the configuration of the α carbon is converted from the compound represented by Formula (5)) having a desired chirality or a salt thereof can be produced.

The configuration of the α-amino acid represented by Formula (5') or a salt thereof is the same as that of the α-amino acid moiety of the metal complex represented by Formula (3').

The acid used for the above-described production method is not particularly limited, and any known acid may be used. The acid may be an inorganic acid or an organic acid. Examples of the inorganic acid include hydrochloric acid, nitric acid, sulfuric acid, perchloric acid, etc. Examples of the organic acid include acetic acid, trifluoroacetic acid, methanesulfonic acid, triflacromethanesulfonic acid, oxalic acid, propionic acid, butanoic acid, valeric acid, etc. Preferred are hydrochloric acid, sulfuric acid, trifluoroacetic acid, and methanesulfonic acid, and more preferred are hydrochloric acid and methanesulfonic acid.

Preferable reaction conditions for the acid decomposition of the metal complex represented by Formula (3') will be shown below.

The amount of the acid used is not particularly limited. The amount of the acid used may usually be about 0.1 to 20 mol, preferably about 0.3 to 10 mol, relative to 1 mol of the metal complex represented by Formula (3'), for example.

The solvent used in the production method is preferably an alcohol, and is more preferably methanol or ethanol. The amount of the solvent used may usually be about 0.1 to 100 parts by volume, preferably 0.5 to 50 parts by volume, relative to 1 part by weight of the metal complex represented by Formula (3'), for example.

In the above-described production method, the reaction temperature is usually about 0 to 100° C., preferably 0 to 80° C., more preferably 5 to 60° C., and particularly preferably 40 to 60° C.

In the above-described production method, the reaction time is usually about 0.1 to 72 hours, preferably about 0.1 to 48 hours, and particularly preferably about 0.1 to 20 hours.

The pressure for the above reaction is not particularly limited, and may be about 0.1 to 10 atmospheres, for example.

(Separation and Purification)

In the above-described production method, an optically pure objective substance can be obtained by performing a known separation and/or purification method after the reaction.

(Product)

By the above production method, an α-amino acid represented by Formula (5'):

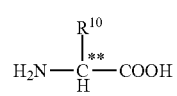

(5')

(wherein each sign has the same meaning as defined for the above Formula (5')) having any chirality or a salt thereof can be produced. Examples of the α-amino acid represented by Formula (5') include those listed for the above Formula (5), for example. However, the configuration of the a carbon of the α-amino acid represented by Formula (5') or a salt thereof is converted from the α-amino acid represented by Formula (5) or a salt thereof.

EXAMPLES (HPLC Measurement Conditions)

In Examples and Reference Examples, measurements were made under the following HPLC conditions.
<HPLC Conditions-1: Complex Analysis Conditions>
Column: Inertsil™ ODS-3 (3 μm, 150×4.6 mm i.d.)
Eluent: A:B=40:60 to 20:80 (0 to 25 min) and 20:80 (25 min to 45 min)
A=10 mM ammonium formate in 0.1% formic acid buffer solution
B=acetonitrile
Flow rate: 1.0 mL/min
Temp: 40° C.
Detector: UV 254 nm <HPLC Conditions-2: Z-Phe Chiral Analysis Conditions 1>
Column; CHIRALCELL OJ-RH (5 μm, 150×4.6 mm i.d.)
Eluent: A:B=65:35 (0 to 30 min)
    A=0.1% phosphoric acid aqueous solution
    B=acetonitrile containing 0.1% phosphoric acid
Flow rate: 0.5 mL/min
Temp: 35° C.
Detector: UV 200 nm
<HPLC Conditions-2': Z-Phe Chiral Analysis Conditions 2>
Column: CHIRALCELL OJ-RH (5 μm, 150×4.6 mm i.d.)
Eluent: A:B=65:35 (0 to 30 min)
    A=0.1% phosphoric acid, aqueous solution
    B=acetonitrile containing 0.1% phosphoric acid
Flow rate: 0.5 mL/min
Temp: 35° C.
Detector: UV 254 nm
<HPLC Conditions-3: Gln Complex Analysis Conditions>
Column; Inertsil™ ODS-3 (3 μm, 150×4.6 mm i.d.)
Eluent: A:B=40:60 (0 to 40 min) and 10:90 (41 min to 50 min)
    A=10 mM ammonium formate in 0.1% formic acid buffer solution
    B=acetonitrile
Flow rate: 0.5 mL/min
Temp: 40° C.
Detector: UV 254 nm
<HPLC Conditions-4: Z-D-Lys (Z) Chiral Analysis Conditions>
Column: CHIRALPAK AS-RH (5 μm, 150×4.6 mm i.d.)
Eluent: A:B=60:40 (0 to 12 min)
    A=phosphoric acid aqueous solution (pH=2)
    B=acetonitrile
Flow rate: 1.0 mL/min
Temp: 25° C.
Detector: UV 200 nm Example 1

Synthesis of Chiral Template (Chiral Auxiliary)

Example 1-1

Synthesis of (S)-N-(2-benzoylphenyl)-2-[3,5-dihydro-4H-dinaphtho [2,1-c :1',2'-e]azepin-4-yl]acetamide

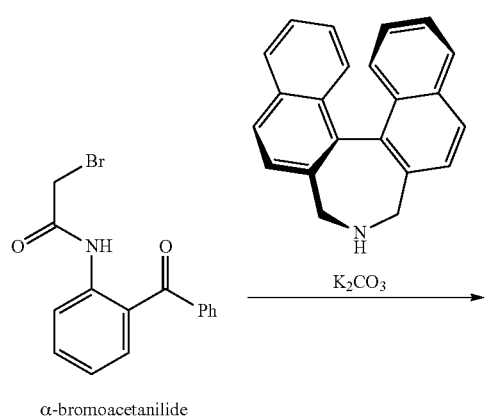

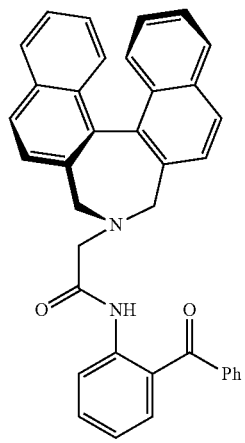

To an acetonitrile solution (40 mL) of N-(2-benzoylphenyl)-2-bromoacetamide (2.0 g, 6.3 mmol), potassium carbonate (1.74 g, 12.58 mmol) and (S)-binaphthyl amine were added. The mixture was heated to 40° C. and stirred for 17 hours. After the end of the reaction, the reaction suspension was concentrated to dryness. The concentrated residue was purified by silica gel chromatography (n-hexane:ethyl acetate=4:1 (v/v)) to give (S)-N-(2-benzoylphenyl)-2-[3,5-dihydro-4H-dinaphtho[2,1-c:1', 2'-e]azepin-4-yl]acetamide P3.14 g, yield: 93.6%, purity: 99.1%) as pale yellow crystals.

ESI-MS (positive mode): m/z=533.3 for [M+H]$^+$ $^1$H-NMR (200 MHz, CDCl$_3$): δ8.10 and 3.57 (1H each, ABq, J=16.7 Hz, COCH$_2$, 3.40 and 3.66 (2H each, ABq, J=12.3 Hz, 2×NCH$_2$), 7.13 (1H, ddd, J=7.9, 7.3, 1.1 Hz, ArH), 7.26 (1H, ddd, J=8.8, 6.4, 1.3Hz, ArH), 7.42-7.63 (12H, m, ArH), 7.74-7.80 (2H, m, ArH), 7.92-7.98 (2H, np ArH), 7.94 (2H, d, J=8.2 Hz, ArH), 8.64 (1H, dd, J=8.4, 0.7 Hz, ArH), 11.59 (1H, br s, NH).

$^{13}$C-NMR (50.3 MHz, CDCl$_3$): δ56.4 (CH$_2$), 60.5 (CH$_2$), 122.0 (ArCH), 122.5 (ArCH), 125.6 (ArCH), 125.8 (ArCH), 127.5 (ArCH), 127.7 (ArCH), 128.3 (ArCH), 128.6 (ArCH), 130.2 (ArCH), 131.5 (quaternary ArC), 132.5 (ArCH), 132.6 (ArCH), 133.2 (quaternary ArC), 133.3 (quaternary ArC), 133.4 (ArCH), 135.0 (quaternary ArC), 138.5 (quaternary ArC), 139.0 (quaternary ArC), 170.2 (CO), 197.8 (CO).

Example 1-2

Synthesis of (S)-N-(2-benzoyl-4-chlorophenyl)-2-[3,5-dihydro-4H-dinaphth o[2,1-c:1', 2'-e]azepin-4-yl]acetamide

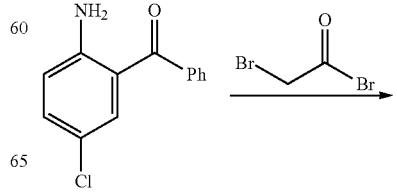

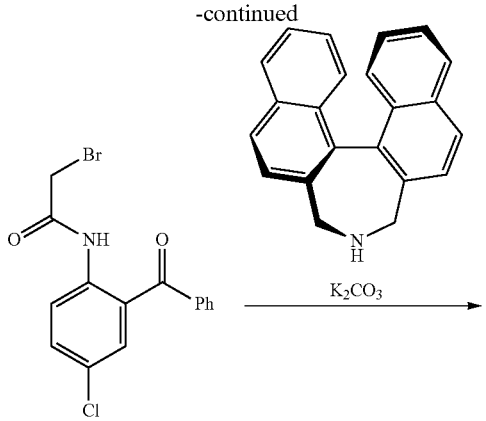

α-bromoacetanilide

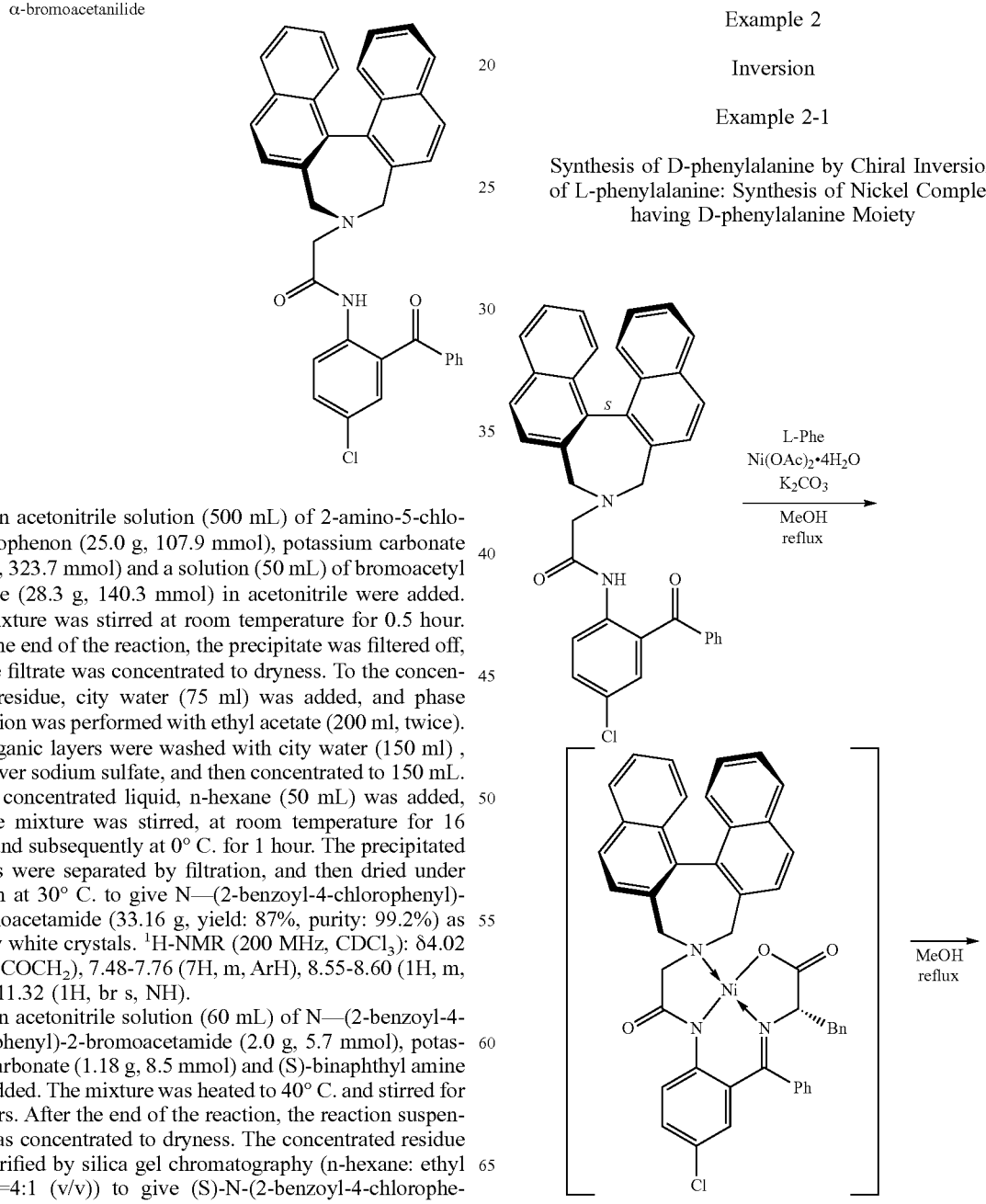

To an acetonitrile solution (500 mL) of 2-amino-5-chlorobenzophenon (25.0 g, 107.9 mmol), potassium carbonate (44.7 g, 323.7 mmol) and a solution (50 mL) of bromoacetyl bromide (28.3 g, 140.3 mmol) in acetonitrile were added. The mixture was stirred at room temperature for 0.5 hour. After the end of the reaction, the precipitate was filtered off, and the filtrate was concentrated to dryness. To the concentrated residue, city water (75 ml) was added, and phase separation was performed with ethyl acetate (200 ml, twice). The organic layers were washed with city water (150 ml), dried over sodium sulfate, and then concentrated to 150 mL. To the concentrated liquid, n-hexane (50 mL) was added, and the mixture was stirred, at room temperature for 16 hours and subsequently at 0° C. for 1 hour. The precipitated crystals were separated by filtration, and then dried under vacuum at 30° C. to give N—(2-benzoyl-4-chlorophenyl)-2-bromoacetamide (33.16 g, yield: 87%, purity: 99.2%) as slightly white crystals. $^1$H-NMR (200 MHz, CDCl$_3$): δ4.02 (2H, s, COCH$_2$), 7.48-7.76 (7H, m, ArH), 8.55-8.60 (1H, m, ArH), 11.32 (1H, br s, NH).

To an acetonitrile solution (60 mL) of N—(2-benzoyl-4-chlorophenyl)-2-bromoacetamide (2.0 g, 5.7 mmol), potassium carbonate (1.18 g, 8.5 mmol) and (S)-binaphthyl amine were added. The mixture was heated to 40° C. and stirred for 16 hours. After the end of the reaction, the reaction suspension was concentrated to dryness. The concentrated residue was purified by silica gel chromatography (n-hexane: ethyl acetate=4:1 (v/v)) to give (S)-N-(2-benzoyl-4-chlorophenyl)-2-[3,5-dihydro-4-dinaphth o[2,1-c: 1',2'-e]azepin-4-yl] acetamide (3.25 g, yield: quantitative, purity: 99.7%, 93.8% ee) as pale yellow crystals.

ESI-MS (positive mode): m/z=567.2 for [M+H]$^+$.

$^1$H-NMR (200 MHz, CDCl$_3$S): δ3.09 and 3.54 (1H each, ABq, J=16.8 Hz, COCH$_2$), 3.39 and 3.61 (2H each, ABq, J=12.1 Hz, 2×NCH$_2$), 7.21-7.30 (2H, m, ArH), 7.42-7.65 (11H, m, ArR), 7.73-7.80 (2H, m, ArH), 7.92-7.98 (2H, m, ArH), 7.94 (2H, d, J=8.2 Hz, ArH), 8.62 (2H, d, J=8.6 Hz, ArH), 11.49 (1H, br s, NH).

$^{13}$C-NMR (50.3 MHz, CDCl$_3$): δ56.4 (CH$_2$), 60.3 (CH$_2$), 123.3 (ArCH), 125.6 (ArCH), 125.9 (ArCH), 126.8 (quaternary ArC), 127.5 (ArCH), 127.6 (ArCH), 127.8 (quaternary ArC), 127.9 (quaternary ArC), 128.3 (ArCH), 128.6 (ArCH), 128.7 (ArCH), 130.2 (ArCH), 131.4 (quaternary ArC), 131.6 (ArCH), 133.1 (ArCH), 133.3 (quaternary ArC), 135.0 (quaternary ArC), 137.4 (quaternary ArC), 137.6 (quaternary ArC), 170.2 (CO), 196.4 (CO).

Example 2

Inversion

Example 2-1

Synthesis of D-phenylalanine by Chiral Inversion of L-phenylalanine: Synthesis of Nickel Complex having D-phenylalanine Moiety

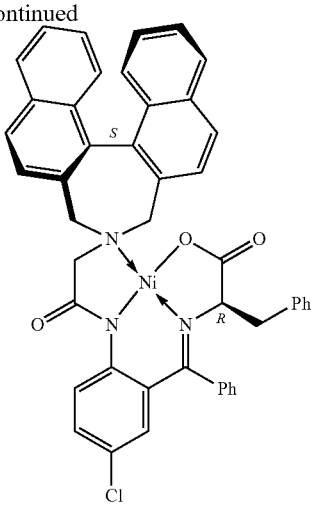
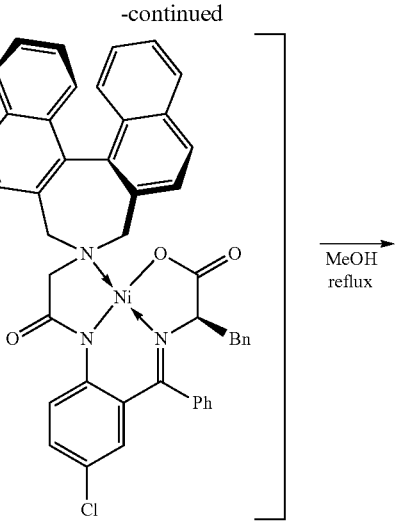

To a methanol suspension (4 mL) of (S)-N-(2-benzoyl-4-chlorophenyl)-2-[3,5-dihydro-4H-dinaphth o[2,1-c:1',2'-e]azepin-4-yl]acetamide (0.2 g, 0.353 mmol), nickel acetate tetrahydrate (0.176 g, 0.706 mmol), L-phenylalanine (0.117 g, 0.706 mmol), and potassium carbonate (0.293 g, 2.118 mmol) were added, and the mixture was refluxed for 24 hours. After the end of the reaction, the reaction mixture was added to an ice-cooled 5% acetic acid aqueous solution (1.5 mL) and stirred for 30 minutes to allow crystals to precipitate. The crystals were separated by filtration, and then blow-dried at 50° C. to give a nickel (II) complex having a D-phenylalanine moiety (0.246 g, yield: 90.5%, 98% de) as red crystals.

The product of this Example was analysed under HPLC conditions-1: complex analysis conditions. The results are shown in FIG. 1.

Example 2-2

Synthesis of L-phenylalanine by Chiral Inversion of D-phenylalanine: Synthesis of Nickel Complex having L-phenylalanine Moiety

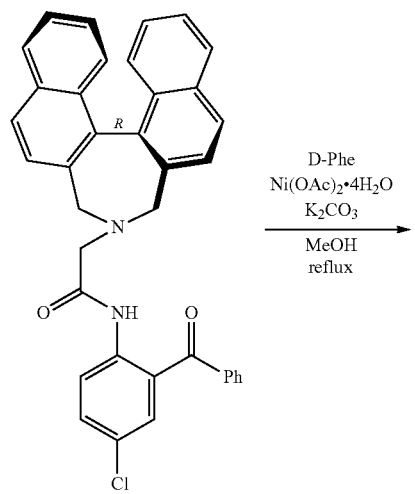

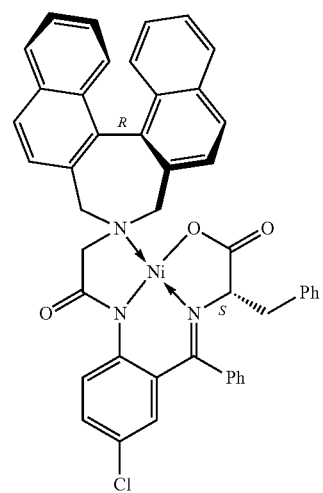

To a methanol suspension (4 mL) of (R)-N-(2-benzoyl-4-chlorophenyl)-2-[3,5-dihydro-4H-dinaphth o[2,1-c:1',2'-e]azepin-4-yl]acetamide (0.4 g, 0.705 mmol), nickel acetate tetrahydrate (0.351 g, 1.411 mmol), D-phenylalanine (0.233 g, 1.411 mmol), and potassium carbonate (0.585 g, 4.232 mmol) were added, and the mixture was refluxed for 24 hours. After the end of the reaction, the reaction mixture was added to an ice-cooled 5% acetic acid aqueous solution (60 mL) and stirred for 30 minutes to allow crystals to precipitate. The crystals were separated by filtration, and then blow-dried at 50° C. to give a nickel (II) complex having an L-phenylalanine moiety (0.493 g, yield: 90.6%, 97% de) as red crystals.

Figure 2:
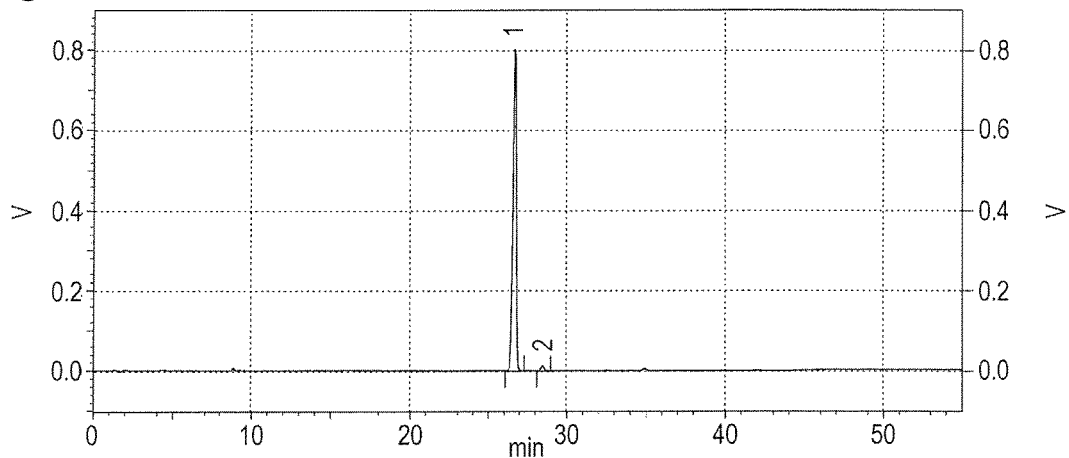
FIG. 2 shows a HPLC analysis result of a Ni (II) complex obtained in Example 2-2, which has L-phenylalanine as a partial structure.

The product of this Example was analyzed under HPLC conditions-1: complex analysis conditions. The results are shown in FIG. 2.

Example 2-3

Synthesis of D-leucine by Chiral Inversion of L-leucine: Synthesis of Nickel Complex having D-leucine Moiety

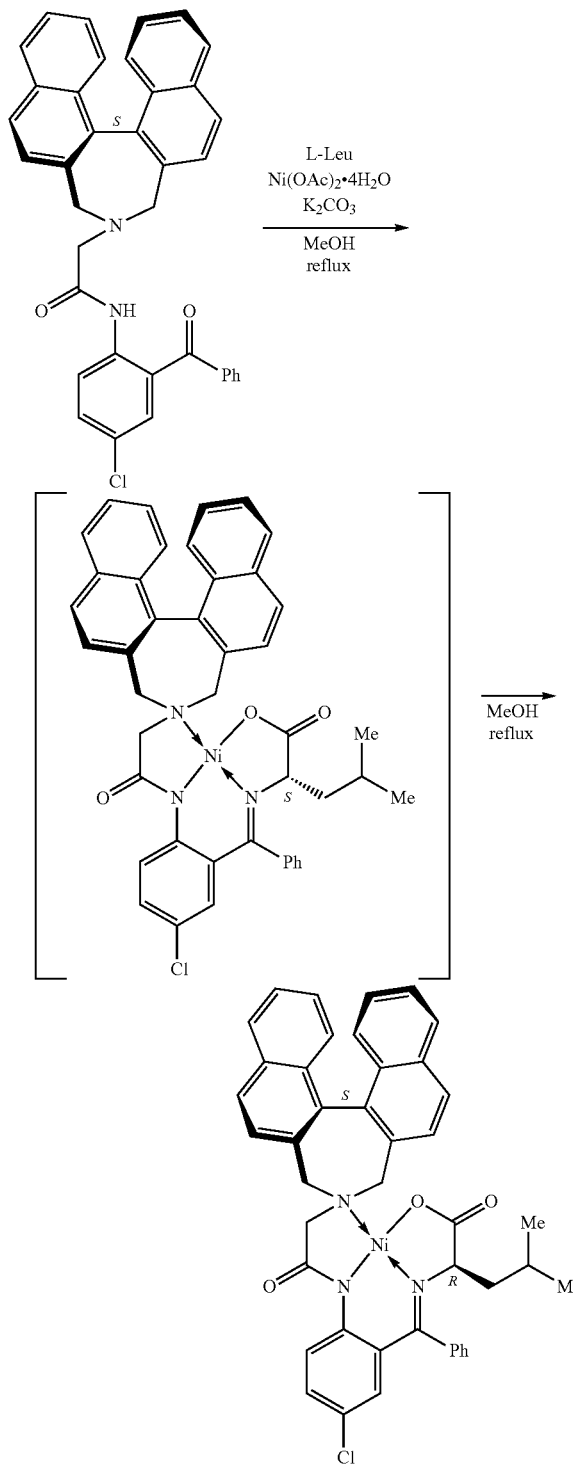

To a methanol suspension (2 mL) of (S)-N-(2-benzoyl-4-chlorophenyl)-2-[3,5-dihydro-4H-dinaphth o[2,1-c: 1',2'-e]azepin-4-yl]acetamide (0.1 g, 0.176 mmol), nickel acetate tetrahydrate (0.046 g, 0.353 mmol), L-leucine (0.046 g, 0.353 mmol), and potassium carbonate (0.146 g, 1.058 mmol) were added, and the mixture was refluxed for 25 hours. After the end of the reaction, the reaction mixture was added to an ice-cooled 5% acetic acid aqueous solution (15 mL) and stirred for 30 minutes to allow crystals to precipitate. The crystals were separated by filtration, and then vacuum-dried at 40° C. to give a nickel (II) complex having a D-leucine moiety (0.116 g, yield: 89.1%, 91.6% de) as red crystals.

ESI-MS (positive mode): m/z=736.3 for [M+H]$^+$.

$^1$H-NMR (200 MHz, CDCl$_3$); δ0.43 (3H, d, J=6.4 Hz, Me), 0.87 (3H, d, J=6.6 Hz, Me), 1.28 (1H, ddd, J=13.3, 10.1, 3.7 Hz, one of β-CH$_2$ of Leu part), 1.88-2.05 (1H, m, CHMe$_2$), 2.34 (1H, ddd, J=13.3, 10.5, 3.5 Hz, one of β-CH$_2$ of Leu part), 2.72 [1H, d, J=12.1 Hz, one of azepine C(α)H$_2$N], 3.07 [1H, d, J=15.6 Hz, one of azepine C (α) H$_2$N], 3.67 and 3.73 (1H each, ABq, J=13.9 Hz, acetanilide NCOCH$_2$), 3.81 (1H, dd, J=10.1, 3.5 Hz, α-H of Leu part), 4.56 [H, d, J=15.6 Hz, one of azepine C(α')H$_2$N], 4.83 [1H, d, J=12.1 Hz, one of azepine C(α) H$_2$N], 6.66 (1H, d, J=2.4 Hz, ArH) , 6.89-6.97 (1H, m, ArH) , 7.18-7.58 (12H, m, ArH), 7.34-8.03 (3H, m, ArH), 8.16 (1H, d, J=8.2 Hz, ArH), 3.42 (1H, d, J=9.2 Hz, ArH), 8.77 (1H, d, J=8.2 Hz, ArH).

$^{13}$C-NMR (50.3 MHz, CDCl$_3$): δ20.8 and 23.8 (2×Me of Leu part), 24.3 (γ-CH of Leu part), 45.4 (β-CH$_2$ of Leu part), 58.3 (NCOCH$_2$), 61.9 and 66.4 (2×CH$_2$ of azepine), 69.4 (α-CH of Leu part), 125.1 (ArCH), 126.1 (quaternary ArC), 126.37 (ArCH), 126.44 (ArCH), 127.3 (ArCH), 127.4 (ArCH), 127.5 (ArCH), 127.8 (ArCH), 127.9 (ArCH), 128.4 (ArCH), 128.66 (ArCH), 128.73 (quaternary ArC), 129.17 (ArCH), 129.24 (ArCH), 129.5 (ArCH), 130.3 (ArCH), 131.0 (quaternary ArC), 131.2 (quaternary ArC), 131.5 (quaternary ArC), 132.4 (ArCH), 132.5 (ArCH), 132.8 (quaternary ArC), 133.7 (quaternary ArC), 134.1 (quaternary ArC), 135.6 (quaternary ArC), 136.0 (quaternary ArC), 140.9 (quaternary ArC), 169.5, 174.6, 178.5 (CN and 2×CO).

Figure 3:
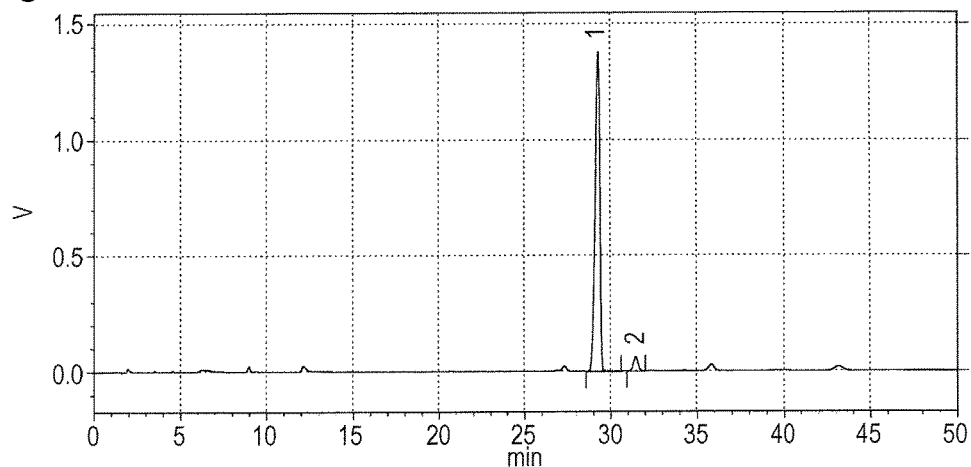
FIG. 3 shows a HPLC analysis result of a Ni (II) complex obtained in Example 2-3, which has D-leucine as a partial structure.

The product of this Example was analyzed under HPLC conditions-1: complex analysis conditions. The results are shown in FIG. 3.

Example 2-4

Synthesis of D-methionine by Chiral Inversion of L-methionine: Synthesis of Nickel Complex having D-methionine Moiety

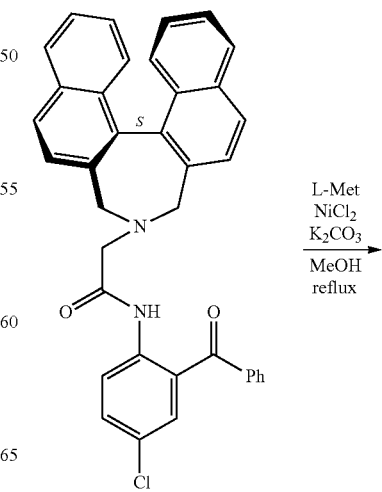

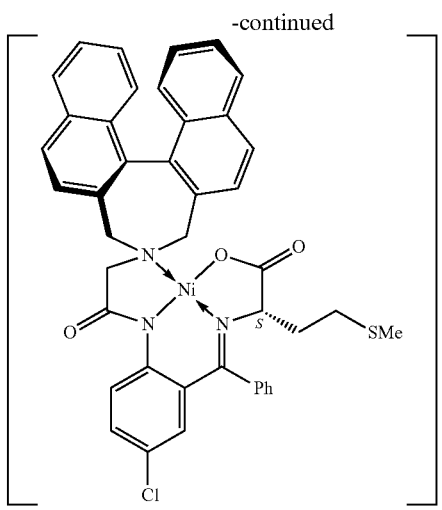

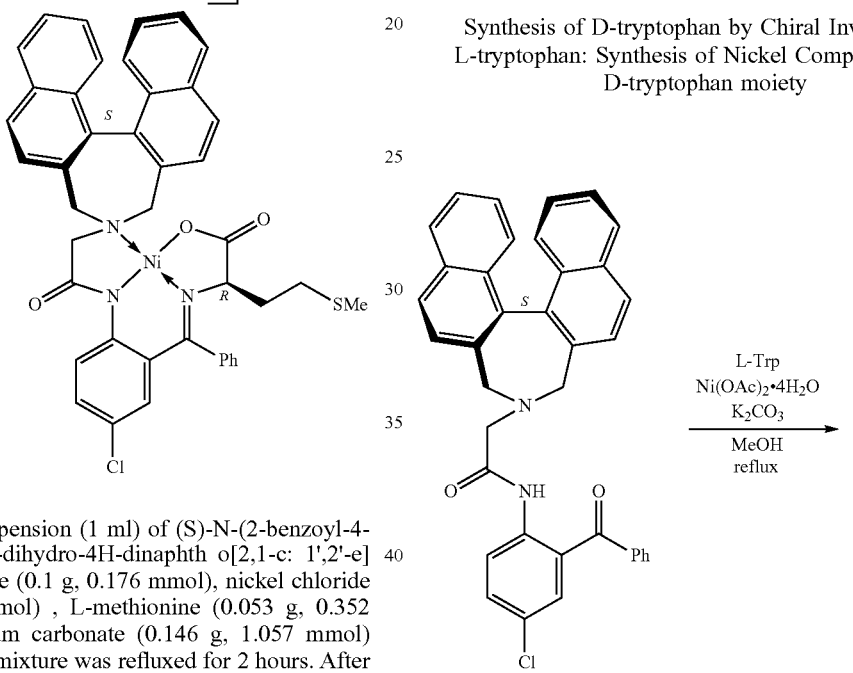

To a methanol suspension (1 ml) of (S)-N-(2-benzoyl-4-chlorophenyl)-2-[3,5-dihydro-4H-dinaphtho[2,1-c: 1',2'-e]azepin-4-yl]acetamide (0.1 g, 0.176 mmol), nickel chloride (0.0457 g, 0.353 mmol), L-methionine (0.053 g, 0.352 mmol), and potassium carbonate (0.146 g, 1.057 mmol) were added, and the mixture was refluxed for 2 hours. After the end of the reaction, the reaction mixture was added to an ice-cooled 5% acetic acid aqueous solution (20 mL) and stirred for 30 minutes to allow crystals to precipitate. The crystals were separated by filtration, and then vacuum-dried at 50° C. to give a nickel (II) complex having a D-methionine moiety (0.129 g, yield: 97.2%, 93.3% de) as red crystals.

ESI-MS (positive mode): m/z=754.3 for [M+H]$^+$.

$^1$H-NMR (200 MHz, CDCl$_3$): δ1.82-2.15 (2H, m, β-CH$_2$ of Met part), 2.12 (3H, s, SMe), 2.70 [1H, d, J=12.3 Hz, one of azepine C(α) H$_2$N], 2.76 (1H, dt, J=13.4, 7.0 Hz, one of γ—CH$_2$ of Met part), 3.05 [1H, d, J=15.6 Hz, one of azepine C(α')H$_2$N], 3.24 (1H, dd, J=13.4, 8.1, 6.3 Hz, one of γ-CH$_2$ of Met part), 3.67 and 3.74 (1H each, ABq, J=14.0 Hz, acetanilide NCOCH$_2$), 3.97 (1H, dd, J=6.8, 4.0 Hz, α-H of Met part), 4.55 [1H, d, J=15.6 Hz, one of azepine C(α') H$_2$N], 4.84 [1H, d, J=12.3 Hz, one of azepine C (α) H$_2$N], 6.64 (1H, d, J=2.4 Hz, ArH), 6.90-6.98 (1H, m, ArH), 7.12-7.19 (1H, m, ArH), 7.22-7.59 (11H, m, ArH), 7.95-8.03 (3H, m, ArH), 8.16 (1H, d, J=8.2 Hz, ArH), 8.43 (1H, d, J=9.2 Hz, ArH), 8.80 (1H, d, J=8.2 Hz, ArH).

$^{13}$C-NMR (50.3 MHz, CDCl$_3$): δ15.7 (Me), 29.8 (CH$_2$), 33.2 (CH$_2$), 58.7 (NCOCH$_2$), 61.8 and 66.5 (2×CH$_2$ of azepine), 69.8 (α-CH of Glu part), 125.2 (ArCH), 126.1 (quaternary ArC), 126.37 (quaternary ArC), 126.44 (ArCH), 126.9 (ArCH), 127.3 (ArCH), 127.5 (ArCH), 127.9 (ArCH), 128.4 (ArCH), 128.6 (ArCH), 128.7 (quaternary ArC), 129.2 (ArCH), 129.37 (ArCH), 129.42 (ArCH), 130.4 (ArCH), 131.0 (quaternary ArC), 131.2 (quaternary ArC), 131.5 (quaternary ArC), 132.4 (ArCH), 132.7 (ArCH), 132.9 (quaternary ArC), 133.7 (quaternary ArC), 134.0 (quaternary ArC), 135.5 (quaternary ArC), 136.0 (quaternary ArC), 141.2 (quaternary ArC), 170.2, 174.6, 178.0 (CN and 2×CO).

Figure 4:
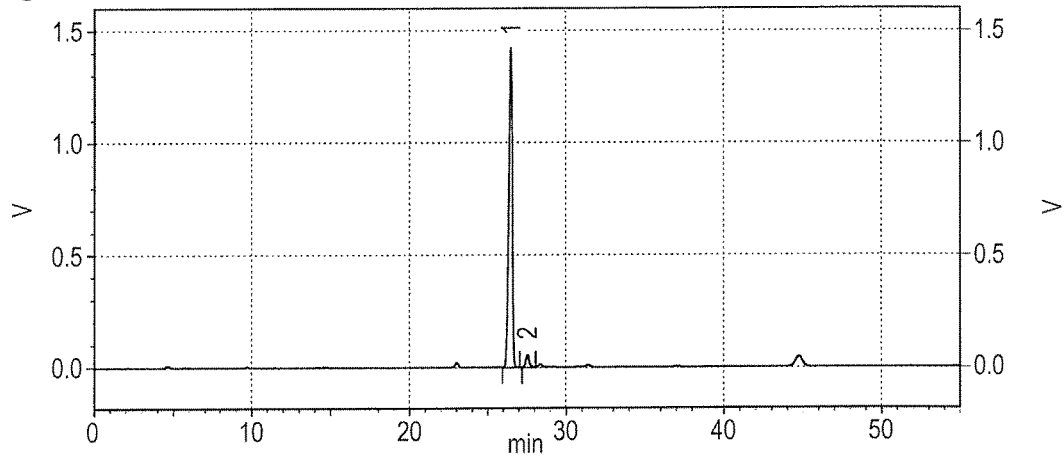
FIG. 4 shows a HPLC analysis result of a Ni (II) complex obtained in Example 2-4, which has D-methionine as a partial structure.

The product of this Example was analyzed under HPLC conditions-1: complex analysis conditions. The results are shown in FIG. 4.

Example 2-5

Synthesis of D-tryptophan by Chiral Inversion of L-tryptophan: Synthesis of Nickel Complex having D-tryptophan moiety

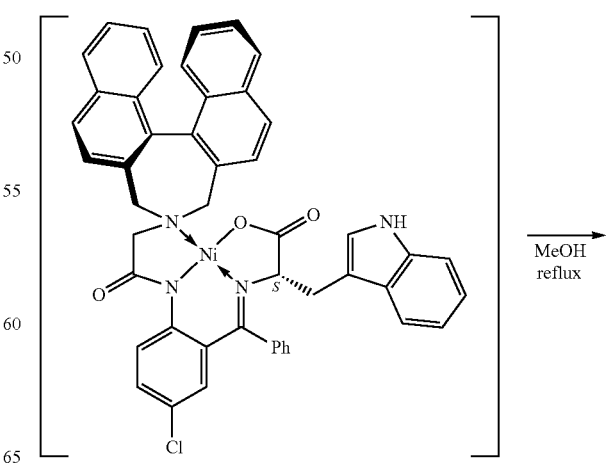

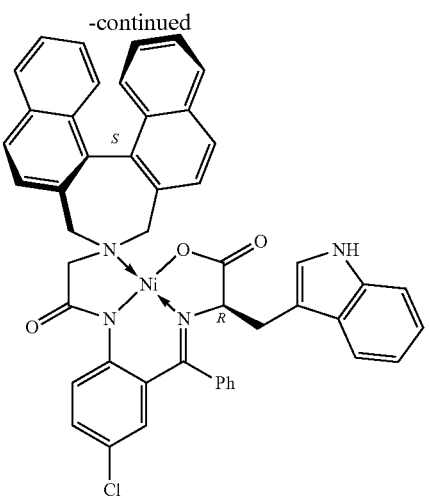

To a methanol suspension (10 mL) of (S)-N-(2-benzoyl-4-chlorophenyl)-2-[3,5-dihydro-4H-dinaphth o[2,1-c:1',2'-e]azepin-4-yl]acetamide (0.5 g, 0.882 mmol), nickel acetate tetrahydrate (0.360 g, 1.763 mmol), L-tryptophan (0.439 g, 1.763 mmol), and potassium carbonate (0.731 g, 5.290 mmol) were added, and the mixture was refluxed with stirring for 24 hours. After the end of the reaction, the reaction mixture was added to an ice-cooled 5% acetic acid aqueous solution (70 mL) and stirred for 30 minutes to allow crystals to precipitate. The crystals were separated by filtration, and then vacuum-dried at 50° C. to give a nickel (II) complex having a D-tryptophan moiety (0.602 g, yield: 84.3%, 99.4% de) as red crystals.

ESI-MS (positive mode): m/z=803.2 for [M+H]$^+$.

$^1$H-NMR (200 MHz, CDCl$_3$): δ1.52 (1H, d, J=14.1 Hz, one of acetanilide NCOCH$_2$), 2.25[1H, d, J=12.1 Hz, one of azepine C(α)H$_2$N], 2.34[1H, d, J=15.6 Hz, one of azepine C(α')H$_2$N], 2.74 (1H, H$_A$ of ABX type, J$_{AB}$=14.4 Hz, J$_{AX}$=5.7 Hz, one of AA β—CH$_2$), 2.81 (1H, d, J=14.1 Hz, one of acetanilide NCOCH$_2$) 3.04[1H, d, J=15.6 Hz, one of azepine C(α')H$_2$N], 3.30 (1H, H$_B$ of ABX type, J$_{AB}$=14.4 Hz, J$_{BX}$=2.2 Hz, one of AA β—CH$_2$), 4.16 (1H, H$_x$ of ABX type, J$_{AX}$=5.7 Hz, J$_{BX}$=2.2 Hz, α-H of AA part), 4.43 [1H, d, J=12.1 Hz, one of azepine C(α) H$_2$N], 6.68 (1H, d, J=2.6 Hz, ArH) , 6.99 (1H, d, J=2.2 Hz, ArH) , 7.02-7.63 (15H, m, ArH), 7.74-7.81 (2H, m, ArH), 7.85-7.94 (3H, m, ArH), 8.06 (1H, d, J=8.4 Hz, ArH), 8.26 (1H, d, J=9.0 Hz, ArH), 8.66 (1H, d, J=8.2 Hz, ArH) , 9.11 (1H, br d, J=1.8 Hz, NH).

$^{13}$C-NMR (50.3 MHz, CDCl$_3$): δ29.7 (β—CH$_2$ of Phe part), 56.5 (NCOCH$_2$), 61.4 and 65.0 (2×CH$_2$ of azepine), 71.8 (α-CH of AA part), 110.4 (ArCH), 111.2 (ArCH), 120.7 (ArCH), 121.1 (ArCH), 122.9 (ArCH), 125.2 (ArCH), 125.5 (ArCH), 126.1 (quaternary ArC), 126.2 (ArCH), 126.3 (ArCH), 127.1 (ArCH), 127.2 (ArCH), 127.4 (ArCH), 127.7 (ArCH), 128.3 (ArCH), 128.4 (ArCH), 128.7 (ArCH), 128.9 (quaternary ArC), 129.0 (quaternary ArC), 129.1 (ArCH), 129.4 (ArCH), 130.4 (ArCH), 130.9 (quaternary ArC), 131.0 (quaternary ArC), 131.3 (quaternary ArC), 132.3 (ArCH), 132.4 (ArCH), 132.8 (quaternary ArC), 133.4 (quaternary ArC), 133.9 (quaternary ArC), 135.2 (quaternary ArC), 135.6 (quaternary ArC), 136.8 (quaternary ArC), 141.0 (quaternary ArC), 169.2, 174.6, 178.8 (CN and 2×CO).

Figure 5:
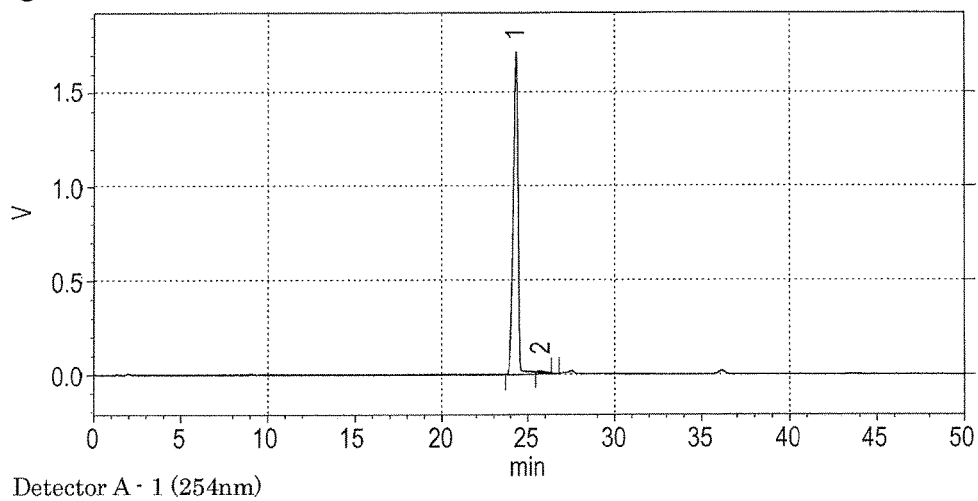
FIG. 5 shows a HPLC analysis result of a Ni (II) complex obtained in Example 2-5, which has D-tryptophan as a partial structure.

The product of this Example was analyzed under HPLC conditions-1: complex analysis conditions. The results are shown in FIG. 5.

Example 2-6

Synthesis of D-glutamine by Chiral Inversion of L-glutamine: Synthesis of Nickel Complex having D-glutamine Moiety

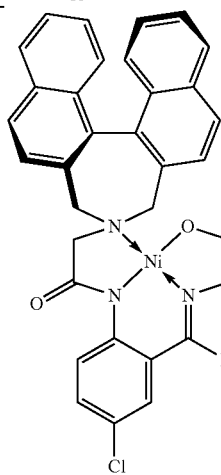
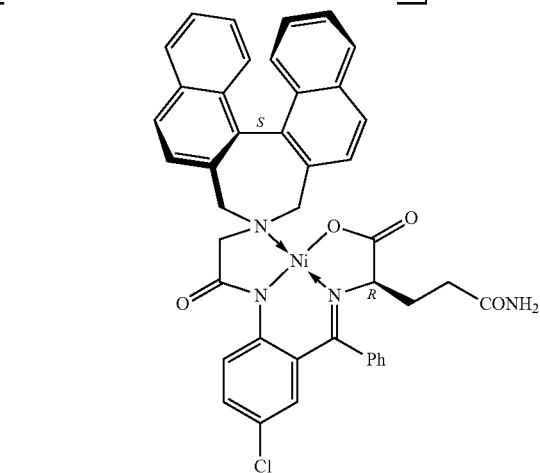

To a methanol suspension (2 mL) of (S)-N-(2-benzoyl-4-chlorophenyl)-2-[3,5-dihydro-4H-dinaphth o[2,1-c: 1',2'-e]azepin-4-yl]acetamide (0.1 g, 0.176 mmol), nickel acetate tetrahydrate (0.0878 g, 0.353 mmol), L-glutamine (0.052 g, 0.333 mmol), and a 28% solution of sodium methoxide (0.204 g, 1.058 mmol) in methanol were added, and the mixture was refluxed for 1 hour and then, stirred at 40° C. for 1 hour. After the end of the reaction, the reaction mixture was added to an ice-cooled 5% acetic acid aqueous solution (15 mL) and stirred for 1 hour to allow crystals to precipitate. The crystals were separated by filtration, and then vacuum-dried at 40° C. to give a nickel (II) complex having a D-glutamine moiety (0.116 g, yield: 87.3%, 94.2% de) as red crystals.

ESI-MS (positive mode): m/z=752.0 for [M+H]$^+$.

$^1$H-NMR (200 MHz, CDCl$_3$): δ1.68-1.88 (1H, m), 2.09-2.25 (1H, m), 2.34-2.70 (2H, m), 2.72 [1H, d, J=12.2 Hz, one of azepine C(α) H$_2$N], 3.00 [1H, d, J=15.6 Hz, one of azepine C(α')H$_2$N], 3.62 and 3.73 (1H each, ABq, J=13.7 Hz, acetanilide NCOCH$_2$), 3.79 (1H, dd, J=8.7, 4.3 Hz, α-H of Gln part), 4.56 [1H, d, J=15.6 Hz, one of azepine C(α)H$_2$N], 4.84 [1H, d, J=12.2 Hz, one of azepine C(α) H$_2$N], 5.20 (1H, for s, one of CONH$_2$), 6.38 (1H, br s, one of CONH$_2$), 6.66 (1H, d, J=2.4 Hz, ArH), 6.94-7.01 (1H, m, ArH), 7.13-7.20 (1H, m, ArH), 7.21-7.33 (3H, m, ArH), 7.37-7.59 (8H, m, ArH), 7.86-0.01 (3K, m, ArH), 8.15 (1H, d, J=8.2 Hz, ArH), 8.45 (1H, d, 2-9.2 Hz, ArH), 3.74 (1H, d, J=8.4 Hz, ArH).

$^{13}$C-NMR (50.3 MHz, CDCl$_3$): δ30.2 (CH$_2$), 31.2 (CH$_2$), 58.4 (NCOCH$_2$), 61.9 and 66.2 (2×CH$_2$ of azepine), 69.8 (α-CH of Gln part), 125.2 (ArCH), 126.1 (quaternary ArC), 126.5 (ArCH), 126.6 (ArCH), 127.3 (ArCH), 127.5 (ArCH), 127.6 (ArCH), 123.0 (ArCH), 128.1 (quaternary ArC), 128.4 (ArCH), 128.6 (ArCH), 128.8 (quaternary ArC), 129.0 (ArCH), 129.1 (ArCH), 129.3 (ArCH), 129.5 (ArCH), 130.3 (ArCH), 131.1 (quaternary ArC), 131.2 (quaternary ArC), 131.4 (quaternary ArC), 132.6 (ArCH), 132.7 (ArCH), 133.6 (quaternary ArC), 133.0 (quaternary ArC), 135.5 (quaternary ArC), 136.1 (quaternary ArC), 141.0 (quaternary ArC), 170.7, 173.6, 174.8, 178.5 (CN and 3×CO).

Figure 6:
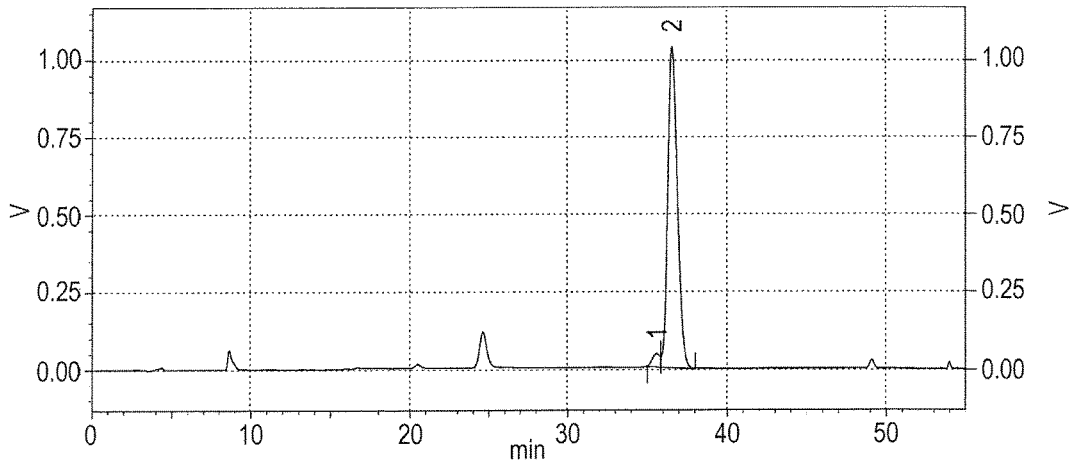
FIG. 6. shows a HPLC analysis result of a Ni (II) complex obtained in Example 2-6, which has D-glutamine as a partial structure.

The product of this Example was analysed under HPLC conditions-3: Gln complex analysis conditions. The results are shown in FIG. 6.

Example 2-7

Synthesis of D-glutamic acid by Chiral Inversion of L-glutamic Acid: Synthesis of Nickel Complex having D-glutamic Acid Moiety

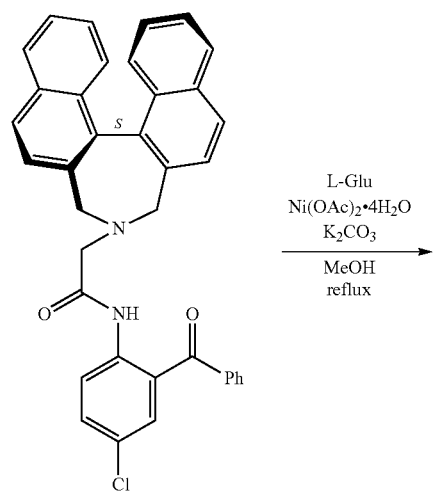

L-Glu
Ni(OAc)$_2$·4H$_2$O
K$_2$CO$_3$
MeOH
reflux

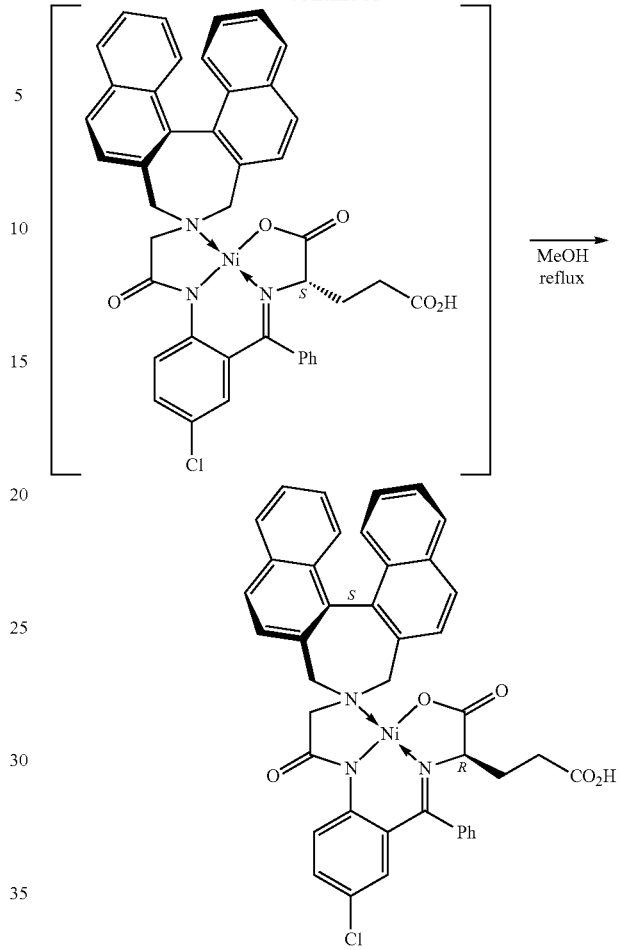

To a methanol suspension (2 mL) of (S)-N-(2-benzoyl-4-chlorophenyl)-2-[3,5-dihydro-4H-dinaphth o[2,1-c: 1', 2'-e]azepin-4-yl]acetamide (0.1 g, 0.176 mmol), nickel acetate tetrahydrate (0.878 g, 0.353 mmol), L-glutamic acid (0.052 q, 0.353 mmol), and potassium carbonate (0.133 g, 1.411 mmol) were added. To this, methanol (2 mL) was further added, and the mixture was stirred at 60° C. for 9 hours. After the end of the reaction, the reaction mixture was added to an ice-cooled 5% acetic acid aqueous solution (15 mL) and stirred for 1 hour to allow crystals to precipitate. The crystals were separated by filtration, and then vacuum-dried at 40° C. to give a nickel (II) complex having a D-glutamic acid moiety (0.110 g, yield: 82.5%, 91.8% de (determined based on $^1$H-NMR spectrum)) as red crystals.

ESI-MS (positive mode): m/z=752.0 for [M+H]$^+$.

$^1$H-NMR (200 MHz, CDCl$_3$): δ1.60-1.78 (1H, m, one of β-CH$_2$ of Glu part), 1.90-2.10 (1H, m, one of β—CH$_2$ of Glu part), 2.50-2.70 (1H, m, one of γ—CH$_2$ of Glu part), 2.64 [1H, d, J=12.1 Hz, one of azepine C(α) H$_2$N], 2.95 [1H, d, J=15.6 Hz, one of azepine C(α')H$_2$N], 3.20-3.41 (1H, m, one of γ13 CH$_2$ of Glu part), 3.67 and 3.81 (1H each, ABq, J=13.8 Hz, acetanilide NCOCH$_2$), 3.94 (1H, br t-like, α-H of Glu part), 4.5-5.1 (1H, br, CO$_2$H) , 4.77 [1H, d, J=15.6 Hz, one of azepine C(α')H$_2$N], 4.78 [1H, d, J=12.1 Hz, one of azepine C(α) H$_2$N], 6.56 (1B, d, J=2.6 Hz, ArH), 6.98-7.64 (12H, m, ArH), 7.61 (1H, d, J=8.2 Hz, ArH), 7.91-8.01 (3H, m, ArH), 8.14 (1H, d, J=8.4 Hz, ArH), 8.28 (1H, d, J=9.2 Hz, ArH), 8.78 (1H, d, J=8.4 Hz, ArH).

¹³C-NMR (50.3 MHz, CDCl₃): δ27.4 (CH₂), 30.4 (CH₂), 58.5 (NCOCH₂), 61.8 and 66.5 (2×CH₂ of azepine), 70.4 (α—CH of Glu part), 125.2 (ArCH), 126.1 (quaternary ArC), 126.37 (ArCH), 126.44 (ArCH), 126.6 (ArCH), 127.5 (ArCH), 127.6 (ArCH), 127.8 (ArCH), 128.0 (ArCH), 128.37 (quaternary ArC), 128.44 (ArCH), 128.7 (ArCH), 129.0 (ArCH), 129.1 (ArCH), 129.2 (ArCH), 129.4 (ArCH), 130.2 (ArCH), 131.1 (quaternary ArC), 131.2 (quaternary ArC), 131.5 (quaternary ArC), 132.5 (ArCH), 132.9 (quaternary ArC), 133.7 (quaternary ArC), 134.0 (quaternary ArC), 135.4 (quaternary ArC), 136.1 (quaternary ArC), 140.8 (quaternary ArC), 171.5, 175.7, 176.2, 178.3 (CN and 3×CO).

Figure 7:
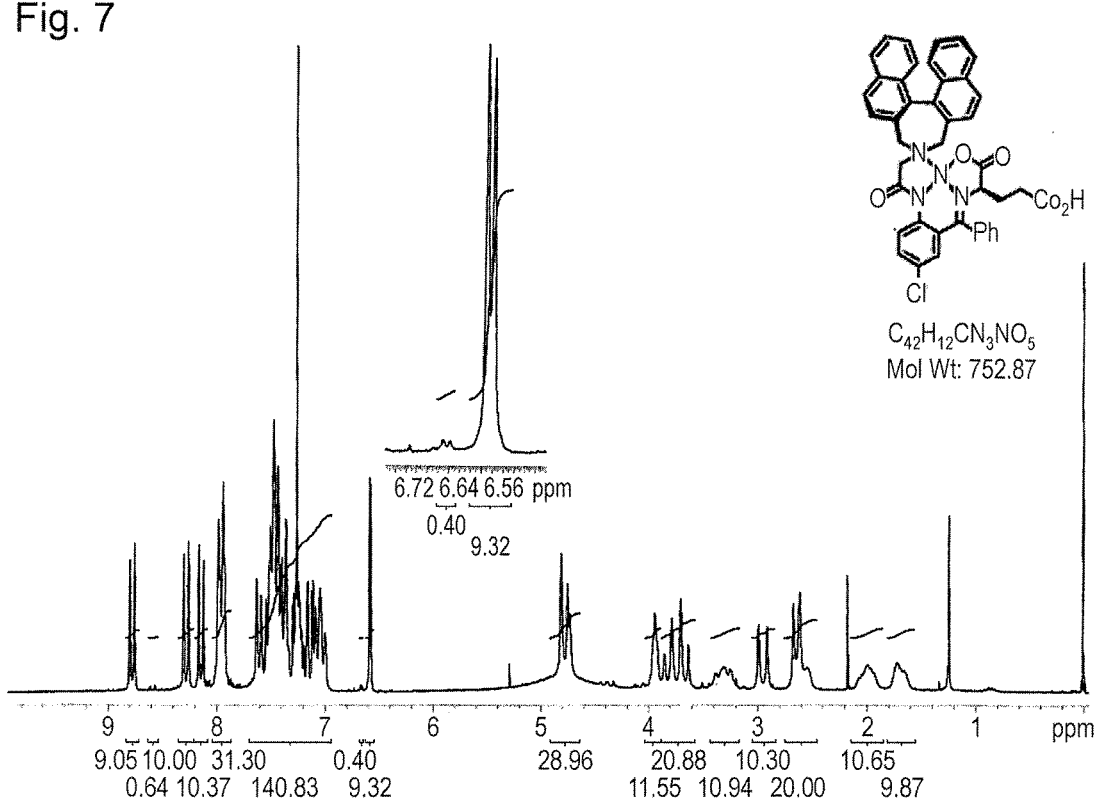
FIG. 7 snows a $^1$H-NMR spectrum of a Ni (II) complex obtained in Example 2-7, which has D-glutamic acid as a partial structure.

In the ¹H-NMR of the product of this Example, the signals at chemical shift values (multiplicity, coupling constant) of 6.58 ppm (d, J=2.6 Hz) and 6.66 ppm (d, J=2.6 Hz) correspond to the proton signals of the aromatic rings of nickel (II) complexes having a D-glutamic acid moiety and an L-glutamic acid moiety, respectively, and the integrated intensity ratio was 9.32:0.40 (=95.9:4.1). Based on the results, the diastereomer excess (de) was determined to foe 91.8%. The ¹-NMR spectrum of the product of this Example is shown in FIG. 7.

Example 2-8

Synthesis of D-lysine by Chiral Inversion of L-lysine: Synthesis of Nickel Complex having D-lysine Moiety

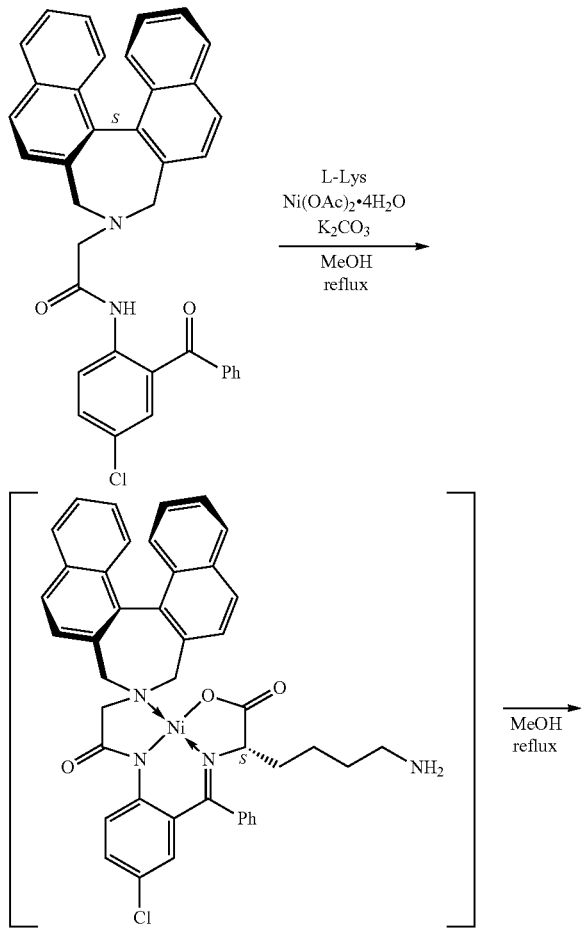

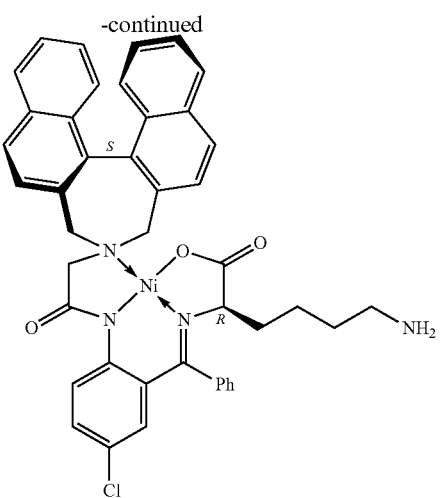

To a methanol suspension (2 mL) of (S)-N-(2-benzoyl-4-chlorophenyl)-2-[3,5-dihydro-4H-dinaphtho[2,1-c:1',2'-e] azepin-4-yl]acetamide (0.3 g, 0.529 mmol), nickel acetate tetrahydrate (0.263 g, 1.053 mmol), L-lysine hydrochloride (1.193 g, 1.508 mmol), and potassium carbonate (0.585 g, 4.232 mmol) were added, and the mixture was refluxed for 4 hours. After the end of the reaction, dichloromethane (5 mL) and a 5% acetic acid aqueous solution (5 mL) were added to the reaction mixture, and phase separation was performed. To the organic layer, dichloromethane and methanol were added, and the liquid was washed with water (5 mL) and then with saturated brine (5 mL). The organic layer was concentrated, and the residue was washed with stirring in dichloromethane (1 mL) and ethyl acetate (6 mL). The crystals were separated by filtration, and then blow-dried at 50° C. to give a nickel (II) complex having a D-lysine moiety (0.323 g, yield: 81.2%) as a red solid.

ESI-MS (positive mode): m/z=751.2 for [M+H]⁺.

¹H-NMR (200 MHz, CDCl₃): δ1.20-1.80 (4H, m), 1.82-2.02 (1H, m), 2.23-2.43 (1H, m), 2.52-2.7S (1H, br), 2.72 [1H, d, J=12.3 Hz, one of azepine C(α) H₂N], 3.04[1H, d, J=15.6 Hz, one of azepine C(α')H₂N], 3.27 (3H, br, NH₂ and one of CH₂), 3.66 and 3.83 (1H each, ABq, J=13.6 Hz, acetanilide NCOCH₂), 3.82 (1H, H$_x$ of ABX system, overlapped, α-H of Lys part), 4.73 [1H, d, J=15.6 Hz, one of azepine C(α')H₂N], 4.80 [1H, d, J=12.3 Hz, one of axepine C(α) H₂N], 6.64 (1H, d, J=2.6 Hz, ArH), 6.84-6.91 (1H, m, ArH), 7.14-7.56 (11H, m, ArH), 7.61 (1H, d, J=8.2 Hz, ArH), 7.90-8.00 (3H, m, ArH), 8.14 (1H, d, J 8.2 Hz, ArH), 8.42 (1H, d, J=9.2 Hz, ArH), 8.75 (1H, d, J=8.2 Hz, ArH).

¹³C-NMR (50.3 MHz, CDCl₃): δ22.6 (γ—CH₂), 30.9 (δ—CH₂), 34.6 (β—CH₂), 40.6 (ε—CH₂), 58.5 (NCOCH₂l), 61.8 and 66.3 (2×CH₂ of azepine), 70.6 (α—CH of Lys part), 125.2 (ArCH), 126.2 (quaternary ArC), 126.3 (quaternary ArC), 126.4 (ArCH), 127.0 (ArCH), 127.5 (ArCH), 127.9 (ArCH), 128.4 (ArCH), 128.7 (ArCH), 128.9 (quaternary ArC), 129.17 (ArCH), 129.24 (ArCH), 129.4 (ArCH), 130.3 (ArCH), 131.1 (quaternary ArC), 131.2 (quaternary ArC), 131.4 (quaternary ArC), 132.4 (ArCH), 132.6 (ArCH), 132.8 (quaternary ArC), 133.7 (quaternary ArC), 134.0 (quaternary ArC), 135.5 (quaternary ArC), 136.0 (quaternary ArC), 141.0 (quaternary ArC), 170.0, 174.8, 178.5 (CH and 2×CO).

Example 3-1

Release of L-phenylalanine from Nickel (II) Complex having L-phenylalanine Moiety (Obtained by Deracemization of Racemic Mixture of Phenylalanine: or by Chiral Inversion of D-phenylalanine) in Acid Condition, and Protection of L-phenylalanine with Z-group

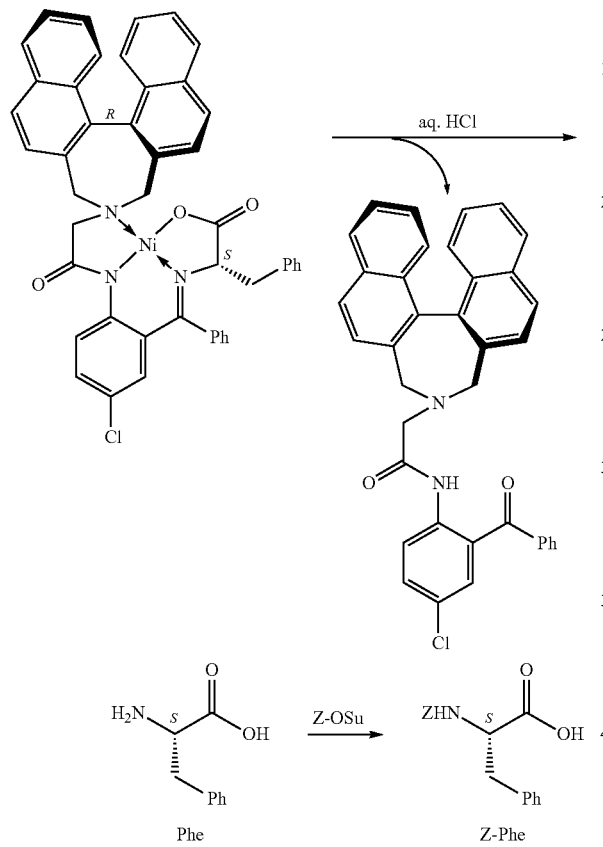

To a methanol suspension (12 mL) of a nickel (II) complex having an L-phenylalanine moiety (0.4 g, 0.52 mmol), 1 N hydrochloric acid (2.6 mL, 5 eq.) was added, and the mixture was stirred at 40° C. for 6 hours. After the end of the reaction, the reaction mixture was concentrated, and the residue was dissolved in dichloromethane (10 mL). The organic layer was extracted with 2% aqueous ammonia (6 mL, twice) and water (6 mL, twice) and then washed, with saturated brine (6 mL, twice). The obtained organic layer was dried over sodium sulfate, and the sodium sulfate was filtered off. The filtrate was concentrated to dryness to give a chiral auxiliary (0.27 g, yield: 90%) as a pale yellow solid.

The aqueous ammonia layers and the aqueous layers resulting from the extraction were combined and concentrated to dryness. The obtained solid was dissolved in 9% aqueous ammonia (3 mL) and passed through a cation exchange resin column (made by Mitsubishi Chemical Corp., trade name: SK1B, 9 mL, eluent: water and subsequently aqueous ammonia 2%→8%)) to give phenylalanine (0.083 g, crude product).

To the phenylalanine (0.078 g), an aqueous solution (3 mL) of sodium hydrogencarbonate (0.041 mg, 1 eq.)—sodium carbonate (0.103 mg, 2 eq.), and acetone (1 mL) were added to dissolve the phenylalanine. To the solution in an ice bath, an acetone solution (1 mL) of N-benzyloxycarbonyloxy succinimide (0.121 g, 1 eq. ) was added, and the mixture was stirred at room, temperature for 3 hours. The reaction mixture was concentrated, the residue was subjected to phase separation with ethyl acetate (18 mL) and 1 N hydrochloric acid (2.5 mL), and the aqueous layer was extracted with ethyl acetate (18 mL). The organic layer was washed with saturated brine (5 mL, twice), dried over sodium sulfate, and then concentrated to give a yellow oily substance (0.182 g). The obtained yellow oily substance was dissolved in isopropyl alcohol (0.08 mL)—ethyl acetate (0.8 mL). To this, an ethyl acetate solution (0.4 mL) of dicyclohexylamine (0.094 g, 1 eq. ) was added, and then ethyl acetate (2.0 mL) was further added. The mixture was stirred at room temperature for 9 hours. The precipitated crystals were separated by filtration, and then blow-dried at 50° C. to give a Z-L-phenylalanine DCHA salt (0.178 g, yield: 76%, 99.0% ee) as white crystals.

Figure 8:
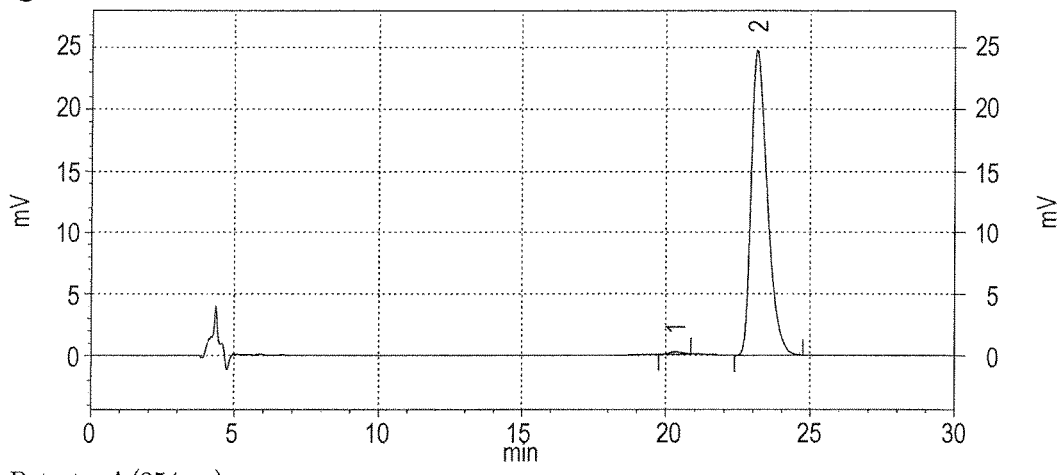
FIG. 8 shows a HPLC analysis result of the L-phenylalanine protected by a Z group (Z-L-phenylalanine) obtained in Example 3-1.

The product of this Example was analyzed under HPLC conditions-2': Z-Phe chiral analysis conditions 2. The results are shown in FIG. 8.

Example 3-2

Release of D-phenylalanine from Nickel (II) Complex having D-phenylalanine Moiety (Obtained by Deracemization of Racemic Mixture of Phenylalanine or by Chiral Inversion of L-phenylalanine) in Acid Condition, and Protection with Z-group

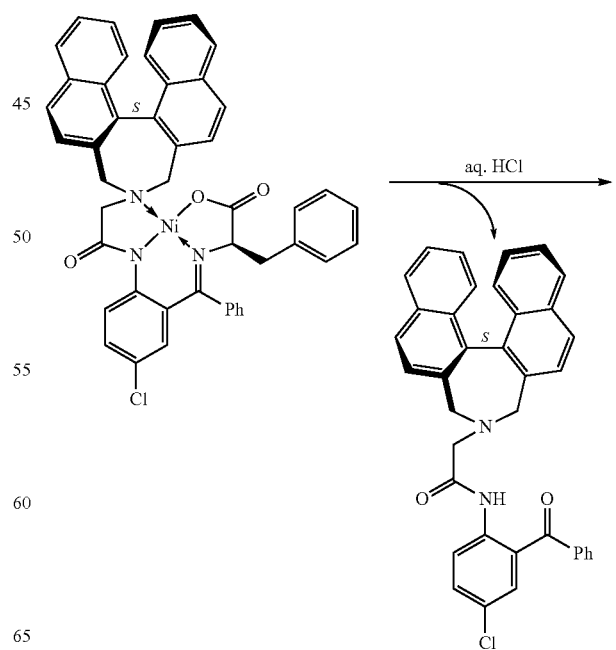

47

-continued

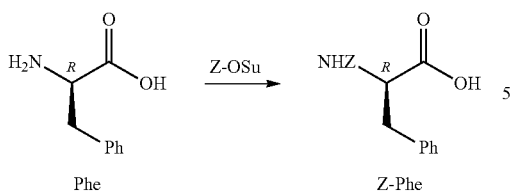

Phe → Z-Phe (Z-OSu)

To a methanol suspension (12 mL) of a nickel (II) complex having a D-phenylalanine moiety (0.4 g, 0.53 mmol), 1 N hydrochloric acid (3.2 mL, 6 eq.) was added, and the mixture was stirred at 40° C. for 6 hours. After the end of the reaction, the reaction mixture was concentrated, and the residue was dissolved in ethyl acetate (20 mL). The organic layer was sequentially extracted with water (4 mL), 1H hydrochloric acid (4 mL), and water (4 mL), The obtained organic layer was sequentially washed with a saturated sodium hydrogen carbonate aqueous solution (4 mL), water (4 mL), and saturated brine (4 mL), and then dried over sodium sulfate. The sodium sulfate was filtered off, and the filtrate was concentrated to dryness to give a chiral auxiliary (0.29 g, yield; 96%) as a pale yellow solid.

Meanwhile, the aqueous layer resulting from the extraction (12 mL) was concentrated to dryness. The obtained solid was dissolved in 13% aqueous ammonia (4 mL) and passed through a cation exchange resin column (made by Mitsubishi Chemical Corp., trade name: SK1B, 30 mL, eluent: water and subsequently aqueous ammonia (8%)) to give phenylalanine (0.102 g, crude product, quantitative).

To the phenylalanine (0.102 g), an aqueous solution (3 mL) of sodium hydrogencarbonate (0.090 mg, 2 eq.)—sodium carbonate (0.057 mg, 1 eq.), and acetone (1 mL) were added to dissolve the phenylalanine. To the solution in an ice bath, an acetone solution (2 mL) of N-benzyloxycarbonyloxy succinimide (0.139 g, 1.04 eq.) was added, and the mixture was stirred at room temperature for 3.5 hours. The reaction mixture was concentrated, and the residue was subjected to phase separation with water (17 mL) and toluene (1 mL). To the aqueous layer, a 10% aqueous solution of citric acid was added to adjust the pH to 3, and then extraction with ethyl acetate (30 mL, 15 mL) was performed. The organic layers were washed with water (2 mL) and saturated brine (2 mL, 3 times), dried over sodium sulfate, and then concentrated to give a yellow oily substance (0.161 g, crude product, quantitative).

The obtained yellow oily substance was dissolved in isopropyl alcohol (0.01 mL)-ethyl acetate (0.6 mL). To this, an ethyl acetate solution (0.1 mL) of dicyclohexylamine (0.097 g, 1 eq.) was added, and then ethyl acetate (0.9 mL) and hexane (3 mL) were further added. The mixture was stirred at room temperature overnight. The precipitated crystals were separated by filtration, and then vacuum-dried at 50° C. to give a Z-D-phenylalanine DCHA salt (0.247 g, yield: 96%, 99.0% ee, abbreviated as Z-Phe) as white crystals.

Figure 9:
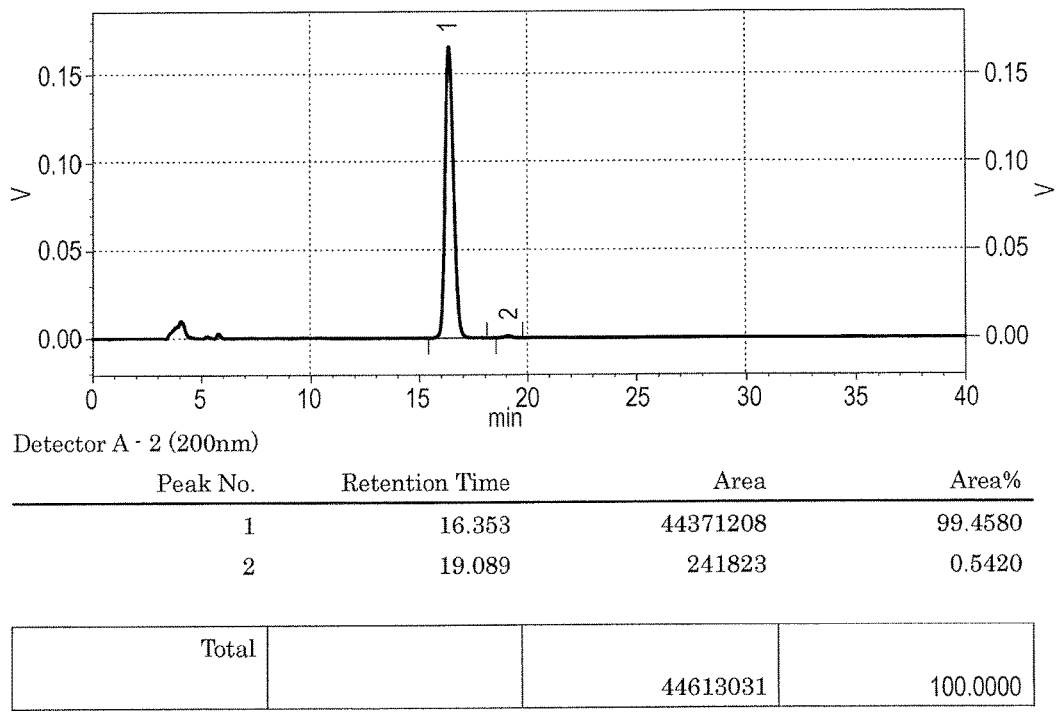
FIG. 9 shows a HPLC analysis result of the D-phenylalanine protected by a Z group obtained in Example 3-2.

The product of this Example was analyzed under HPLC conditions-2: Z-Phe chiral analysis conditions 1. The results are shown in FIG. 9.

48

Example 3-3

Release of D-lysine from Nickel (II) Complex having D-lysine Moiety (Obtained by Chiral Inversion of L-lysine) in Acid Condition, and Protection with Z-group

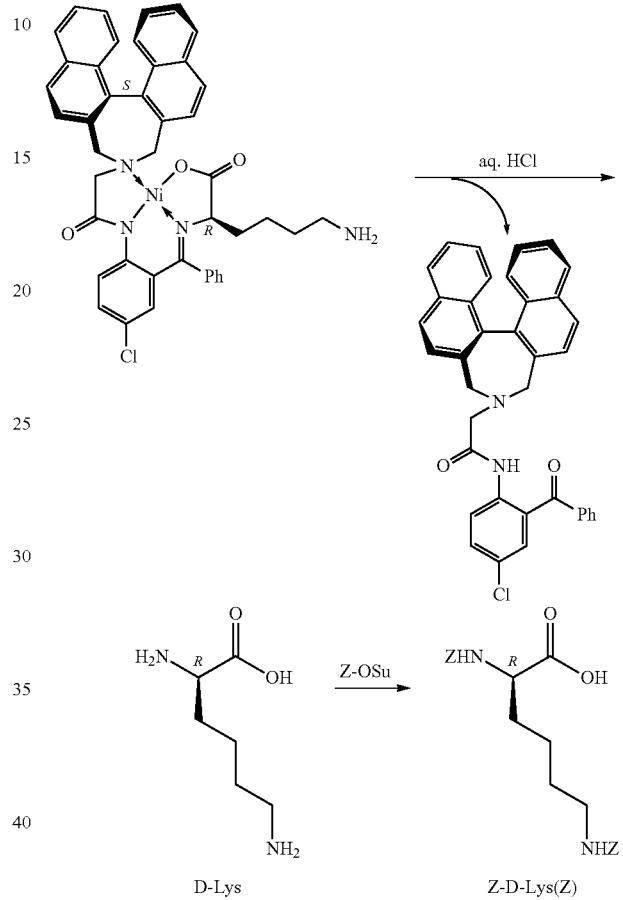

D-Lys → Z-D-Lys(Z) (Z-OSu)

To a methanol suspension (6 mL) of a nickel (II) complex having a D-lysine moiety (0.2 g, 0.27 mmol), 1 N hydrochloric acid (1.6 mL, 6 eq.) was added, and the mixture was stirred at 40° C. for 4 hours. After the end of the reaction, the reaction mixture was concentrated, and the residue was dissolved in ethyl acetate (10 mL). The organic layer was sequentially extracted with water (10 mL, 5 mL, 5 mL). The obtained organic layer was sequentially washed with a saturated sodium hydrogencarbonate aqueous solution (5 mL), water (5 mL), and saturated brine (5 mL), and then dried over sodium sulfate. The sodium sulfate was filtered off, and the filtrate was concentrated to dryness to give a chiral auxiliary (0.14 g, yield: 33%) as a pale yellow solid.

Meanwhile, the aqueous extraction liquid (20 mL) was washed with a small amount of methylene chloride, and then concentrated to dryness. The obtained solid was dissolved in water-methanol and a small amount of aqueous ammonia (1 raid and passed through a cation exchange resin column (made by Mitsubishi Chemical Corp., trade name: SK1B, 3 mL, eluent: water and subsequently aqueous ammonia (8%)) to give D-lysine (0.038 g, crude product).

To the D-lysine (0.034 g), an aqueous solution (1 mL) of sodium hydrogencarbonate (0.079 mg, 4 eq.)—sodium carbonate (0.050 mg, 2 eq.), and THF (1 mL) were added to dissolve the lysine. To the solution in an ice bath, a THF solution (2.5 mL) of N-benzyloxycarbonyloxy succinimide (0.118 g, 2 eq.) was added, and the mixture was stirred at room temperature for 2 hours. The reaction mixture was concentrated, and the obtained residue was subjected to phase separation with water (10 mL) and toluene (1 mL). To the aqueous layer, a 10% aqueous solution of citric acid was added to adjust the pH to 3, and then extraction with ethyl acetate (15 mL, 10 mL, 5 ml) was performed. The organic layers were washed with water (2 mL, twice) and saturated brine (5 ml, twice), and then dried over sodium sulfate. The sodium sulfate was filtered off, and the filtrate was concentrated. The obtained yellow oily substance (0.102 g, crude product, yield: 93%) was purified by silica gel column chromatography to give D-lysine protected by a Z group (Z-D-Lys(Z)) (0.082 g) as an oily substance. The obtained colorless oily substance (0.064 g) was dissolved in isopropyl alcohol (0.01 mL)-ethyl acetate (0.6 mL). To this, an ethyl acetate solution (0.1 mL) of dicyclohexylamine (0.028 g, 1 eq.), ethyl acetate (0.9 mL), and hexane (3 mL) were added, and the mixture was stirred at room temperature overnight. The precipitated crystals were separated by filtration, and then vacuum-dried at 50° C. to give a Z-D-Lys (Z) DCHA salt (0.084 g, yield: 69% (yield from Ni (II) complex), 93.2% ee) as white crystals.

Figure 10:
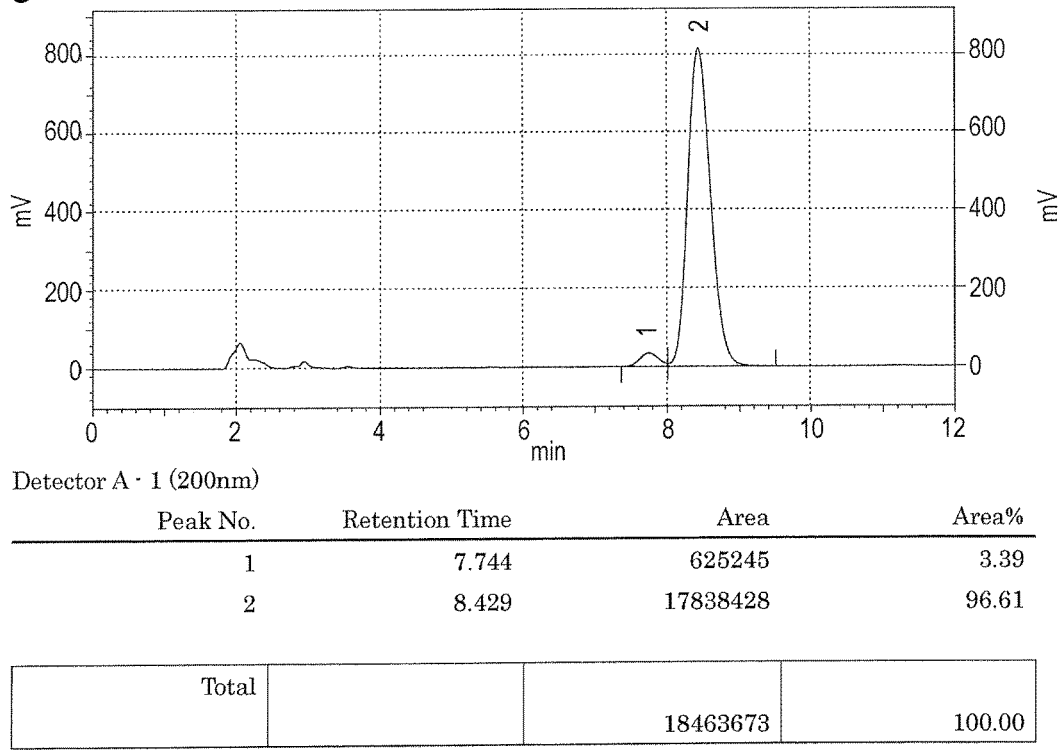
FIG. 10 shows a HPLC analysis result of the dicyclohexylamine salt of D-lysine protected by Z groups (Z-D-Lys (Z)) obtained in Example 3-3.

The product of this Example was analyzed under HPLC conditions-4: Z-D-Lys(Z) chiral analysis conditions. The results are shown in FIG. 10.

Example 4

Deracemization

Example 4-1

Synthesis of D-phenylalanine by Deracemization of DL-phenylalanine

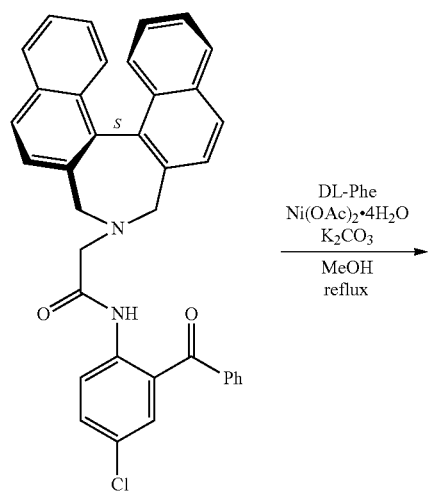

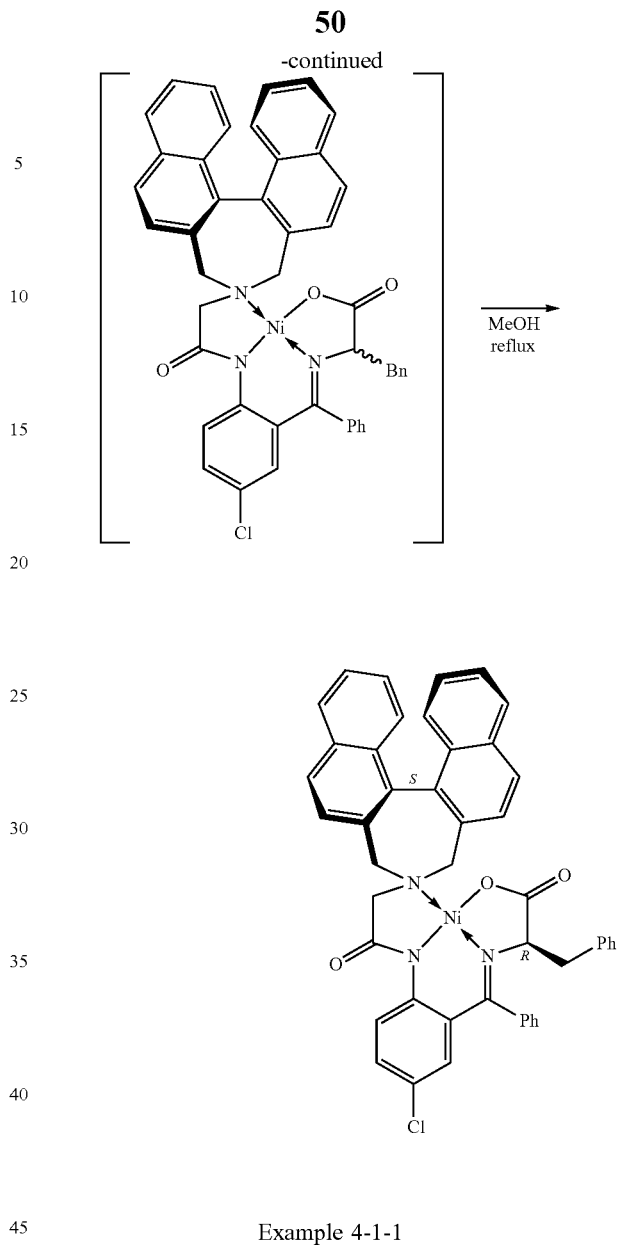

Example 4-1-1

Case where DL-phenylalanine (2 eq.), Nickel Acetate Tetrahydrate (2 eq.), and Potassium Carbonate (6 eq.) are Used Relative to chiral Auxiliary To a methanol suspension (4 mL) of (S)-N-(2-benzoyl-4-chlorophenyl)-2-[3,5-dihydro-4H-dinaphth o[2,1-c:1',2'-e]azepin-4-yl]acetamide (0.2 g, 0.353 mmol), nickel acetate tetrahydrate (0.176 g, 0.706 mmol), DL-phenylalanine (0.117 g, 0.706 mmol), and potassium carbonate (0.293 g, 2.118 mmol) were added, and the mixture was refluxed for 24 hours. After the end of the reaction, the reaction mixture was added to an ice-cooled 5% acetic acid aqueous solution (15 mL) and stirred for 30 minutes to allow crystals to precipitate. The crystals were separated by filtration, and then blow-dried at 50° C. to give a nickel (II) complex having a D-phenylalanine moiety (0.234 g, yield: 86%, 99% de) as red crystals.

ESI-MS (positive mode); m/z=770.2 for [M+H]$^+$.

$^1$H-NMR (200 MHz, CDCl$_3$): δ2.42 [1H, d, J=12.3 Hz, one of azepine C(α)H$_2$N], 2.59 (1H, H$_A$ of ABX type, J$_{AB}$=13.6 Hz, J$_{AX}$=5.3 Hz, one of Phe βCH$_2$) 2.61 [1H, d, J=15.5 Hz, one of azepine C (α')H$_2$N], 2.76 and 3.18 (1H each, ABq, J=13.9 Hz, acetanilide NCOCH$_2$), 3.00 (1H, H$_B$ of ABX type, J$_{AB}$=13.6 Hz, J$_{BX}$=3.0 Hz, one of Pheβ-CH$_2$), 3.68 [1H, d, J=15.5 Hz, one of azepine C(α')H$_2$N], 4.22 (1H, H$_X$ of ABX type, J$_{AX}$=5.3 Hz, J$_{BX}$=3.0 Hz, α-H of Phe part), 4.54 [1H, d, J=12.3 Hz, one of azepine C(α)H$_2$N], 6.67 (1H, d, J=2.4 Hz), 7.05-7.64 (15H, m, ArH), 7.66-7.85 (3H, m, ArH), 7.90-7.99 (3H, m( ArH), 8.09 (1H, d, J=8.2 Hz, ArH), 8.35 (1H, d, J=9.2 Hz, ArH), 8.67 (1H, d, J=8.2 Hz, ArH).

$^{13}$C-NMR (50.3 MHz, CDCl$_3$): δ39.1 (β—CH of Phe part), 57.6 (NCOCH$_2$), 61.6 and 65.9 (2×CH$_2$ of azepine), 72.1 (α—CH of Phe part), 125.2 (ArCH), 126.1 (quaternary ArC), 126.3 (ArCH), 127.1 (ArCH), 127.5 (ArCH), 127.6 (ArCH), 127.7 (ArCH), 127.8 (ArCH), 128.4 (ArCH), 128.6 (ArCH), 128.8 (quaternary ArC), 128.95 (ArCH), 129.02 (ArCH), 129.3 (ArCH), 129.4 (ArCH), 130.4 (ArCH), 131.0 (quaternary ArC), 131.2 (quaternary ArC), 131.5 (quaternary ArC), 131.8 (ArCH), 132.4 (ArCH), 132.7 (ArCH), 133.0 (quaternary ArC), 133.6 (quaternary ArC), 134.0 (quaternary ArC), 135.4 (quaternary ArC), 135.9 (quaternary ArC), 136.5 (quaternary ArC), 141.4 (quaternary ArC), 169.9, 174.3, 177.4 (CN and 2×CO).

Figure 11:
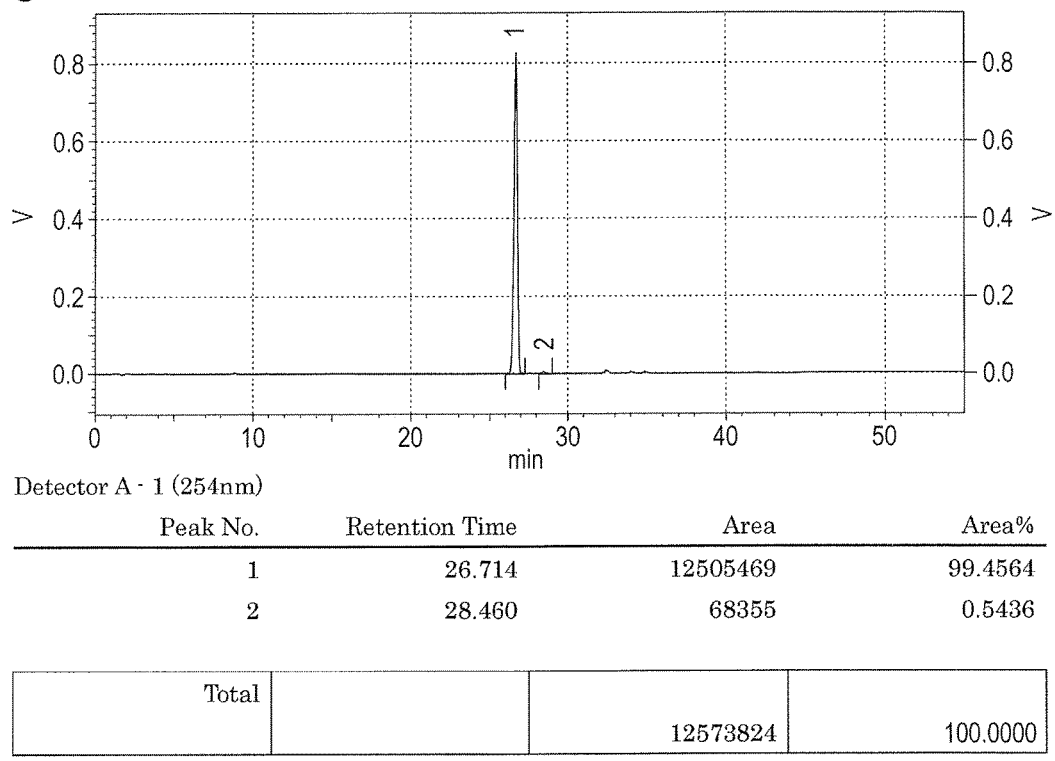
FIG. 11 shows a HPLC analysis result of a Ni (II) complex obtained in Example 4-1-1, which has D-phenylalanine as a partial structure.

The product of this Example was analyzed under HPLC conditions-1: complex analysis conditions. The results are shown in FIG. 11.

D-phenylalanine can be obtained by processing this complex in the same manner as in Example 3.

Example 4-1-2

Case where DL-phenylalanine (1.1 eq.), Nickel Acetate Tetrahydrate (1.1 eq.), and Potassium Carbonate (4 eq. ) are Used Relative to Chiral Auxiliary To a methanol, suspension (4 mL) of (S)-N-(2-benzoyl-4-chlorophenyl)-2-[3,5-dihydro-4H-dinaphth o [2,1-c:1',2'-e] azepin-4-yl]acetamide (0.2 g, 0.353 mmol), nickel acetate tetrahydrate (0.97 g, 0.388 mmol), DL-phenylalanine (0.64 g, 0 .386 mmol), and potassium carbonate (0.195 g, 1.411 mmol) were added, and the mixture was refluxed for 24 hours. After the end of the reaction, the reaction mixture was added to an ice-cooled 5% acetic acid aqueous solution (15 mL) and stirred for 30 minutes to allow crystals to precipitate. The crystals were separated by filtration, and then blow-dried at 50° C. to give a nickel (II) complex having a D-phenylalanine moiety (0.246 g, yield; 90.5%, 97.2% de) as red crystals.

Figure 12:
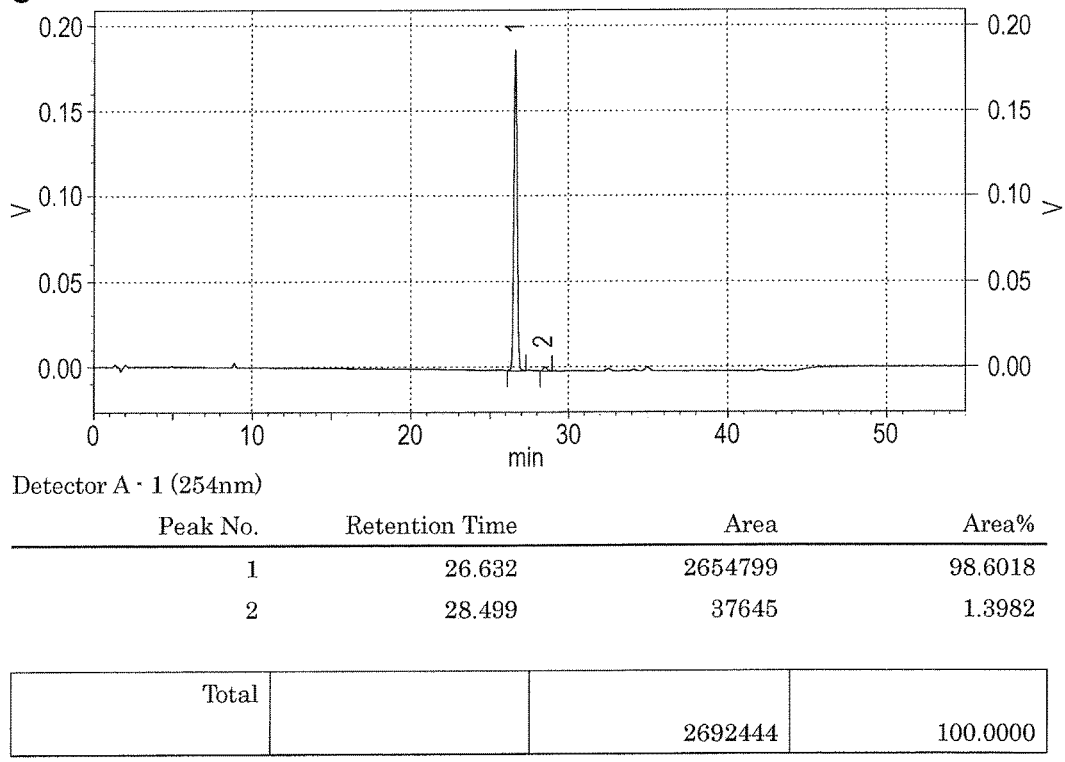
FIG. 12 shows a HPLC analysis result of a Ni (II) complex obtained in Example 4-1-2, which has D-phenylalanine as a partial structure.

The product of this Example was analyzed under HPLC conditions-1: complex analysis conditions. The results are shown in FIG. 12.

D-phenylalanine can be obtained by processing this complex in the same manner as in Example 3.

Example 4-2

Synthesis of L-phenylalanine by Deracemization of DL-phenylalanine

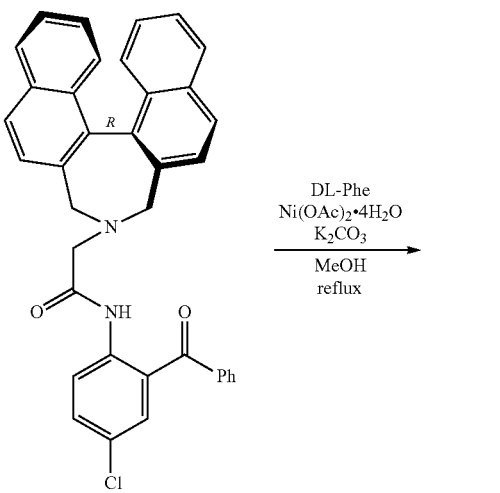

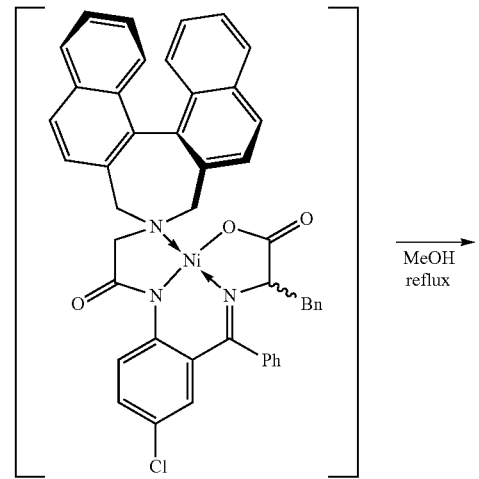

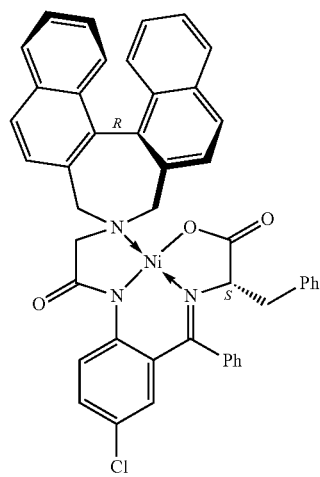

Example 4-2-1

Case where DL-phenylalanine (2 eq.), Nickel Acetate Tetrahydrate (2 eq.), and Potassium Carbonate (6 eq.) are Used Relative to Chiral Auxiliary To a methanol suspension (16 mL) of (R)-N-(2-benzoyl-4-chlorophenyl)-2-[3,5-dihydro-4H-dinaphth o[2,1-c: 1',2'-e]azepin-4-yl]acetamide (0.8 g, 1.411 mmol), nickel acetate tetrahydrate (0.702 g, 2.821 mmol), DL-phenylalanine (0.466 g, 2.821 mmol), and potassium, carbonate (1.170 g, 8.484 mmol) were added, and the mixture was refluxed for 24 hours. After the end of the reaction, the reaction mixture was added to an ice-cooled 5% acetic acid aqueous solution (120 mL) and stirred for 30 minutes to allow crystals to precipitate, The crystals were separated by filtration, and then blow-dried at 50° C. to give a nickel (II) complex having an L-phenylalanine moiety (1.035 g, yield: 95.2%, 99% de) as red crystals.

ESI-MS (positive mode): m/z=770.3 for [M+H]$^+$.

$^1$H-NMR (200 MHz, CDCl$_3$s): δ2.42 [1H, d, J=12.1 Hz, one of azepine C(α)H$_2$N], 2.59 (1H, H$_A$ of ABX type, J$_{AB}$=13.6 Hz, J$_{AX}$=5.5 Hz, one of Pheβ-CH$_2$), 2.61 [1H, d, J=15.6 Hz, one of azepine C(α')H$_2$N], 2.76 and 3.17 (1H each, ABq, J=13.9 Hz, acetanilide NCOCH$_2$), 3.00 (1H, H$_B$ of ABX type, J$_{AB}$=13.6 Hz, J$_{BX}$=3.0 Hz, one of Phe β-CH$_2$), 3.68 [1H, d, J=15.6 Hz, one of azepine C(α')H$_2$N], 4.23 (1H, H$_X$ of ABX type, J$_{AX}$=5.5 Hz, J$_{BX}$=3.0 Hz, α-H of Phe part), 4.54 [1H, d, J=12.1 Hz, one of azepine C(α)H$_2$N], 6.67 (1H, d, J=2.4 Hz), 7.05-8.02 (21H, m, ArH), 8.09 (1H, d, J=8.4 Hz, ArH), 8.34 (1H, d, J=9.2 Hz, ArH), 8.68 (1H, d, J=8.2 Hz, ArH).

$^{13}$C-NMR (50.3 MHz, CDCl$_3$): δ39.0 (β-CH$_2$ of Phe part), 57.5 (NCOCH$_2$), 61.6 and 65.9 (2×CH$_2$ of azepine), 72.1 (α-CH of Phe part), 125.2 (ArCH), 126.1 quaternary ArC), 126.4 (ArCH), 127.1 (ArCH), 127.4 (ArCH), 127.5 (ArCH), 127.7 (ArCH), 127.8 (ArCH), 128.4 (ArCH), 128.6 (ArCH), 128.8 (quaternary ArC), 129.0 (ArCH), 129.1 (ArCH), 129.3 (ArCH), 129.4 (ArCH), 150.5 (ArCH), 131.0 (quaternary ArC), 131.2 (quaternary ArC), 131.4 (quaternary ArC), 131.8 (ArCH), 132.4 (ArCH), 132.7 (ArCH), 132.9 (quaternary ArC), 133.6 (quaternary ArC), 133.9 (quaternary ArC), 135.3 (quaternary ArC), 135.9 (quaternary ArC), 136.5 (quaternary ArC), 141.4 (quaternary ArC), 169.9, 174.3, 177.4 (CN and 2×CO).

Figure 13:
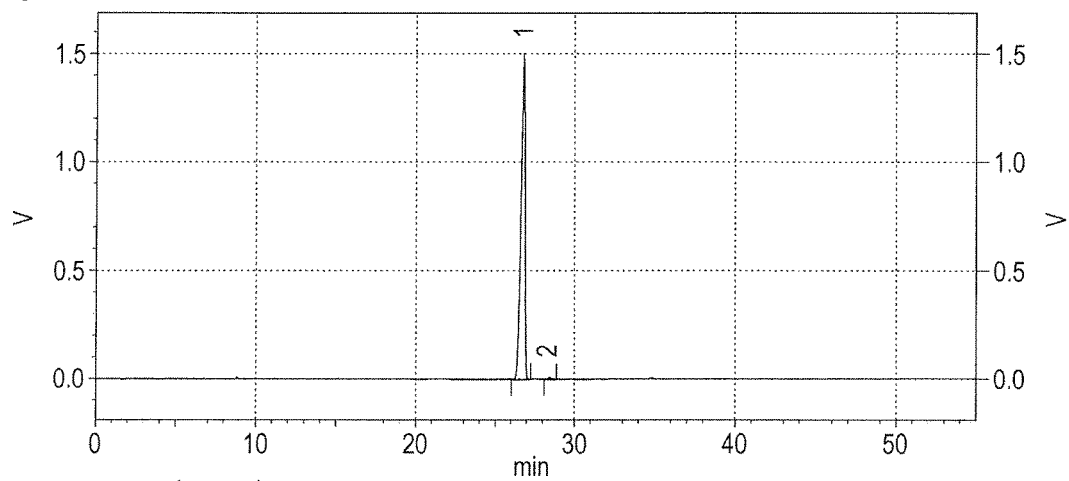
FIG. 13 shows a HPLC analysis result of a Ni (II) complex obtained in Example 4-2-1, which has L-phenylalanine as a partial structure.

The product of this .Examples was analyzed under HPLC Conditions-1: complex analysis conditions. The results are shown in FIG. 13.

L-phenylalanine can foe obtained by processing this complex in the same manner as in Example 3.

Example 4-2-2

Case where DL-phenylalanine (1.1 eq.), Nickel Acetate Tetrahydrate (1.1 eq.), and Potassium Carbonate (4 eq.) are Used Relative to Chiral Auxiliary To a methanol suspension (4 mL) of (R)-N-(2-benzoyl-4-chlorophenyl)-2-[3,5-dihydro-4H-dinaphth o [2,1-c: 1',2'-e] azepin-4-yl]acetamide (0.2 g, 0.353 mmol), nickel acetate tetrahydrate (0.097 q, 0.383 mmol), DL-phenylalanine (0.064 g, 0.388 mmol), and potassium carbonate (0.195 g, 1.411 mmol) were added, and the mixture was refluxed for 24 hours. After the end of the reaction, the reaction mixture was added to an ice-cooled 53 acetic acid aqueous solution (30 mL) and stirred for 30 minutes to allow crystals to precipitate. The crystals were separated by filtration, and then blow-dried at 50° C. to give a nickel (II) complex having an L-phenylalanine moiety (0.250 g, yield: 92.1%, 97% de) as red crystals.

Figure 14:
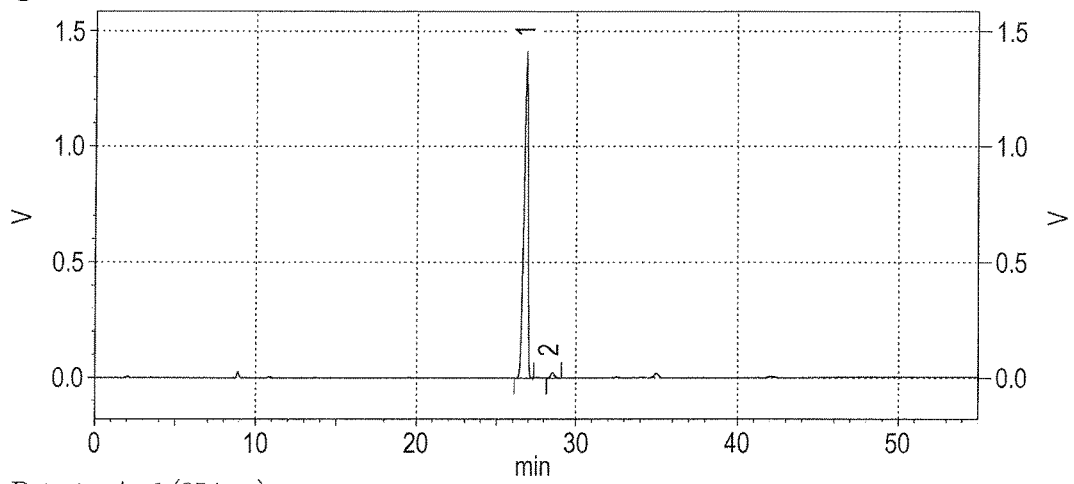
FIG. 14 shows a HPLC analysis result of a Ni (II) complex obtained in Example 4-2-2, which has L-phenylalanine as a partial structure.

The product of this Example was analysed under HPLC conditions-1: complex analysis conditions. The results are shown in FIG. 14.

L-phenylalanine can be obtained by processing this complex in the same manner as in Example 3-1.

Example 4-3

Synthesis of D-valine by Deracemization of DL-valine

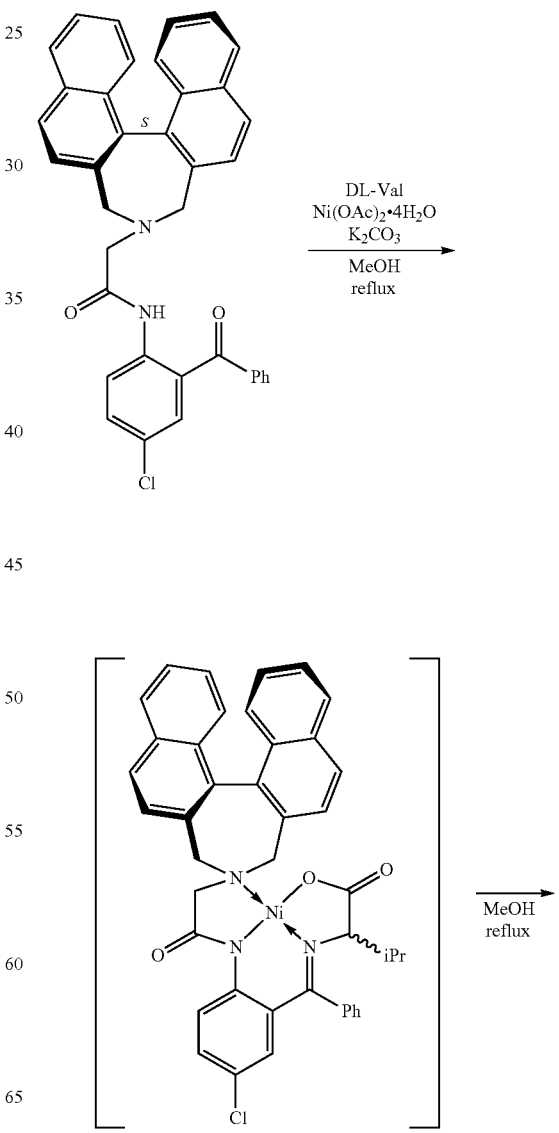

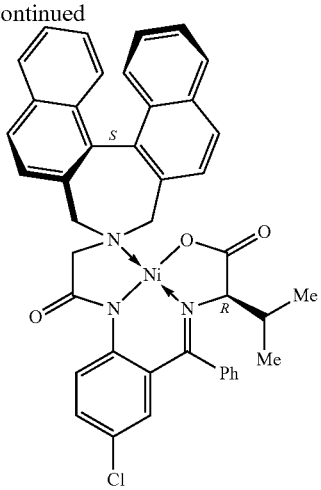

To a methanol suspension (4 mL) of (S)-N-(2-benzoyl-4-chlorophenyl)-2-[3,5-dihydro-4H-dinaphth o[2,1-c:1',2'-e]azepin-4-yl]acetamide (0.2 g, 0.353 mmol), nickel acetate tetrahydrate (0.176 g, 0.706 mmol), DL-valine (0.083 g, 0.706 mmol), and potassium carbonate (0.293 g, 2.118 mmol) were added, and the mixture was refluxed for 27 hours. After the end of the reaction, the reaction mixture was added to an ice-cooled 5% acetic acid aqueous solution (15 mL) and stirred for 30 minutes to allow crystals to precipitate. The crystals were separated by filtration, and then blow-dried at 50° C. to give a nickel (II) complex having a D-valine moiety (0.203 g, yield: 79.6%, 92.4% de) as red crystals.

ESI-MS (positive mode): m/z=722.2 for [M+H]$^+$.

$^1$H-NMR (200 MHz, CDCl$_3$): δ0.80 (3H, d, J=7.0 Hz, Me), 1.79 (1H, doubtet of septets, J=3.5, 7.0 Hz, CHMe$_2$), 2.18 (3H, d, J=6.8 Hz, Me), 2.54 [1H, d, J=12.3 Hz, one of azepine C (α) (H$_2$N], 3.02 [1H, d, J=15.6 Hz, one of azepine C(α)H$_2$N], 3.64 and 3.75 (1H each, ABq, J=13.9 Hz, acetanilide NCOCH$_2$), 3.72 (1H, d, J=3.3 Hz, α-H of Val part), 4.54 [1H, d, J=15.6 Hz, one of azepine C(α)H$_2$N], 4.73 [1H, d, J=12.3 Hz, one of azepine C(α)H$_2$N], 6.55 (1H, d, J=2.4 Hz), 6.84-6.95 (2H, m, ArH), 7.14-7.55 (10H, m, ArH), 7.55 (1H, d, J=8.4 Hz, ArH), 7.92-8.04 (3H, m, ArH), 8.19 (1H, d, J=8.2 Hz, ArH), 3.44 (1H, d, J=9.0 Hz, ArH), 8.99 (1H, d, J=8.2 Hz, ArH).

$^{13}$C-NMR (50.3 MHz, CDCl$_3$): δ18.5 and 19.7 (2×Me of Val part), 34.5 (β—CH of Val part), 59.1 (NCOCH$_2$), 61.5 and 66.7 (2×CH$_2$ of azepine), 75.9 (α—CH of val part), 125.0 (ArCH), 126.1 (quaternary ArC), 126.37 (ArCH), 126.44 (ArCH), 127.1 (ArCH), 127.2 (ArCH), 127.4 (ArCH), 127.8 (ArCH), 128.0 (ArCH), 128.4 (ArCH), 128.55 (quaternary ArC), 128.62 (quaternary ArC), 128.7 (ArCH), 128.9 (ArCH), 129.1 (ArCH), 129.5 (ArCH), 130.1 (ArCH), 131.0 (quaternary ArC), 131.2 (quaternary ArC), 131.5 (quaternary ArC), 132.4 (ArCH), 132.5 (ArCH), 132.7 (quaternary ArC), 133.7 (quaternary ArC), 134.1 (quaternary ArC), 135.4 (quaternary ArC), 136.0 (quaternary ArC), 141.0 (quaternary ArC), 169.7, 174.3, 176.3 (CN and 2×CO).

Figure 15:
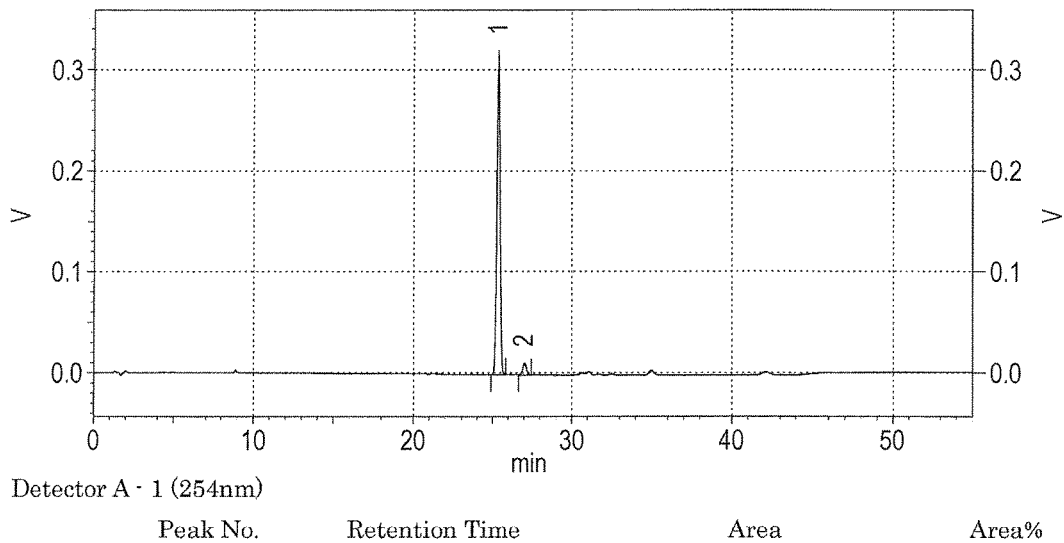
FIG. 15 shows a HPLC analysis result of a Ni (II) complex obtained in Example 4-3, which has D-valine as a partial structure.

The product of this Example was analyzed under HPLC conditions-1: complex analysis conditions. The results are shown in FIG. 15. D-valine can be obtained by processing this complex in the same manner as in Example 3.

Example 4-4

Synthesis of L-valine by Deracemization of DL-valine

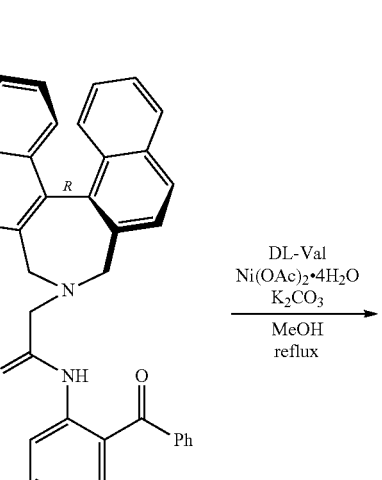

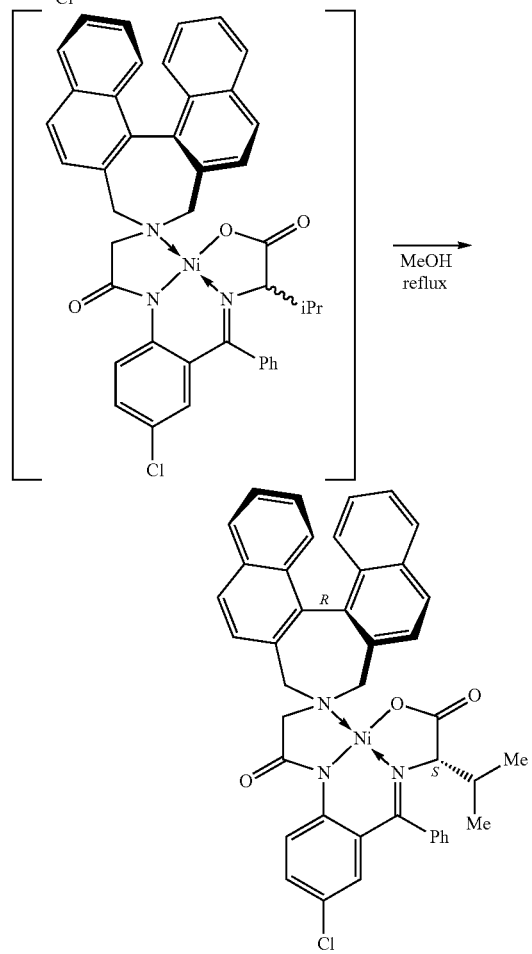

To a methanol suspension (4 mL) of (R)-N-(2-benzoyl-4-chlorophenyl)-2-[3,5-dihydro-4H-dinaphth o [2,1-c:1',2'-e]azepin-4-yl]acetamide (0.2 g, 0.353 mmol), nickel acetate tetrahydrate (0.176 g, 0.706 mmol), DL-valine (0.083 g, 0.706 mmol), and potassium carbonate (0.293 g, 2.118 mmol) were added, and the mixture was refluxed for 24 hours. After the end of the reaction, the reaction mixture was added to an ice-cooled 5% acetic acid aqueous solution (30 mL) and stirred for 30 minutes to allow crystals to precipitate. The crystals were separated by filtration, and then blow-dried at 50° C. to give a nickel (II) complex having an L-valine moiety (0.232 g, yield: 91.0%, 95% de) as red crystals.

Figure 16:
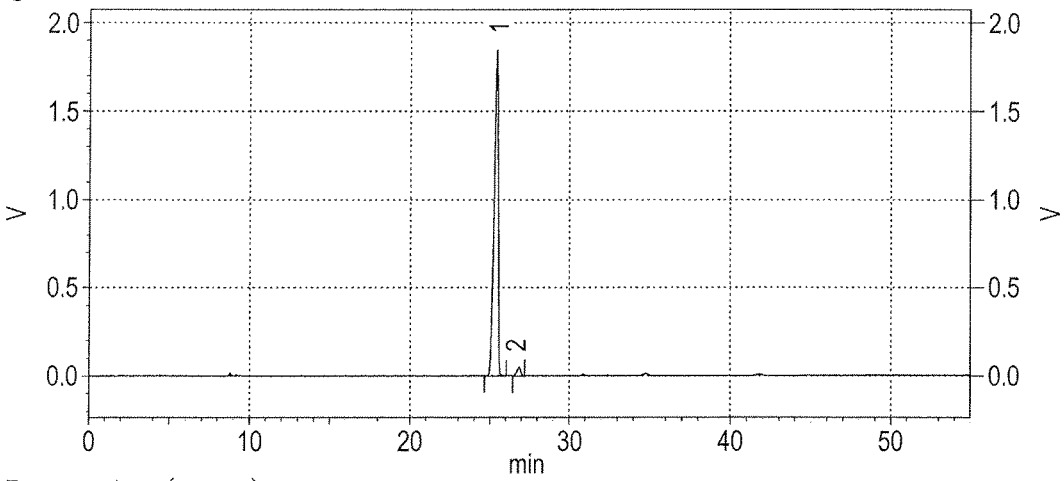
FIG. 16 shows a HPLC analysis result of a Ni (II) complex obtained in Example 4-4, which has L-valine as a partial structure.

The product of this Example was analyzed under HPLC conditions-1: complex analysis conditions. The results are shown in FIG. 16.

L-valine can be obtained by processing this complex in the same manner as in Example 3.

Example 4-5

Synthesis of D-alanine by Deracemization of DL-alanine

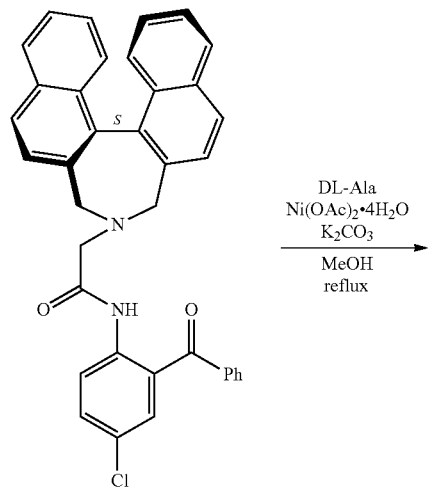

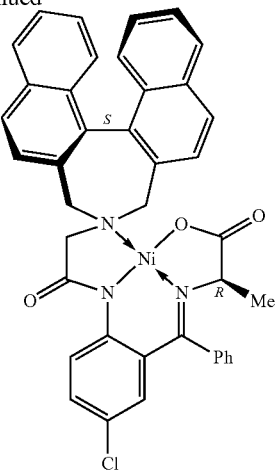

To a methanol suspension (4 mL) of (S)-H-(2-benzoyl-4-chlorophenyl)-2-[3,5-dihydro-4H-dinaphth o [2,1-c:1',2'-e]azepin-4-yl]acetamide (0.2 g, 0.353 mmol), nickel acetate tetrahydrate (0.176 q, 0.706 mmol), DL-alanine (0.063 g, 0.706 mmol), and potassium carbonate (0.293 g, 2.118 mmol) were added, and the mixture was refluxed for 24 hours. After the end of the reaction, the reaction mixture was added to an ice-cooled 5%acetic acid aqueous solution (15 mL) and stirred for 30 minutes to allow crystals to precipitate. The crystals were separated by filtration, and then blow-dried at 50° C. to give a nickel (II) complex having a D-alanine moiety (0.208 g, yield: 84.8%, 95.8% de) as red crystals.

Figure 17:
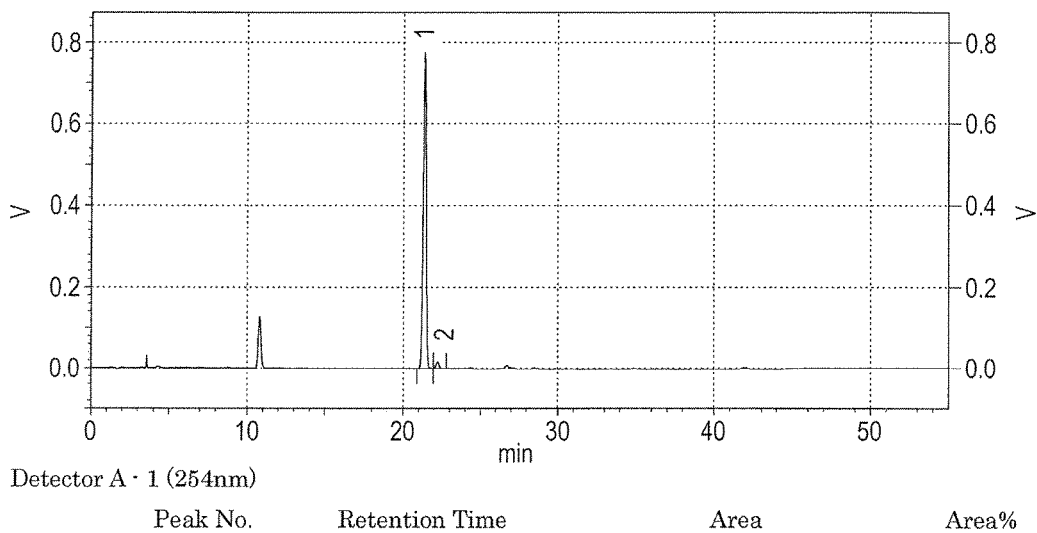
FIG. 17 shows a HPLC analysis result of a Ni (II) complex obtained in Example 4-5, which has D-alanine as a partial structure.

The product of this Example was analyzed under HPLC conditions-1: complex analysis conditions. The results are shown in FIG. 17.

D-alanine can be obtained by processing this complex in the same manner as in Example 3.

Example 4-6

Synthesis of L-alanine by Deracemization of DL-alanine

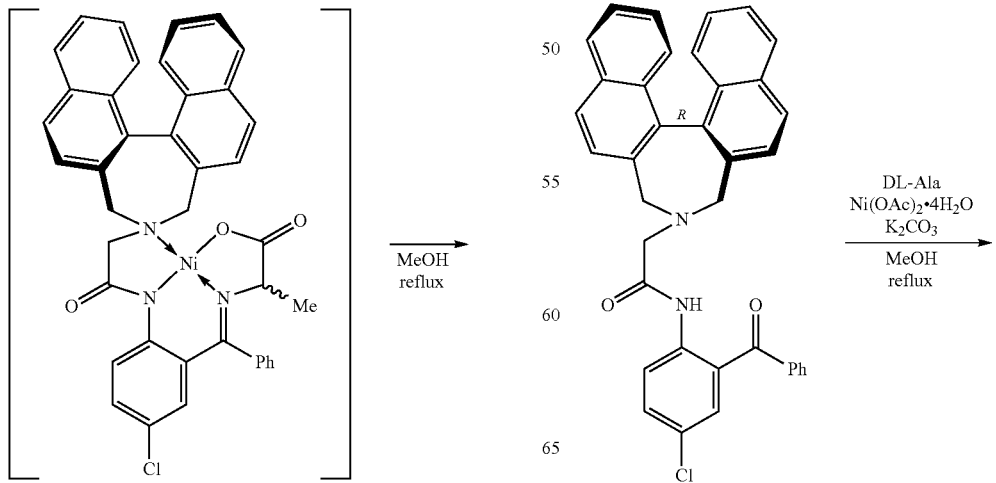

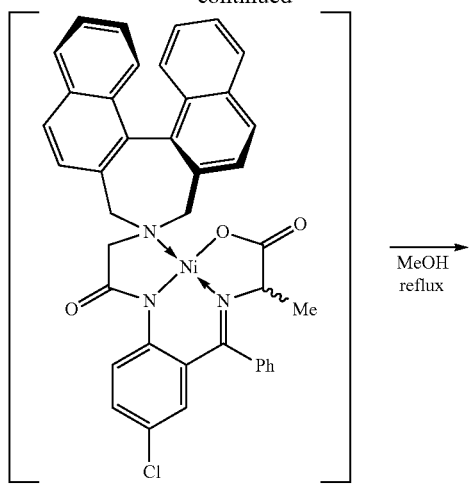

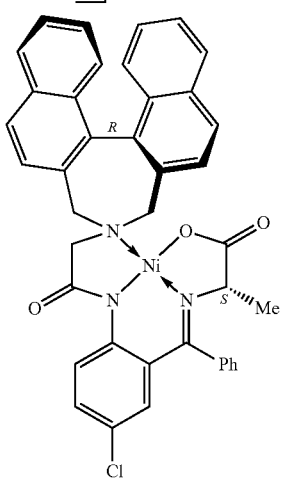

To a methanol suspension (4 mL) of (R)-N-(2-benzoyl-4-chlorophenyl)-2-[3,5-dihydro-4H-dinaphtho[2,1-c:1',2'-e]azepin-4-yl]acetamide (0.2 g, 0.353 mmol), nickel acetate tetrahydrate (0.176 g, 0.706 mmol), DL-alanine (0.063 g, 0.706 mmol), and potassium carbonate (0.293 g, 2.118 mmol) were added, and the mixture was heated at 40° C. for 24 hours. After the end of the reaction, the reaction mixture was added to an ice-cooled 5% acetic acid aqueous solution (30 mL) and stirred for 30 minutes to allow crystals to precipitate. The crystals were separated by filtration, and then blow-dried at 50° C. to give a nickel (II) complex having an L-alanine moiety (0.207 g, yield: 84.8%, 96% de) as red crystals.

ESI-MS (positive mode): m/z=694.2 for [M+H]$^+$.

$^1$H-NMR (200 MHz, CDCl$_3$): δ1.51 (3H, d, J=7.0 Hz, Me), 2.73 [1H, d, J=12.2 Hz, one of azepine C(α)H$_2$N], 3.08 [1H, d, J =15.6 Hz, one of azepine C(α)H$_2$N], 3.68 and 3.76 (1H each, ABq, J=13.9 Hz, acetanilide NCOCH$_2$), 3.84 (1H, q, J=7.0 Hz, α-H of Ala part), 4.57 [1H, d, J=15.6 Hz, one of azepine C(α)H$_2$N], 4.84 [1H, d, J=12.1 Hz, one of azepine C(α)H$_2$N], 6.66 (1H, d, J=2.6 Hz), 6.91-6.99 (1H, m, ArH), 7.16-7.32 (4H, m, ArH), 7.35-7.41 (1H, m, ArH), 7.43-7.57 (7H, m, ArH), 7.94-8.93 (3H, m, ArH), 8.16 (1H, d, J=8.3 Hz, ArH), 8.44 (1H, d, J=9.2 Hz, ArH), 8.76 (1B, d, J=8.3 Hz, ArH).

$^{13}$C-NMR (50.3 MHz, CDCl$_3$): δ21.5 (Me of Ala part), 58.7 (NCOCH$_2$), 61.9 and 66.3 (2×CH$_2$ of azepine), 66.9 (α—CH of Ala part), 125.1 (ArCH), 126.1 (quaternary ArC), 126.3 (quaternary ArC), 126.44 (ArCH), 126.9 (ArCH), 127.3 (ArCH), 127.4 (ArCH), 127.5 (ArCH), 127.6 (ArCH), 127.6 (ArCH), 128.2 (quaternary ArC), 128.4 (ArCH), 128.7 (ArCH), 129.2 (ArCH), 129.5 (ArCH), 130.2 (ArCH), 131.0 (quaternary ArC), 131.3 (quaternary ArC), 131.5 (quaternary ArC), 132.4 (ArCH), 132.6 (ArCH), 132.7 (quaternary ArC), 133.7 (quaternary ArC), 134.1 (quaternary ArC), 135.6 (quaternary ArC), 136.0 (quaternary ArC), 140.9 (quaternary ArC), 170.2, 174.6, 179.7 (CN and 2×CO).

Figure 18:
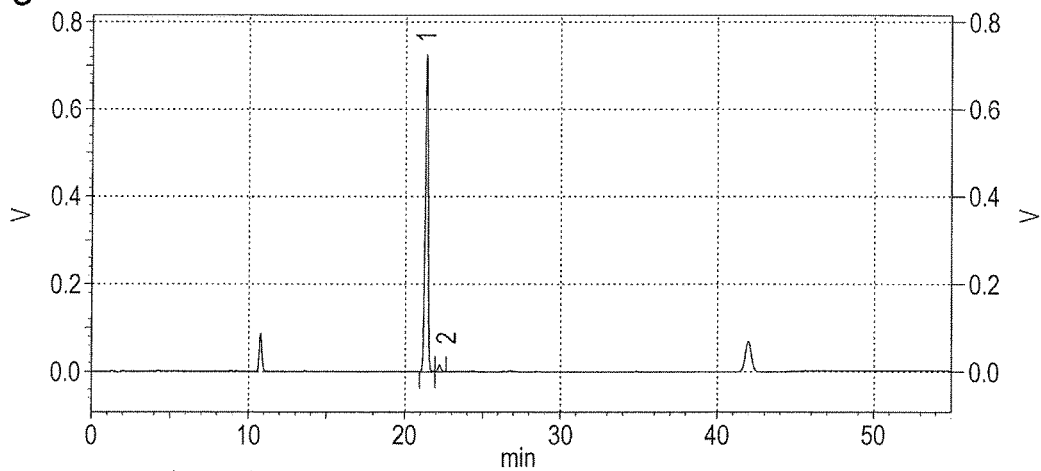
FIG. 18 shows a HPLC analysis result of a Ni (II) complex obtained in Example 4-6, which has L-alanine as a partial structure.

The product of this Example was analyzed under HPLC conditions-1: complex analysis conditions. The results are shown in FIG. 18.

L-alanine can be obtained by processing this complex in the same manner as in Example 3-1.

Example 4-7

Synthesis of D-tyrosine by Deracemization of DL-tyrosine

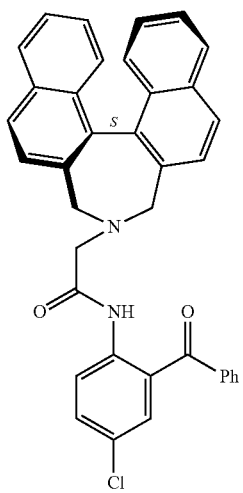

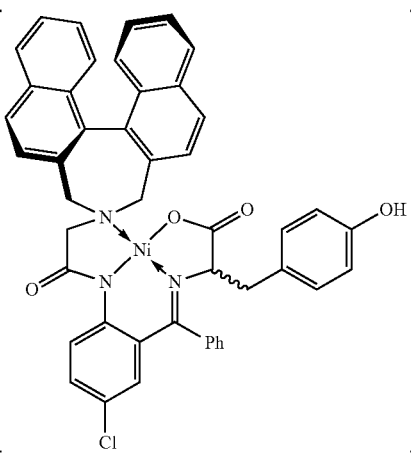

-continued

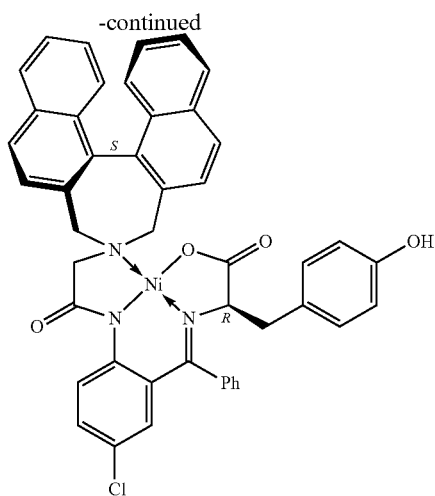

To a methanol suspension (1 mL) of (S)-N-(2-benzoyl-4-chlorophenyl)-2-[3,5-dihydro-4H-dinaphtho[2,1-c: 1',2'-e]azepin-4-yl]acetamide (0.2 g, 0.352 mmol), nickel chloride (0.0913 g, 0.704 mmol), DL-tyrosine (0.128 g, 0.704 mmol), and potassium carbonate (0.293 g, 2.18 mmol) were added, and the mixture was refluxed for 16 hours. After the end of the reaction, the reaction mixture was added to an ice-cooled 5% acetic acid aqueous solution (80 mL) and stirred for 30 minutes to allow crystals to precipitate. The crystals were separated by filtration, and then vacuum-dried at 50° C. to give a nickel (II) complex having a D-tyrosine moiety (0.273 g, yield: 98.48, 92.6% de) as an orange-red solid.

ESI-MS (positive mode): m/z=786.4 for [M+H]$^+$.

$^1$H-NMR (200 MHz, CDCl$_3$): δ2.44 [1H, d, J=12.1 Hz, one of azepine C(α)H$_2$N], 2.49 (1H, H$_A$ of ABX type, J$_{AB}$=13.9 Hz, J$_{AX}$=4.9 Hz, one of Tyr β-CH$_2$), 2.71 [1H, d, J=15.7 Hz, one of azepine C(α)H$_2$N], 2.92 (1H, H$_B$ of ABX type, J$_{AB}$=13.9 Hz, J$_{BX}$=2.7 Hz, one of Tyr β-CH$_2$), 2.99 and 3.19 (1H each, ABq, J=13.9 Hz, acetanilide NCOCH$_2$), 3.92 [1H, d, J=15.7 Hz, one of azepine C(α')H$_2$N], 4.18 (1H, H$_X$ of ABX type, J$_{AX}$=4.9 Hz, J$_{BX}$=2.7 Hz, α-H of Tyr part), 4.59 [1H, d, J=12.1 Hz, one of azepine C (α) H$_2$N], 6.67 (1H, d, J=2.6 Hz) , 6.93-7.00 (1H, m, ArH) , 7.09-7.62 (16H, m, ArH), 7.77 (1H, d, J=7.9 Hz, ArH), 7.81 (1H, d, J=7.7 Hz, ArH), 7.92 (1H, d, J=8.2 Hz, ArH), 8.09 (1H, d, J=8.2 Hz, ArH), 8.32 (1H, d, J=9.0 Hz, ArH), 8.56 (1H, br, OH), 8.70 (1H, d, J=8.4 Hz, ArH).

$^{13}$C-NMR (50.3 MHz, CDCl$_3$): δ38.3 (β-C$_2$ of Tyr part), 57.6 (NCOCH$_2$), 61.8 and 65.8 (2×CH$_2$ of azepine), 72.4 (α-CH of Tyr part), 125.3 (ArCH), 126.3 (ArCH), 126.4 (ArCH), 126.5 (quaternary ArC), 126.9 (quaternary ArC) , 127.1 (ArCH), 127.4 (ArCH), 127.5 (ArCH), 127.7 (ArCH), 128.4 (ArCH), 128.55 (ArCH), 128.59 (quaternary ArC), 128.3 (quaternary ArC), 129.1 (ArCH), 129.4 (ArCH), 130.5 (ArCH), 130.0 (quaternary ArC), 131.1 (quaternary ArC), 131.3 (quaternary ArC), 132.5 (ArCH), 132.6 (ArCH), 132.7 (quaternary ArC), 133.5 (quaternary ArC), 133.9 (quaternary ArC), 135.2 (quaternary ArC), 136.0 (quaternary ArC), 140.7 (quaternary ArC), 157.0 (quaternary ArC), 169.9, 174.9, 177.9 (CN and 2×CO).

Figure 19:
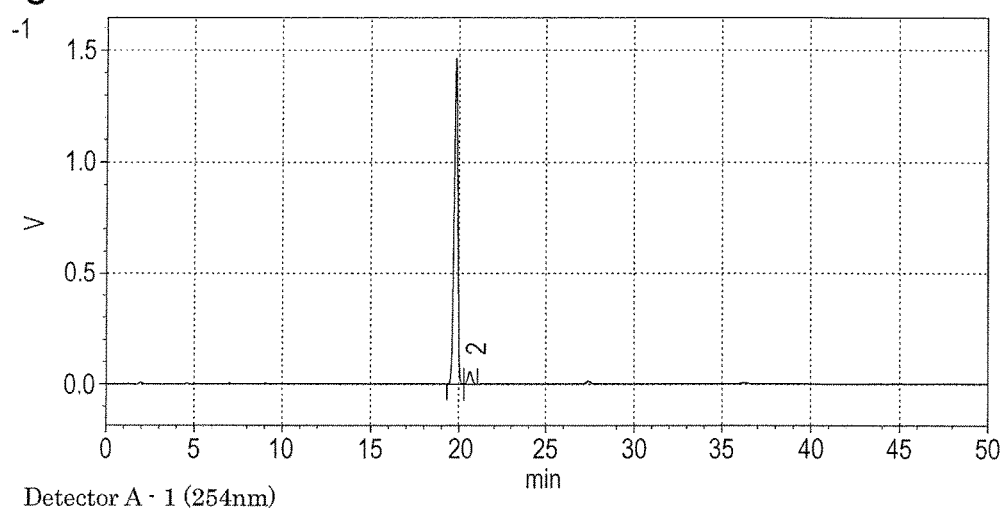
FIG. 19 shows a HPLC analysis result of a Ni (II) complex obtained in example 4-7, which has D-tyrosine as a partial structure.

The product of this Example was analyzed under HPLC conditions-1: complex analysis conditions. The results are shown in FIG. 19.

INDUSTRIAL APPLICABILITY

According to the present invention, by using an appropriately selected optical isomer of a novel N—(2-acylaryl) -2-[5,7-dihydro-6H-dibenzo[c,e]azepin-6-yl]acetamide compound as a chiral template, the chirality of an α-amino acid can be interconverted to give an α-amino acid having a desired chirality in high yield and in a highly enantioselective manner. In particular, the present invention is useful for the production of an optically active unnatural α-amino acid.

The invention claimed is:
1. An N—(2-acylaryl)-2-[5,7-dihydro-6H-dibenzo[c,e]azepin-6-yl]acetamide compound represented by Formula (1):

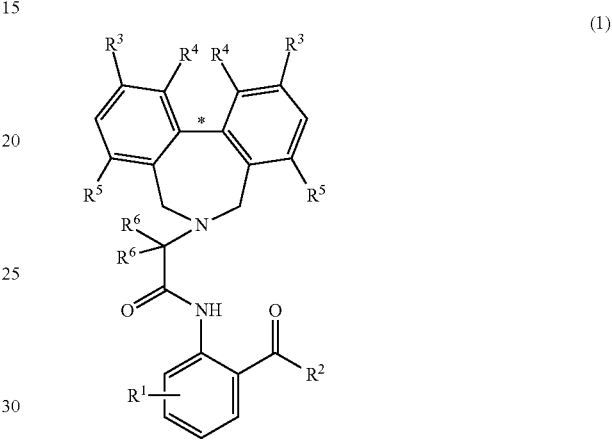

(1)

(wherein R$^1$ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, a halogen atom, or a nitro group;

R$^2$ denotes hydrogen, an optionally substituted alkyl group, an optionally substituted alkynyl group, an optionally substituted alkenyl group, an optionally substituted cycloalkyl group, an optionally substituted aryl group, or an optionally substituted heteroaryl group;

R$^3$ and R$^4$ each independently denote hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, or a halogen atom;

the two R$^3$s may be the same or different;
the two R$^4$s may be the same or different;
R$^3$ and R$^4$ may form a ring together with the carbon atoms to which they are bonded;

R$^5$ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, a carboxyl group, a halogen atom, —COOR$^7$, or —C(OH)(R$^7$)$_2$;
the two R$^5$s may be the same or different;

R$^6$ denotes hydrogen, an optionally substituted alkyl group, an optionally substituted cycloalkyl group, or a halogen atom;

the two $R^6$s may be the same or different;

the two $R^6$s may form a ring together with the carbon atom to which they are bonded;

$R^7$ denotes hydrogen, an optionally substituted alkyl group, an optionally substituted aryl group, or an optionally substituted heteroaryl group;

and * denotes a chiral axis), or a salt thereof.

2. The compound according to claim 1 or a salt thereof, wherein, in each of the two pairs of $R^3$ and $R^4$ in Formula (1), $R^3$ and $R^4$ form an aromatic ring or an alicyclic structure together with the benzene-ring carbon atoms to which they are bonded; and $R^2$ denotes a group represented by the following formula:

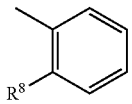

(wherein $R^8$ denotes a hydrogen atom or a halogen atom).

3. The compound according to claim 2, wherein $R^1$ is hydrogen, chlorine, a methyl group, or a nitro group; and $R^5$ and $R^6$ are each hydrogen.

4. A metal complex represented by Formula (3):

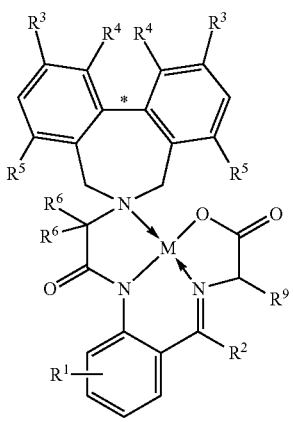

(wherein $R^1$ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, a halogen atom, or a nitro group;

$R^2$ denotes hydrogen, an optionally substituted alkyl group, an optionally substituted alkynyl group, an optionally substituted alkenyl group, an optionally substituted cycloalkyl group, an optionally substituted aryl group, or an optionally substituted heteroaryl group, $R^3$ and $R^4$ each independently denote hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, or a halogen atom;

the two $R^3$s may be the same or different;

the two $R^4$s may be the same or different;

$R^3$ and $R^4$ may form a ring together with the carbon atoms to which they are bonded;

$R^5$ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, a carboxyl group, a halogen atom, —COOR$^7$, or —C(OH)(R$^7$)$_2$;

the two $R^5$s may be the same or different;

$R^6$ denotes hydrogen, an optionally substituted alkyl group, an optionally substituted cycloalkyl group, or a halogen atom;

the two $R^6$s may be the same or different;

the two $R^6$s may form a ring together with the carbon atom to which they are bonded;

$R^7$ denotes hydrogen, an optionally substituted alkyl group, an optionally substituted aryl group, or an optionally substituted heteroaryl group; and $R^9$ denotes an optionally substituted alkyl group, an optionally substituted alkynyl group, an optionally substituted alkenyl group, an optionally substituted cycloalkyl group, an optionally substituted aryl group, an optionally substituted heteroaryl group, an optionally substituted aralkyl group, or an optionally substituted heteroarylalkyl group;

* denotes a chiral axis; and

M denotes a divalent metallic cation).

5. The metal complex according to claim 4, wherein, in each of the two pairs of $R^3$ and $R^4$ in Formula (3), $R^3$ and $R^4$ form an aromatic ring or an alicyclic structure together with the benzene-ring carbon atoms to which they are bonded; and $R^2$ denotes a group represented by the following formula:

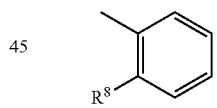

(wherein $R^8$ denotes a hydrogen atom or a halogen atom).

6. The metal complex according to claim 4, wherein $R^1$ is hydrogen, chlorine, a methyl group, or a nitro group; in each of the two pairs of $R^3$ and $R^4$, $R^3$ and $R^4$ form an aromatic ring or an alicyclic structure together with the benzene-ring carbon atoms to which they are bonded; $R^5$ and $R^6$ are each hydrogen; and M denotes a nickel cation, a copper cation, a palladium cation, or a platinum cation.

7. A method for interconverting the configuration of an α-amino acid, the method comprising heating, under basic conditions, the divalent metal cation complex represented by Formula (3) in claim 4 derived from an imine compound produced from a selected optically active R- or S-isomer of the N-(2-acylaryl)-2-[5,7-dihydro-6-H-dibenzo[c,e]azepin-6-yl]acetamide compound represented by Formula (1)

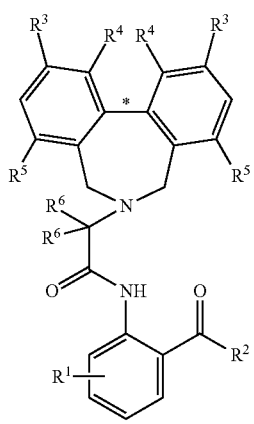

(1)

(wherein $R^1$ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, a halogen atom, or a nitro group;

$R^2$ denotes hydrogen, an optionally substituted alkyl group, an optionally substituted alkynyl group, an optionally substituted alkenyl group, an optionally substituted cycloalkyl group, an optionally substituted aryl group, or an optionally substituted heteroaryl group;

$R^3$ and $R^4$ each independently denote hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, or a halogen atom;

the two $R^3$s may be the same or different;

the two $R^4$s may be the same or different;

$R^3$ and $R^4$ may form a ring together with the carbon atoms to which they are bonded;

$R^5$ denotes hydrogen, an optionally substituted alkyl group, an optionally substituted alkynyl group, an optionally substituted alkenyl group, an optionally substituted alkoxy group, an optionally substituted cycloalkyl group, an optionally substituted aryl group, an optionally substituted heteroaryl group, a carboxyl group, a halogen atom, $-COOR^7$, or $-C(OH)(R^7)_2$;

the two $R^5$s may be the same or different;

$R^6$ denotes hydrogen, an optionally substituted alkyl group, an optionally substituted cycloalkyl group, or a halogen atom;

the two $R^6$s may be the same or different;

the two $R^6$s may form a ring together with the carbon atom to which they are bonded;

$R^7$ denotes hydrogen, an optionally substituted alkyl group, an optionally substituted aryl group, or an optionally substituted heteroaryl group;

and * denotes a chiral axis), or a salt thereof and an α-amino acid in order to interconvert the configuration of the α carbon in the α-amino acid moiety, followed by subjecting the metal complex to acid decomposition to release the chirality-converted α-amino acid to give an optically pure enantiomer of α-amino acid.

8. The method according to claim 7, wherein the α-amino acid is represented by Formula (5):

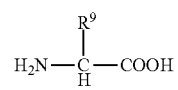

(5)

(wherein $R^9$ denotes an optionally substituted alkyl group, an optionally substituted alkynyl group, an optionally substituted alkenyl group, an optionally substituted cycloalkyl group, an optionally substituted aryl group, an optionally substituted heteroaryl group, an optionally substituted aralkyl group, or an optionally substituted heteroarylalkyl group) and is a mixture of optical isomers or a pure optical isomer.

9. The metal complex according to claim 5, wherein $R^1$ is hydrogen, chlorine, a methyl group, or a nitro group; in each of the two pairs of $R^3$ and $R^4$, $R^3$ and $R^4$ form an aromatic ring or an alicyclic structure together with the benzene-ring carbon atoms to which they are bonded; $R^5$ and $R^6$ are each hydrogen; and M denotes a nickel cation, a copper cation, a palladium cation, or a platinum cation.

* * * * *